(12) United States Patent
Moon et al.

(10) Patent No.: US 11,607,152 B2
(45) Date of Patent: Mar. 21, 2023

(54) OPTICAL SENSORS FOR USE IN VITAL SIGN MONITORING

(75) Inventors: Jim Moon, Portland, OR (US); Devin McCombie, San Diego, CA (US); Matt Banet, Kihei, HI (US); Marshal Dhillon, San Diego, CA (US)

(73) Assignee: SOTERA WIRELESS, INC.

( * ) Notice: Subject to any disclaimer, the term of this patent is extended or adjusted under 35 U.S.C. 154(b) by 0 days.

(21) Appl. No.: 13/292,923

(22) Filed: Nov. 9, 2011

(65) Prior Publication Data

US 2012/0179011 A1 Jul. 12, 2012

Related U.S. Application Data

(63) Continuation-in-part of application No. 12/650,374, filed on Dec. 30, 2009, now Pat. No. 9,161,700, and
(Continued)

(51) Int. Cl.
*A61B 5/11* (2006.01)
*A61B 5/00* (2006.01)
(Continued)

(52) U.S. Cl.
CPC .......... *A61B 5/1116* (2013.01); *A61B 5/1118* (2013.01); *A61B 5/14551* (2013.01);
(Continued)

(58) Field of Classification Search
None
See application file for complete search history.

(56) References Cited

U.S. PATENT DOCUMENTS

| 4,086,916 A | 5/1978 | Freeman et al. |
| 4,263,918 A | 4/1981 | Swearingen et al. |

(Continued)

FOREIGN PATENT DOCUMENTS

| CN | 101224107 A | 7/2008 |
| CN | 101262813 A | 9/2008 |

(Continued)

OTHER PUBLICATIONS

Non-Final Office Action issued by the US Patent and Trademark Office dated Aug. 31, 2012 in U.S. Appl. No. 12/469,213.
(Continued)

*Primary Examiner* — Michael R Bloch
(74) *Attorney, Agent, or Firm* — Acuity Law Group PC; Michael A. Whittaker

(57) ABSTRACT

The invention provides a body-worn system that continuously measures pulse oximetry and blood pressure, along with motion, posture, and activity level, from an ambulatory patient. The system features an oximetry probe that comfortably clips to the base of the patient's thumb, thereby freeing up their fingers for conventional activities in a hospital, such as reading and eating. The probe secures to the thumb and measures time-dependent signals corresponding to LEDs operating near 660 and 905 nm. Analog versions of these signals pass through a low-profile cable to a wrist-worn transceiver that encloses a processing unit. Also within the wrist-worn transceiver is an accelerometer, a wireless system that sends information through a network to a remote receiver, e.g. a computer located in a central nursing station.

9 Claims, 24 Drawing Sheets

Related U.S. Application Data a continuation-in-part of application No. 12/559,413, filed on Sep. 14, 2009, now Pat. No. 8,554,297, and a continuation-in-part of application No. 12/487,283, filed on Jun. 18, 2009, now abandoned, and a continuation-in-part of application No. 12/171,886, filed on Jul. 11, 2008, now Pat. No. 8,506,480, and a continuation-in-part of application No. 12/138,194, filed on Jun. 12, 2008, now Pat. No. 8,419,649, said application No. 12/650,374 is a continuation-in-part of application No. 12/138,194, filed on Jun. 12, 2008, now Pat. No. 8,419,649.

(60) Provisional application No. 61/218,062, filed on Jun. 17, 2009, provisional application No. 61/218,057, filed on Jun. 17, 2009, provisional application No. 61/218,060, filed on Jun. 17, 2009, provisional application No. 61/218,055, filed on Jun. 17, 2009, provisional application No. 61/218,061, filed on Jun. 17, 2009, provisional application No. 61/218,059, filed on Jun. 17, 2009, provisional application No. 61/073,681, filed on Jun. 18, 2008, provisional application No. 60/983,198, filed on Oct. 28, 2007, provisional application No. 60/949,052, filed on Jul. 11, 2007, provisional application No. 60/943,464, filed on Jun. 12, 2007.

(51) Int. Cl.
*A61B 5/1455* (2006.01)
*A61B 5/25* (2021.01)
*A61B 5/022* (2006.01)
*A61B 5/0245* (2006.01)
*A61B 5/08* (2006.01)
*A61B 5/0205* (2006.01)

(52) U.S. Cl.
CPC .............. *A61B 5/25* (2021.01); *A61B 5/6826* (2013.01); *A61B 5/6838* (2013.01); *A61B 5/7207* (2013.01); *A61B 5/0002* (2013.01); *A61B 5/0245* (2013.01); *A61B 5/02055* (2013.01); *A61B 5/02225* (2013.01); *A61B 5/0816* (2013.01); *A61B 5/1117* (2013.01); *A61B 5/7225* (2013.01); *A61B 5/7239* (2013.01); *A61B 5/746* (2013.01); *A61B 2560/0412* (2013.01); *A61B 2560/0462* (2013.01); *A61B 2560/0468* (2013.01); *A61B 2562/0219* (2013.01)

(56) References Cited

U.S. PATENT DOCUMENTS

| | | |
|---|---|---|
| 4,270,547 A | 6/1981 | Steffen et al. |
| 4,305,400 A | 12/1981 | Logan |
| 4,367,752 A | 1/1983 | Jimenez et al. |
| 4,577,639 A | 3/1986 | Simon et al. |
| 4,582,068 A | 4/1986 | Phillipps et al. |
| 4,653,498 A | 3/1987 | New, Jr. et al. |
| 4,710,164 A | 12/1987 | Levin et al. |
| 4,722,351 A | 2/1988 | Phillipps et al. |
| 4,802,486 A | 2/1989 | Goodman et al. |
| 4,807,638 A | 2/1989 | Sramek |
| 4,830,014 A | 5/1989 | Goodman et al. |
| 4,905,697 A | 3/1990 | Heggs et al. |
| 5,025,791 A | 6/1991 | Niwa |
| 5,140,990 A | 8/1992 | Jones et al. |
| 5,190,038 A | 3/1993 | Polson et al. |
| 5,197,489 A | 3/1993 | Conlan |
| 5,224,928 A | 7/1993 | Sibalis et al. |
| 5,247,931 A | 9/1993 | Norwood |
| 5,289,824 A | 3/1994 | Mills et al. |
| 5,316,008 A | 5/1994 | Suga et al. |
| 5,339,818 A | 8/1994 | Baker et al. |
| 5,423,322 A | 6/1995 | Clark et al. |
| 5,435,315 A | 7/1995 | McPhee et al. |
| 5,448,991 A | 9/1995 | Polson et al. |
| 5,465,082 A | 11/1995 | Chaco |
| 5,482,036 A | 1/1996 | Diab et al. |
| 5,485,838 A | 1/1996 | Ukawa et al. |
| 5,490,505 A | 2/1996 | Diab et al. |
| 5,515,858 A | 5/1996 | Myllymaki |
| 5,517,988 A | 5/1996 | Gerhard |
| 5,524,637 A | 6/1996 | Erickson |
| 5,549,650 A | 8/1996 | Bornzin et al. |
| 5,575,284 A | 11/1996 | Athan et al. |
| 5,577,508 A | 11/1996 | Medero |
| 5,588,427 A | 12/1996 | Tien |
| 5,593,431 A | 1/1997 | Sheldon |
| 5,632,272 A | 5/1997 | Diab et al. |
| 5,645,060 A | 7/1997 | Yorkey |
| 5,649,543 A | 7/1997 | Hosaka et al. |
| 5,680,870 A | 10/1997 | Hood et al. |
| 5,685,299 A | 11/1997 | Diab et al. |
| 5,709,205 A | 1/1998 | Bukta |
| 5,743,856 A | 4/1998 | Oka et al. |
| 5,766,131 A | 6/1998 | Kondo et al. |
| 5,769,785 A | 6/1998 | Diab et al. |
| 5,800,349 A | 9/1998 | Isaacson et al. |
| 5,820,550 A | 10/1998 | Polson et al. |
| 5,848,373 A | 12/1998 | Delorme et al. |
| 5,853,370 A | 12/1998 | Chance et al. |
| 5,857,975 A | 1/1999 | Golub |
| 5,865,755 A | 2/1999 | Golub |
| 5,865,756 A | 2/1999 | Peel, III |
| 5,873,834 A | 2/1999 | Yanagi et al. |
| 5,876,353 A | 3/1999 | Riff |
| 5,895,359 A | 4/1999 | Peel, III |
| 5,899,855 A | 5/1999 | Brown |
| 5,906,582 A | 5/1999 | Kondo et al. |
| 5,913,827 A | 6/1999 | Gorman |
| 5,919,141 A | 7/1999 | Money et al. |
| 5,941,836 A | 8/1999 | Friedman |
| 5,964,701 A | 10/1999 | Asada et al. |
| 5,964,720 A | 10/1999 | Pelz |
| 5,971,930 A | 10/1999 | Elghazzawi |
| 6,002,952 A | 12/1999 | Diab et al. |
| 6,011,985 A | 1/2000 | Athan et al. |
| 6,018,673 A | 1/2000 | Chin et al. |
| 6,027,455 A | 2/2000 | Inukai et al. |
| 6,036,642 A | 3/2000 | Diab et al. |
| 6,041,783 A | 3/2000 | Gruenke |
| 6,057,758 A | 5/2000 | Dempsey et al. |
| 6,067,462 A | 5/2000 | Diab et al. |
| 6,081,735 A | 6/2000 | Diab et al. |
| 6,081,742 A | 6/2000 | Amano et al. |
| 6,094,592 A | 7/2000 | Yorkey et al. |
| 6,117,077 A | 9/2000 | Del Mar et al. |
| 6,129,686 A | 10/2000 | Friedman |
| 6,157,850 A | 12/2000 | Diab et al. |
| 6,159,147 A | 12/2000 | Lighter et al. |
| 6,160,478 A | 12/2000 | Jacobsen et al. |
| 6,168,569 B1 | 1/2001 | McEwen et al. |
| 6,176,831 B1 | 1/2001 | Voss et al. |
| 6,198,394 B1 | 3/2001 | Jacobsen et al. |
| 6,198,951 B1 | 3/2001 | Kosuda et al. |
| 6,199,550 B1 | 3/2001 | Wiesmann et al. |
| 6,206,830 B1 | 3/2001 | Diab et al. |
| 6,236,872 B1 | 5/2001 | Diab et al. |
| 6,251,080 B1 | 6/2001 | Henkin et al. |
| 6,261,247 B1 | 7/2001 | Ishikawa et al. |
| 6,262,769 B1 | 7/2001 | Anderson et al. |
| 6,263,222 B1 | 7/2001 | Diab et al. |
| 6,287,262 B1 | 9/2001 | Amano et al. |
| 6,322,516 B1 | 11/2001 | Masuda et al. |
| 6,334,065 B1 | 12/2001 | Al-Ali et al. |
| 6,371,921 B1 | 4/2002 | Caro et al. |
| 6,388,240 B2 | 5/2002 | Schulz et al. |
| RE37,852 E | 9/2002 | Aso et al. |
| 6,443,890 B1 | 9/2002 | Schulze et al. |

(56) References Cited

U.S. PATENT DOCUMENTS

| | | |
|---|---|---|
| 6,480,729 B2 | 11/2002 | Stone |
| 6,491,647 B1 | 12/2002 | Bridger et al. |
| 6,503,206 B1 | 1/2003 | Li et al. |
| 6,514,218 B2 | 2/2003 | Yamamoto |
| 6,516,289 B2 | 2/2003 | David |
| 6,526,310 B1 | 2/2003 | Carter et al. |
| 6,527,729 B1 | 3/2003 | Turcott |
| 6,533,729 B1 | 3/2003 | Khair et al. |
| 6,541,756 B2 | 4/2003 | Schulz et al. |
| 6,544,173 B2 | 4/2003 | West et al. |
| 6,544,174 B2 | 4/2003 | West et al. |
| 6,546,267 B1 | 4/2003 | Sugiura et al. |
| 6,551,252 B2 | 4/2003 | Sackner et al. |
| 6,584,336 B1 | 6/2003 | Ali et al. |
| 6,589,170 B1 | 7/2003 | Flach et al. |
| 6,595,929 B2 | 7/2003 | Stivoric et al. |
| 6,605,038 B1 | 8/2003 | Teller et al. |
| 6,606,993 B1 | 8/2003 | Wiesmann et al. |
| 6,616,606 B1 | 9/2003 | Petersen et al. |
| 6,645,154 B2 | 11/2003 | Oka |
| 6,650,917 B2 | 11/2003 | Diab et al. |
| 6,684,090 B2 | 1/2004 | Ali et al. |
| 6,694,177 B2 | 2/2004 | Eggers et al. |
| 6,699,194 B1 | 3/2004 | Diab et al. |
| 6,732,064 B1 | 5/2004 | Kadtke et al. |
| 6,745,060 B2 | 6/2004 | Diab et al. |
| 6,770,028 B1 | 8/2004 | Ali et al. |
| 6,790,178 B1 | 9/2004 | Mault et al. |
| 6,801,798 B2 * | 10/2004 | Geddes .............. A61B 5/02233 600/323 |
| 6,811,538 B2 | 11/2004 | Westbrook et al. |
| 6,845,256 B2 | 1/2005 | Chin et al. |
| 6,850,787 B2 | 2/2005 | Weber et al. |
| 6,879,850 B2 | 4/2005 | Kimball |
| 6,893,396 B2 | 5/2005 | Schulze et al. |
| 6,912,414 B2 | 6/2005 | Tong |
| 6,934,571 B2 | 8/2005 | Wiesmann et al. |
| 6,947,781 B2 | 9/2005 | Asada et al. |
| 6,976,958 B2 | 12/2005 | Quy |
| 6,985,078 B2 | 1/2006 | Suzuki et al. |
| 6,997,882 B1 | 2/2006 | Parker et al. |
| 7,020,508 B2 | 3/2006 | Stivoric et al. |
| 7,020,578 B2 | 3/2006 | Sorensen et al. |
| 7,029,447 B2 | 4/2006 | Rantala |
| 7,041,060 B2 | 5/2006 | Flaherty et al. |
| 7,048,687 B1 | 5/2006 | Reuss et al. |
| 7,079,888 B2 | 7/2006 | Oung et al. |
| 7,115,824 B2 | 10/2006 | Lo |
| 7,156,809 B2 | 1/2007 | Quy |
| 7,184,809 B1 | 2/2007 | Sterling et al. |
| 7,186,966 B2 | 3/2007 | Al-Ali |
| 7,194,293 B2 | 3/2007 | Baker, Jr. |
| 7,215,984 B2 | 5/2007 | Diab et al. |
| 7,215,987 B1 | 5/2007 | Sterling et al. |
| 7,225,007 B2 | 5/2007 | Al-Ali et al. |
| 7,237,446 B2 | 7/2007 | Chan et al. |
| 7,241,265 B2 | 7/2007 | Cummings et al. |
| 7,257,438 B2 | 8/2007 | Kinast |
| 7,296,312 B2 | 11/2007 | Menkedick et al. |
| 7,299,159 B2 | 11/2007 | Nanikashvili |
| 7,301,451 B2 | 11/2007 | Hastings |
| 7,314,451 B2 | 1/2008 | Halperin et al. |
| 7,351,206 B2 | 4/2008 | Suzuki et al. |
| 7,355,512 B1 | 4/2008 | Al-Ali |
| 7,373,191 B2 | 5/2008 | Delonzer et al. |
| 7,373,912 B2 | 5/2008 | Self et al. |
| 7,377,794 B2 | 5/2008 | Al-Ali et al. |
| 7,382,247 B2 | 6/2008 | Welch et al. |
| 7,383,069 B2 | 6/2008 | Ruchti et al. |
| 7,383,070 B2 | 6/2008 | Diab et al. |
| 7,384,398 B2 | 6/2008 | Gagnadre et al. |
| 7,400,919 B2 | 7/2008 | Petersen et al. |
| 7,420,472 B2 | 9/2008 | Tran |
| 7,427,926 B2 | 9/2008 | Sinclair et al. |
| 7,455,643 B1 | 11/2008 | Li et al. |
| 7,460,897 B1 | 12/2008 | Flessland et al. |
| 7,468,036 B1 | 12/2008 | Rulkov et al. |
| 7,477,143 B2 | 1/2009 | Albert |
| 7,479,890 B2 | 1/2009 | Lehrman et al. |
| 7,485,095 B2 | 2/2009 | Shusterman |
| 7,502,643 B2 | 3/2009 | Farringdon et al. |
| 7,508,307 B2 | 3/2009 | Albert |
| 7,509,131 B2 | 3/2009 | Krumm et al. |
| 7,509,154 B2 | 3/2009 | Diab et al. |
| 7,522,035 B2 | 4/2009 | Albert |
| 7,530,949 B2 | 5/2009 | Al-Ali et al. |
| 7,539,532 B2 | 5/2009 | Tran |
| 7,541,939 B2 | 6/2009 | Zadesky et al. |
| 7,542,878 B2 | 6/2009 | Nanikashvili |
| 7,586,418 B2 | 9/2009 | Cuddihy et al. |
| 7,598,878 B2 | 10/2009 | Goldreich |
| 7,602,301 B1 | 10/2009 | Stirling et al. |
| 7,616,110 B2 | 11/2009 | Crump et al. |
| 7,625,344 B1 | 12/2009 | Brady et al. |
| 7,628,071 B2 | 12/2009 | Sasaki et al. |
| 7,628,730 B2 | 12/2009 | Watterson et al. |
| 7,641,614 B2 | 1/2010 | Asada et al. |
| 7,648,463 B1 | 1/2010 | Elhag et al. |
| 7,656,287 B2 | 2/2010 | Albert et al. |
| 7,668,588 B2 | 2/2010 | Kovacs |
| 7,670,295 B2 | 3/2010 | Sackner et al. |
| 7,674,230 B2 | 3/2010 | Reisfeld |
| 7,674,231 B2 | 3/2010 | McCombie et al. |
| 7,678,061 B2 | 3/2010 | Lee et al. |
| 7,684,954 B2 | 3/2010 | Shahabdeen et al. |
| 7,689,437 B1 | 3/2010 | Teller et al. |
| 7,698,101 B2 | 4/2010 | Alten et al. |
| 7,698,830 B2 | 4/2010 | Townsend et al. |
| 7,698,941 B2 | 4/2010 | Sasaki et al. |
| 7,715,984 B2 | 5/2010 | Ramakrishnan et al. |
| 7,725,147 B2 | 5/2010 | Li et al. |
| 7,782,189 B2 | 8/2010 | Spoonhower et al. |
| 7,827,011 B2 | 11/2010 | Devaul et al. |
| 7,925,022 B2 | 4/2011 | Jung et al. |
| 7,976,480 B2 | 7/2011 | Grajales et al. |
| 7,983,933 B2 | 7/2011 | Karkanias et al. |
| 8,047,998 B2 | 11/2011 | Kolluri et al. |
| 8,082,160 B2 | 12/2011 | Collins, Jr. et al. |
| 8,137,270 B2 | 3/2012 | Keenan et al. |
| 8,167,800 B2 | 5/2012 | Ouchi et al. |
| 2001/0004234 A1 | 6/2001 | Petelenz et al. |
| 2001/0007923 A1 | 7/2001 | Yamamoto |
| 2001/0013826 A1 | 8/2001 | Ahmed et al. |
| 2001/0045395 A1 | 11/2001 | Kitaevich et al. |
| 2002/0013517 A1 | 1/2002 | West et al. |
| 2002/0032386 A1 | 3/2002 | Sackner et al. |
| 2002/0072859 A1 | 6/2002 | Kajimoto et al. |
| 2002/0151805 A1 | 10/2002 | Sugo et al. |
| 2002/0156354 A1 | 10/2002 | Larson |
| 2002/0169381 A1 | 11/2002 | Asada et al. |
| 2002/0170193 A1 | 11/2002 | Townsend et al. |
| 2002/0183627 A1 | 12/2002 | Nishii et al. |
| 2002/0193671 A1 | 12/2002 | Ciurczak et al. |
| 2002/0193692 A1 | 12/2002 | Inukai et al. |
| 2002/0198679 A1 | 12/2002 | Victor et al. |
| 2003/0004420 A1 | 1/2003 | Narimatsu |
| 2003/0045785 A1 | 3/2003 | Diab et al. |
| 2003/0097046 A1 | 5/2003 | Sakamaki et al. |
| 2003/0130590 A1 | 7/2003 | Bui et al. |
| 2003/0135099 A1 | 7/2003 | Al-Ali |
| 2003/0153836 A1 | 8/2003 | Gagnadre et al. |
| 2003/0158699 A1 | 8/2003 | Townsend et al. |
| 2003/0167012 A1 | 9/2003 | Friedman et al. |
| 2003/0171662 A1 | 9/2003 | O'Conner et al. |
| 2003/0181815 A1 | 9/2003 | Ebner et al. |
| 2003/0208335 A1 | 11/2003 | Unuma et al. |
| 2004/0019288 A1 | 1/2004 | Kinast |
| 2004/0030261 A1 | 2/2004 | Rantala |
| 2004/0034293 A1 | 2/2004 | Kimball |
| 2004/0034294 A1 | 2/2004 | Kimball et al. |
| 2004/0054821 A1 | 3/2004 | Warren et al. |
| 2004/0073128 A1 | 4/2004 | Hatlestad et al. |
| 2004/0077934 A1 | 4/2004 | Massad |
| 2004/0111033 A1 | 6/2004 | Oung et al. |

(56) References Cited

U.S. PATENT DOCUMENTS

| | | |
|---|---|---|
| 2004/0122315 A1 | 6/2004 | Krill |
| 2004/0133079 A1 | 7/2004 | Mazar et al. |
| 2004/0162466 A1 | 8/2004 | Quy |
| 2004/0162493 A1 | 8/2004 | Mills |
| 2004/0193063 A1 | 9/2004 | Kimura et al. |
| 2004/0225207 A1 | 11/2004 | Bae et al. |
| 2004/0267099 A1 | 12/2004 | McMahon et al. |
| 2005/0027205 A1 | 2/2005 | Tarassenko et al. |
| 2005/0043598 A1 | 2/2005 | Goode, Jr. et al. |
| 2005/0059870 A1 | 3/2005 | Aceti |
| 2005/0070773 A1 | 3/2005 | Chin et al. |
| 2005/0075550 A1* | 4/2005 | Lindekugel .............. 600/344 |
| 2005/0113107 A1 | 5/2005 | Meunier |
| 2005/0113703 A1 | 5/2005 | Farringdon et al. |
| 2005/0119586 A1 | 6/2005 | Coyle et al. |
| 2005/0119833 A1 | 6/2005 | Nanikashvili |
| 2005/0124866 A1 | 6/2005 | Elaz et al. |
| 2005/0124903 A1 | 6/2005 | Roteliuk et al. |
| 2005/0149350 A1 | 7/2005 | Kerr et al. |
| 2005/0171444 A1 | 8/2005 | Ono et al. |
| 2005/0187796 A1 | 8/2005 | Rosenfeld et al. |
| 2005/0206518 A1 | 9/2005 | Welch et al. |
| 2005/0209511 A1 | 9/2005 | Heruth et al. |
| 2005/0228296 A1 | 10/2005 | Banet |
| 2005/0228298 A1 | 10/2005 | Banet et al. |
| 2005/0228301 A1 | 10/2005 | Banet et al. |
| 2005/0234317 A1 | 10/2005 | Kiani |
| 2005/0240087 A1 | 10/2005 | Keenan et al. |
| 2005/0261565 A1 | 11/2005 | Lane et al. |
| 2005/0261593 A1 | 11/2005 | Zhang et al. |
| 2005/0265267 A1 | 12/2005 | Hwang |
| 2005/0283088 A1 | 12/2005 | Bernstein |
| 2006/0036141 A1 | 2/2006 | Kamath et al. |
| 2006/0047215 A1 | 3/2006 | Newman et al. |
| 2006/0074321 A1 | 4/2006 | Kouchi et al. |
| 2006/0074322 A1 | 4/2006 | Nitzan |
| 2006/0122469 A1 | 6/2006 | Martel |
| 2006/0122520 A1* | 6/2006 | Banet .............. A61B 5/021 600/503 |
| 2006/0128263 A1 | 6/2006 | Baird |
| 2006/0142648 A1 | 6/2006 | Banet et al. |
| 2006/0155589 A1 | 7/2006 | Lane et al. |
| 2006/0178591 A1 | 8/2006 | Hempfling |
| 2006/0200029 A1 | 9/2006 | Evans et al. |
| 2006/0252999 A1 | 11/2006 | Devaul et al. |
| 2006/0265246 A1 | 11/2006 | Hoag |
| 2006/0270949 A1 | 11/2006 | Mathie et al. |
| 2006/0271404 A1 | 11/2006 | Brown |
| 2006/0281979 A1 | 12/2006 | Kim et al. |
| 2007/0010719 A1 | 1/2007 | Huster et al. |
| 2007/0055163 A1 | 3/2007 | Asada et al. |
| 2007/0066910 A1 | 3/2007 | Inukai et al. |
| 2007/0071643 A1 | 3/2007 | Hall et al. |
| 2007/0073121 A1 | 3/2007 | Hoarau et al. |
| 2007/0078309 A1* | 4/2007 | Matlock .............. A61B 5/6826 600/310 |
| 2007/0094045 A1 | 4/2007 | Cobbs et al. |
| 2007/0118056 A1 | 5/2007 | Wang et al. |
| 2007/0129769 A1 | 6/2007 | Bourget et al. |
| 2007/0142715 A1 | 6/2007 | Banet et al. |
| 2007/0142730 A1 | 6/2007 | Laermer et al. |
| 2007/0156456 A1 | 7/2007 | McGillin et al. |
| 2007/0161912 A1 | 7/2007 | Zhang et al. |
| 2007/0185393 A1 | 8/2007 | Zhou et al. |
| 2007/0188323 A1 | 8/2007 | Sinclair et al. |
| 2007/0193834 A1 | 8/2007 | Pai et al. |
| 2007/0208233 A1 | 9/2007 | Kovacs |
| 2007/0232867 A1 | 10/2007 | Hansmann |
| 2007/0237719 A1 | 10/2007 | Jones et al. |
| 2007/0244376 A1 | 10/2007 | Wang |
| 2007/0250261 A1 | 10/2007 | Soehren |
| 2007/0252853 A1 | 11/2007 | Park et al. |
| 2007/0255116 A1 | 11/2007 | Mehta et al. |
| 2007/0260487 A1 | 11/2007 | Bartfeld et al. |
| 2007/0265533 A1 | 11/2007 | Tran |
| 2007/0265880 A1 | 11/2007 | Bartfeld et al. |
| 2007/0270671 A1 | 11/2007 | Gal |
| 2007/0276261 A1 | 11/2007 | Banet et al. |
| 2007/0282208 A1 | 12/2007 | Jacobs et al. |
| 2007/0287386 A1 | 12/2007 | Agrawal et al. |
| 2007/0293770 A1 | 12/2007 | Bour et al. |
| 2007/0293781 A1 | 12/2007 | Sims et al. |
| 2008/0004500 A1 | 1/2008 | Cazares et al. |
| 2008/0004507 A1 | 1/2008 | Williams, Jr. et al. |
| 2008/0004904 A1 | 1/2008 | Tran |
| 2008/0027341 A1 | 1/2008 | Sackner et al. |
| 2008/0033255 A1 | 2/2008 | Essenpreis et al. |
| 2008/0039731 A1 | 2/2008 | McCombie et al. |
| 2008/0077026 A1 | 3/2008 | Banet et al. |
| 2008/0077027 A1 | 3/2008 | Allgeyer |
| 2008/0082001 A1 | 4/2008 | Hatlestad et al. |
| 2008/0101160 A1 | 5/2008 | Besson |
| 2008/0103405 A1 | 5/2008 | Banet et al. |
| 2008/0114220 A1 | 5/2008 | Banet et al. |
| 2008/0132106 A1 | 6/2008 | Burnes et al. |
| 2008/0139955 A1 | 6/2008 | Hansmann et al. |
| 2008/0146887 A1 | 6/2008 | Rao et al. |
| 2008/0146892 A1 | 6/2008 | Leboeuf et al. |
| 2008/0161707 A1 | 7/2008 | Farringdon et al. |
| 2008/0162496 A1 | 7/2008 | Postrel |
| 2008/0167535 A1 | 7/2008 | Stivoric et al. |
| 2008/0171927 A1 | 7/2008 | Yang et al. |
| 2008/0194918 A1 | 8/2008 | Kulik et al. |
| 2008/0195735 A1 | 8/2008 | Hodges et al. |
| 2008/0204254 A1 | 8/2008 | Kazuno |
| 2008/0208013 A1 | 8/2008 | Zhang et al. |
| 2008/0208273 A1 | 8/2008 | Owen et al. |
| 2008/0214963 A1 | 9/2008 | Guillemaud et al. |
| 2008/0221399 A1 | 9/2008 | Zhou et al. |
| 2008/0221404 A1 | 9/2008 | Tso |
| 2008/0262362 A1 | 10/2008 | Kolluri et al. |
| 2008/0275349 A1 | 11/2008 | Halperin et al. |
| 2008/0281168 A1 | 11/2008 | Gibson et al. |
| 2008/0281310 A1 | 11/2008 | Dunning et al. |
| 2008/0287751 A1 | 11/2008 | Stivoric et al. |
| 2008/0294019 A1 | 11/2008 | Tran |
| 2008/0319282 A1 | 12/2008 | Tran |
| 2008/0319327 A1 | 12/2008 | Banet et al. |
| 2009/0018408 A1 | 1/2009 | Ouchi et al. |
| 2009/0018409 A1 | 1/2009 | Banet et al. |
| 2009/0018453 A1 | 1/2009 | Banet et al. |
| 2009/0040041 A1 | 2/2009 | Janetis et al. |
| 2009/0054752 A1 | 2/2009 | Jonnalagadda et al. |
| 2009/0069642 A1 | 3/2009 | Gao et al. |
| 2009/0076363 A1 | 3/2009 | Bly et al. |
| 2009/0076397 A1 | 3/2009 | Libbus et al. |
| 2009/0076398 A1 | 3/2009 | Li et al. |
| 2009/0076405 A1 | 3/2009 | Amurthur et al. |
| 2009/0082681 A1 | 3/2009 | Yokoyama et al. |
| 2009/0112072 A1 | 4/2009 | Banet et al. |
| 2009/0112281 A1 | 4/2009 | Miyazawa et al. |
| 2009/0112630 A1 | 4/2009 | Collins, Jr. et al. |
| 2009/0118590 A1 | 5/2009 | Teller et al. |
| 2009/0118626 A1 | 5/2009 | Moon et al. |
| 2009/0131759 A1 | 5/2009 | Sims et al. |
| 2009/0187085 A1 | 7/2009 | Pav |
| 2009/0192366 A1 | 7/2009 | Mensinger et al. |
| 2009/0198139 A1 | 8/2009 | Lewicke et al. |
| 2009/0221937 A1 | 9/2009 | Smith et al. |
| 2009/0222119 A1 | 9/2009 | Plahey et al. |
| 2009/0227877 A1 | 9/2009 | Tran |
| 2009/0233770 A1 | 9/2009 | Vincent et al. |
| 2009/0259113 A1 | 10/2009 | Liu et al. |
| 2009/0262074 A1 | 10/2009 | Nasiri et al. |
| 2009/0264712 A1 | 10/2009 | Baldus et al. |
| 2009/0287067 A1 | 11/2009 | Dorogusker et al. |
| 2009/0295541 A1 | 12/2009 | Roof |
| 2009/0306485 A1 | 12/2009 | Bell |
| 2009/0306487 A1 | 12/2009 | Crowe et al. |
| 2009/0306524 A1 | 12/2009 | Muhlsteff et al. |
| 2009/0312973 A1 | 12/2009 | Hatlestad et al. |
| 2009/0318779 A1 | 12/2009 | Tran |
| 2009/0322513 A1 | 12/2009 | Hwang et al. |
| 2009/0326349 A1 | 12/2009 | McGonigle et al. |

(56) References Cited

U.S. PATENT DOCUMENTS

| | | |
|---|---|---|
| 2010/0010380 A1 | 1/2010 | Panken et al. |
| 2010/0030034 A1 | 2/2010 | Schulhauser et al. |
| 2010/0030085 A1 | 2/2010 | Rojas Ojeda et al. |
| 2010/0056881 A1 | 3/2010 | Libbus et al. |
| 2010/0056886 A1 | 3/2010 | Hurtubise et al. |
| 2010/0113948 A1 | 5/2010 | Yang et al. |
| 2010/0125188 A1 | 5/2010 | Schilling et al. |
| 2010/0130811 A1 | 5/2010 | Leuthardt et al. |
| 2010/0160793 A1 | 6/2010 | Lee et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168531 A1 | 7/2010 | Shaltis et al. |
| 2010/0168589 A1 | 7/2010 | Banet et al. |
| 2010/0210930 A1 | 8/2010 | Saylor |
| 2010/0217099 A1 | 8/2010 | Leboeuf et al. |
| 2010/0222649 A1 | 9/2010 | Schoenberg |
| 2010/0234693 A1 | 9/2010 | Srinivasan et al. |
| 2010/0234695 A1 | 9/2010 | Morris |
| 2010/0234786 A1 | 9/2010 | Fulkerson et al. |
| 2010/0241011 A1 | 9/2010 | McCombie et al. |
| 2010/0280440 A1 | 11/2010 | Skelton et al. |
| 2010/0298650 A1 | 11/2010 | Moon et al. |
| 2010/0298651 A1 | 11/2010 | Moon et al. |
| 2010/0298652 A1 | 11/2010 | McCombie et al. |
| 2010/0298653 A1 | 11/2010 | McCombie et al. |
| 2010/0298654 A1 | 11/2010 | McCombie et al. |
| 2010/0298655 A1 | 11/2010 | McCombie et al. |
| 2010/0298656 A1 | 11/2010 | McCombie et al. |
| 2010/0298657 A1 | 11/2010 | McCombie et al. |
| 2010/0298658 A1 | 11/2010 | McCombie et al. |
| 2010/0298659 A1 | 11/2010 | McCombie et al. |
| 2010/0298660 A1 | 11/2010 | McCombie et al. |
| 2010/0298661 A1 | 11/2010 | McCombie et al. |
| 2010/0298677 A1 | 11/2010 | Lu et al. |
| 2010/0312115 A1 | 12/2010 | Dentinger |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2010/0331640 A1 | 12/2010 | Medina |
| 2011/0066006 A1 | 3/2011 | Banet et al. |
| 2011/0066007 A1 | 3/2011 | Banet et al. |
| 2011/0066008 A1 | 3/2011 | Banet et al. |
| 2011/0066009 A1 | 3/2011 | Moon et al. |
| 2011/0066010 A1 | 3/2011 | Moon et al. |
| 2011/0066037 A1 | 3/2011 | Banet et al. |
| 2011/0066038 A1 | 3/2011 | Banet et al. |
| 2011/0066039 A1 | 3/2011 | Banet et al. |
| 2011/0066043 A1 | 3/2011 | Banet et al. |
| 2011/0066044 A1 | 3/2011 | Moon et al. |
| 2011/0066045 A1 | 3/2011 | Moon et al. |
| 2011/0066050 A1 | 3/2011 | Moon et al. |
| 2011/0066051 A1 | 3/2011 | Moon et al. |
| 2011/0066062 A1 | 3/2011 | Banet et al. |
| 2011/0070829 A1 | 3/2011 | Griffin et al. |
| 2011/0076942 A1 | 3/2011 | Taveau et al. |
| 2011/0093281 A1 | 4/2011 | Plummer et al. |
| 2011/0105862 A1 | 5/2011 | Gies et al. |
| 2011/0144456 A1 | 6/2011 | Muhlsteff et al. |
| 2011/0152632 A1 | 6/2011 | Le Neel et al. |
| 2011/0178375 A1 | 7/2011 | Forster |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0257489 A1 | 10/2011 | Banet et al. |
| 2011/0257551 A1 | 10/2011 | Banet et al. |
| 2011/0257552 A1 | 10/2011 | Banet et al. |
| 2011/0257554 A1 | 10/2011 | Banet et al. |
| 2011/0257555 A1 | 10/2011 | Banet et al. |
| 2011/0275907 A1 | 11/2011 | Inciardi et al. |
| 2012/0065525 A1 | 3/2012 | Douniama et al. |
| 2012/0123232 A1 | 5/2012 | Najarian et al. |

FOREIGN PATENT DOCUMENTS

| | | |
|---|---|---|
| DE | 202006000119 | 3/2006 |
| EP | 0443267 A1 | 8/1991 |
| EP | 0993803 A1 | 4/2000 |
| GB | 2329250 A | 3/1999 |
| WO | 1999032030 A1 | 7/1999 |
| WO | 2006005169 A1 | 1/2006 |
| WO | 2007024777 A2 | 3/2007 |
| WO | WO 2007024777 A2 * | 3/2007 |
| WO | 2007143535 A2 | 12/2007 |
| WO | 2008037820 A1 | 4/2008 |
| WO | 2008110788 A1 | 9/2008 |
| WO | 2009009761 A1 | 1/2009 |
| WO | 2010135516 A2 | 11/2010 |
| WO | 2010135518 A1 | 11/2010 |
| WO | 2010148205 A1 | 12/2010 |
| WO | 2011032132 A2 | 3/2011 |
| WO | 2011034881 A1 | 3/2011 |
| WO | 2011082341 A1 | 7/2011 |
| WO | 2011112782 A1 | 9/2011 |
| WO | 2011133582 A1 | 10/2011 |

OTHER PUBLICATIONS

Non-Final Office Action issued by the US Patent and Trademark Office dated Sep. 14, 2012 in U.S. Appl. No. 12/650,374.

Drinnan et al., Relation between heart rate and pulse transit time during paced respiration. Physiol. Meas. Aug. 2001;22(3):425-432.

Flash et al., The Coordination of Arm Movements: An Experimentally Confirmed Mathematical Model. J Neurosci. Jul. 1985;5(7):1688-1703.

MA and Zhang, A Correlation Study on the Variabilities in Pulse Transit Time, Blood Pressure, and Heart Rate Recorded Simultaneously from Healthy Subjects. Conf Proc IEEE Eng Med Biol Soc. 2005;1:996-999.

Non-Final Office Action issued by the US Patent and Trademark Office dated Sep. 17, 2012 in U.S. Appl. No. 12/469,192.

Gallagher, Comparison of Radial and Femoral Arterial Blood Pressure in Children after Cardiopulmonary Bypass. J Clin Monit. Jul. 1985;1(3):168-171.

Park et al., Direct Blood Pressure Measurements in Brachial and Femoral Arteries in Children. Circulation Feb. 1970;41(2):231-237.

Non-Final Office Action issued by the US Patent and Trademark Office dated Sep. 26, 2012 in U.S. Appl. No. 12/560,104.

Packet Definition. The Linux Information Project Jan. 8, 2006 http://www.linfo.org/packet.html.

RS-232. Wikipedia Dec. 5, 2008 http:l/web.archive.org/web/20081205160754/http://!en.wikipedia.org/wiki/RS-232.

Non-Final Office Action issued by the US Patent and Trademark Office dated Oct. 9, 2012 in U.S. Appl. No. 12/762,726.

Final Office Action issued by the US Patent and Trademark Office dated Oct. 22, 2012 in U.S. Appl. No. 12/762,822.

Final Office Action issued by the US Patent and Trademark Office dated Oct. 25, 2012 in U.S. Appl. No. 12/599,426.

Alves et al., CAN Protocol: A Laboratory Prototype for Fieldbus Applications. XIX IMEKO World Congress Fundamental and Applied Metrology Sep. 6-11, 2009, Lisbon, Portugal. 4 pages :454-457 ISBN 978-963-88410-0-1.

Benefits of Digital Sensors. Gems Sensors. Feb. 14, 2008. http://web.archive.org/web/20080214122230/http://www.sensorland.com/HowPage054.html.

Final Office Action issued by the US Patent and Trademark Office dated Oct. 25, 2012 in U.S. Appl. No. 12/762,790.

(56) References Cited

OTHER PUBLICATIONS

Non-Final Office Action issued by the US Patent and Trademark Office dated Oct. 30, 2012 in U.S. Appl. No. 12/559,386.
Non-Final Office Action issued by the US Patent and Trademark Office dated Nov. 6, 2012 in U.S. Appl. No. 12/559,379.
Non-Final Office Action issued by the US Patent and Trademark Office dated Nov. 6, 2012 in U.S. Appl. No. 12/650,370.
Poon and Zhang, Cuff-Less and Noninvasive Measurements of Arterial Blood Pressure by Pulse Transit Time. Conf Proc IEEE Eng Med Biol Soc. 2005;6:5877-5880.
Non-Final Office Action issued by the US Patent and Trademark Office dated Nov. 7, 2012 in U.S. Appl. No. 12/559,392.
Allen et al., Classification of a known sequence of motions and postures from accelerometry data using adapted Gaussian mixture models. Physiol. Meas. 2006;27:935-951.
Asada et al., Active Noise Cancellation Using MEMS Accelerometers for Motion-Tolerant Wearable Bio-Sensors. Proceedings of the 26th Annual International Conference of the IEEE EMBS. San Francisco, CA, USA. Sep. 1-5, 2004:2157-2160.
Bowers et al., Respiratory Rate Derived from Principal Component Analysis of Single Lead Electrocardiogram. Computers in Cardiology Conference Proceedings Sep. 2008;35:437-440.
Bussmann et al., Measuring daily behavior using ambulatory accelerometry: The Activity Monitor. Behav Res Methods Instrum Comput. Aug. 2001;33(3):349-356.
Cretikos et al., The Objective Medical Emergency Team Activation Criteria: a case-control study. Resuscitation Apr. 2007;73(1):62-72.
Espina et al., Wireless Body Sensor Network for Continuous Cuff-less Blood Pressure Monitoring. Proceedings of the 3rd IEEE-EMBS. International Summer School and Symposium on Medical Devices and Biosensors. MIT, Boston, USA, Sep. 4-6, 2006:11-15.
Fieselmann et al., Respiratory rate predicts cardiopulmonary arrest for internal medicine patients. J Gen Intern Med Jul. 1993;8(7):354-360.
Goldhill et al., A physiologically-based early warning score for ward patients: the association between score and outcome. Anaesthesia Jun. 2005;60(6):547-553.
Hung et al., Estimation of Respiratory Waveform Using an Accelerometer. 5th IEEE International Symposium on Biomedical Imaging: From Nano to Macro, May 14-17, 2008:1493-1496.
Jin, A Respiration Monitoring System Based on a Tri-Axial Accelerometer and an Air-Coupled Microphone. Technische Universiteit Eindhoven, University of Technology. Master's Graduation Paper, Electrical Engineering Aug. 25, 2009.
Karantonis et al., Implementation of a Real-Time Human Movement Classifier Using a Triaxial Accelerometer for Ambulatory Monitoring. IEEE Transactions on Information Technology in Biomedicine. Jan. 2006;10(1):156-167.
Khambete et al., Movement artefact rejection in impedance pneumography using six strategically placed electrodes. Physiol. Meas. 2000;21:79-88.
Khan et al., Accelerometer Signal-based Human Activity Recognition Using Augmented Autoregressive Model Coefficients and Artificial w Neural Nets. 30th Annual International Conference of the IEEE Engineering in Medicine and Biology Society. Aug. 20-24, 2008:5172-5175.
Mason, Signal Processing Methods for Non-Invasive Respiration Monitoring. Department of Engineering Science, University of Oxford 2002.
Mathie et al., Classification of basic daily movements using a triaxial accelerometer. Med Biol Eng Comput. Sep. 2004;42(5):679-687.
Otto et al., System Architecture of a Wireless Body Area Sensor Network for Ubiquitous Health Monitoring. Journal of Mobile Multimedia Jan. 10, 2006;1(4):307-326.
Park et al., An improved algorithm for respiration signal extraction from electrocardiogram measured by conductive textile electrodes using instantaneous frequency estimation. Med Bio Eng Comput 2008;46:147-158.

PDF-Pro for iPhone & iPod touch User Manual. ePapyrus Jul. 2009;1:1-25 http://epapyrus.com/en/files/PDFPro%.
Seo et al., Performance Improvement of Pulse Oximetry-Based Respiration Detection by Selective Mode Bandpass Filtering. Ergonomics and Health Aspects of Work with Computers Lecture Notes in Computer Science, 2007;4566:300-308.
Soh et al., An investigation of respiration while wearing back belts. Applied Ergonomics 1997; 28(3):189-192.
Subbe et al., Effect of introducing the Modified Early Warning score on clinical outcomes, cardiopulmonary arrests and intensive care utilization in acute medical admissions. Anaesthesia Aug. 2003;58(8):797-802.
Vuorela et al., Two portable long-term measurement devices for ECG and bioimpedance. Second International Conference on Pervasive Computing Technologies for Healthcare.. Jan. 30, 2008-Feb. 1: 169-172.
Wolf et al., Development of a Fall Detector and Classifier based on a Triaxial Accelerometer Demo Board. 2007:210-213.
Non-Final Office Action issued by the US Patent and Trademark Office dated Apr. 30, 2012 in U.S. Appl. No. 12/762,790.
Non-Final Office Action issued by the US Patent and Trademark Office dated Mar. 30, 2012 in U.S. Appl. No. 12/469,236.
Non-Final Office Action issued by the US Patent and Trademark Office dated Apr. 3, 2012 in U.S. Appl. No. 12/469,094.
Restriction Requirement issued by the US Patent and Trademark Office dated Feb. 2, 2012 in U.S. Appl. No. 12/469,222.
Non-Final Office Action issued by the US Patent and Trademark Office dated Mar. 27, 2012 in U.S. Appl. No. 12/559,426.
Non-Final Office Action issued by the US Patent and Trademark Office dated Apr. 3, 2012 in U.S. Appl. No. 12/559,039.
Non-Final Office Action issued by the US Patent and Trademark Office dated Dec. 29, 2011 in U.S. Appl. No. 12/559,080.
Response to Non-Final Office Action dated Mar. 19, 2012 in U.S. Appl. No. 12/559,080.
Notice of Allowance issued by the US Patent and Trademark Office dated Apr. 2, 2012 in U.S. Appl. No. 12/559,080.
Non-Final Office Action issued by the US Patent and Trademark Office dated Dec. 15, 2011 in U.S. Appl. No. 12/560,077.
Non-Final Office Action issued by the US Patent and Trademark Office dated Mar. 8, 2012 in U.S. Appl. No. 12/560,093.
Restriction Requirement issued by the US Patent and Trademark Office dated Dec. 14, 2012 in U.S. Appl. No. 12/560,093.
Response to Restriction Requirement dated Feb. 15, 2012 in U.S. Appl. No. 12/560,093.
Non-Final Office Action issued by the US Patent and Trademark Office dated Mar. 1, 2012 in U.S. Appl. No. 12/560,104.
Restriction Requirement issued by the US Patent and Trademark Office dated Jan. 19, 2012 in U.S. Appl. No. 12/469,115.
Response to Restriction Requirement dated Feb. 15, 2012 in U.S. Appl. No. 12/469,115.
Restriction Requirement issued by the US Patent and Trademark Office dated Nov. 14, 2011 in U.S. Appl. No. 12/469,127.
Response to Restriction Requirement dated Feb. 15, 2012 in U.S. Appl. No. 12/469,127.
Non-Final Office Action issued by the US Patent and Trademark Office dated Mar. 9, 2012 in U.S. Appl. No. 12/469,127.
Non-Final Office Action issued by the US Patent and Trademark Office dated Apr. 3, 2012 in U.S. Appl. No. 12/469,137.
International Preliminary Report on Patentability dated Dec. 1, 2011 issued in PCT/US2010/035554.
International Search Report and Written Opinion dated Sep. 23, 2010 issued in PCT/US2010/035554.
International Preliminary Report on Patentability dated Jan. 5, 2012 issued in PCT/US2010/039000.
International Search Report and Written Opinion dated Sep. 7, 2010 issued in PCT/US2010/039000.
International Search Report and Written Opinion dated Nov. 3, 2010 issued in PCT/US2010/048729.
International Search Report and Written Opinion dated Nov. 5, 2010 issued in PCT/US2010/048866.
International Search Report and Written Opinion dated Mar. 3, 2011 issued in PCT/US2010/062564.

(56) References Cited

OTHER PUBLICATIONS

International Search Report and Written Opinion dated Jul. 22, 2011 issued in PCT/US2011/027843.
International Search Report and Written Opinion dated Jul. 20, 2011 issued in PCT/US2011/033100.
Non-Final Office Action issued by the US Patent and Trademark Office dated May 26, 2011 in U.S. Appl. No. 12/469,151.
Response to Non-Final Office Action dated Nov. 25, 2011 in U.S. Appl. No. 12/469,151.
Notice of Allowance issued by the US Patent and Trademark Office dated Feb. 1, 2012 in U.S. Appl. No. 12/469,151.
Non-Final Office Action issued by the US Patent and Trademark Office dated Aug. 4, 2011 in U.S. Appl. No. 12/469,182.
Response to Non-Final Office Action dated Nov. 25, 2011 in U.S. Appl. No. 12/469,182.
Notice of Allowance issued by the US Patent and Trademark Office dated Dec. 28, 2011 in U.S. Appl. No. 12/469,182.
International Search Report and Written Opinion dated Oct. 15, 2010 issued in PCT/US2010/035550.
Non-Final Office Action issued by the US Patent and Trademark Office dated Apr. 12, 2012 in U.S. Appl. No. 12/559,429.
Non-Final Office Action issued by the US Patent and Trademark Office dated Apr. 12, 2012 in U.S. Appl. No. 12/559,430.
Non-Final Office Action issued by the US Patent and Trademark Office dated Apr. 24, 2012 in U.S. Appl. No. 12/559,435.
Non-Final Office Action issued by the US Patent and Trademark Office dated Apr. 25, 2012 in U.S. Appl. No. 12/762,733.
Non-Final Office Action issued by the US Patent and Trademark Office dated Apr. 27, 2012 in U.S. Appl. No. 12/762,822.
Non-Final Office Action issued by the US Patent and Trademark Office dated Mar. 27, 2012 in U.S. Appl. No. 12/559,422.
Mathie, Monitoring and Interpreting Human Movement Patterns using a Triaxial Accelerometer. Faculty of Engineering. The University of New South Wales. PhD Dissertation. Aug. 2003: part1 pp. 1-256.
Mathie, Monitoring and Interpreting Human Movement Patterns using a Triaxial Accelerometer. Faculty of Engineering. The University of New South Wales. PhD Dissertation. Aug. 2003: part2 pp. 256-512.
International Search Report and Written Opinion dated Apr. 27, 2012 as reported in PCT/US2011/067441.
Non-Final Office Action issued by the US Patent and Trademark Office dated May 7, 2012 in U.S. Appl. No. 12/469,115.
Non-Final Office Action issued by the US Patent and Trademark Office dated May 9, 2012 in U.S. Appl. No. 12/762,836.
Non-Final Office Action issued by the US Patent and Trademark Office dated May 10, 2012 in U.S. Appl. No. 12/559,419.
Jackson, Digital Filter Design and Synthesis Using High-Level Modeling Tools. Virginia Polytechnic Institute and State University Thesis. Dec. 1999.
Kim et al., Two Algorithms for Detecting Respiratory Rate from ECG Signal. IFMBE Proceedings 2007;14(6)JC27:4069-4071.
O'Haver, Peak Finding and Measurement, Version 1.6 Oct. 26, 2006. http://web.archive.org/web/20090205162604/http://terpconnect.umd.edu/-toh/spectrum/PeakFindingandMeasurement.htm.
Reinvuo et al., Measurement of Respiratory Rate with High-Resolution Accelerometer and EMFit Pressure Sensor. Proceedings of the 2006 IEEE Sensors Applications Symposium Feb. 7-9, 2006:192-195.
Non-Final Office Action issued by the US Patent and Trademark Office dated May 11, 2012 in U.S. Appl. No. 12/762,846.
Non-Final Office Action issued by the US Patent and Trademark Office dated May 11, 2012 in U.S. Appl. No. 12/762,874.
Non-Final Office Action issued by the US Patent and Trademark Office dated Jun. 11, 2012 in U.S. Appl. No. 12/469,222.
Non-Final Office Action issued by the US Patent and Trademark Office dated Jun. 8, 2012 in U.S. Appl. No. 12/650,383.
Non-Final Office Action issued by the US Patent and Trademark Office dated Jun. 8, 2012 in U.S. Appl. No. 12/650,392.
Non-Final Office Action issued by the US Patent and Trademark Office dated Jun. 20, 2012 in U.S. Appl. No. 12/762,751.
International Search Report and Written Opinion dated Jun. 29, 2012 issued in PCT/US2012/025640.
Non-Final Office Action issued by the US Patent and Trademark Office dated Jul. 5, 2012 in U.S. Appl. No. 12/560,138.
"Signal Strength." Oct. 6, 2008. http://web.archive.org/web/20081006200523/http://!en.wikipedia.org/wiki/Signal_strength.
Non-Final Office Action issued by the US Patent and Trademark Office dated May 24, 2012 in U.S. Appl. No. 12/560,111.
Restriction Requirement issued by the US Patent and Trademark Office dated Apr. 24, 2012 in U.S. Appl. No. 12/469,107.
Response to Restriction Requirement dated Jun. 14, 2012 in U.S. Appl. No. 12/469,107.
Non-Final Office Action issued by the US Patent and Trademark Office dated Jul. 18, 2012 in U.S. Appl. No. 12/650,389.
Chan et al., Noninvasive and Cuffless Measurements of Blood Pressure For Telemedicine. Proceedings of the 23rd Annual International Conference of the IEEE Engineering in Medicine and Biology Society 2001:3 pages.
Fung, Advisory System for Administration of Phenylephrine Following Spinal Anesthesia for Cesarean Section. Master's Thesis. University of British Columbia 2002: 119 pages.
Liu et al., The Changes in Pulse Transit Time at Specific Cuff Pressures during Inflation and Deflation. Proceedings of the 28th IEEE EMBS Annual International Conference New York City, USA, Aug. 30, 2006-Sep. 3:6404-6405.
Nitzan et al., Effects of External Pressure on Arteries Distal to the Cuff During Sphygmomanometry. IEEE Transactions on Biomedical Engineering, Jun. 2005;52(6):1120-1127.
USB 2.0 Specification Engineering Change Notice. Oct. 20, 2000.
Yan and Zhang, A Novel Calibration Method for Noninvasive Blood Pressure Measurement Using Pulse Transit Time. Proceedings of the 4th IEEE-EMBS International Summer School and Symposium on Medical Devices and Biosensors St Catharine's College, Cambridge, UK, Aug. 19-22, 2007.
Zislin et al., Ways of Improving the Accuracy of Arterial Pressure Oscillometry. Biomedical Engineering 2005;39(4):174-178.
International Search Report and Written Opinion dated May 29, 2012 issued in PCT/US2012/025648.
Non-Final Office Action issued by the US Patent and Trademark Office dated Aug. 3, 2012 in U.S. Appl. No. 12/762,925.
Non-Final Office Action issued by the US Patent and Trademark Office dated Aug. 3, 2012 in U.S. Appl. No. 12/762,963.
Non-Final Office Action issued by the US Patent and Trademark Office dated Aug. 20, 2012 in U.S. Appl. No. 12/762,777.
Non-Final Office Action issued by the US Patent and Trademark Office dated Aug. 21, 2012 in U.S. Appl. No. 12/469,107.
Non-Final Office Action issued by the US Patent and Trademark Office dated Aug. 24, 2012 in U.S. Appl. No. 12/762,936.
Booker, R., "Pulse Oximetry", Art & Science Clinical Skills:43. 22(30):39-41, 2008.
Talkowski, Quantifying Physical Activity in Community Dwelling Older Adults Using Accelerometry, University of Pittsburgh (Dissertation) 2008:1-91.
Final Office Action issued by the United States Patent and Trademark Office in U.S. Appl. No. 12/469,236 dated Jul. 8, 2013.
Non-Final Office Action issued by the United States Patent and Trademark Office in U.S. Appl. No. 12/560,111 dated Jul. 8, 2013.
Scanaill et al., A Review of Approaches to Mobility Telemonitoring of the Elderly in Their Living Environment. Annals of Biomed Engineer. Apr. 2006;34(4):547-563.
Notice of Allowance issued by the United States Patent and Trademark Office in U.S. Appl. No. 12/762,733 dated Jul. 24, 2013.
Final Office Action issued by the United States Patent and Trademark Office in U.S. Appl. No. 12/762,944 dated Aug. 2, 2013.
Response to Office Action issued by the United States Patent and Trademark Office in U.S. Appl. No. 12/559,039 dated Aug. 9, 2013.
Sifil et al., Evaluation of the Harmonized Alert Sensing Technology Device for Hemodynamic Monitoring in Chronic Hemodialysis Patients. ASAIO J. Nov.-Dec. 2003;49(6):667-672.

(56) References Cited

OTHER PUBLICATIONS

Weinhold et al., Buprenorphine alone and in combination with naloxone in non-dependent humans. Drug Alcohol Depend. Aug. 1992;30(3):263-274.
Final Office Action issued by the United States Patent and Trademark Office in U.S. Appl. No. 12/762,726 dated Aug. 15, 2013.
Extended European Search Report and Written Opinion issued in application No. EP 10817733 dated Aug. 29, 2013.
Extended European Search Report and Written Opinion issued in application No. EP 08770884 dated Sep. 17, 2013.
DuPont Engineering Polymers, "General Design Principles—Module 1", Mar. 2002, pp. 1-153.
Non-Final Office Action issued by the US Patent and Trademark Office dated Aug. 30, 2012 in U.S. Appl. No. 12/469,202.
Non-Final Office Action issued by the US Patent and Trademark Office dated Sep. 17, 2012 in U.S. Appl. No. 12/650,354.
Non-Final Office Action issued by the US Patent and Trademark Office dated Sep. 21, 2012 in U.S. Appl. No. 12/469,115.
Response to Non-Final Office Action issued in U.S. Appl. No. 12/469,236 dated Sep. 27, 2012.
Response to Non-Final Office Action issued in U.S. Appl. No. 12/487,283 dated Sep. 27, 2012.
Non-Final Office Action issued by the US Patent and Trademark Office dated Sep. 28, 2012 in U.S. Appl. No. 12/560,087.
Response to Non-Final Office Action issued in U.S. Appl. No. 12/762,836 dated Oct. 9, 2012.
Response to Non-Final Office Action issued in U.S. Appl. No. 12/559,429 dated Oct. 12, 2012.
Response to Non-Final Office Action issued in U.S. Appl. No. 12/559,430 dated Oct. 12, 2012.
Response to Non-Final Office Action issued in U.S. Appl. No. 12/559,435 dated Oct. 23, 2012.
Final Office Action issued by the US Patent and Trademark Office dated Oct. 24, 2012 in U.S. Appl. No. 12/599,429.
Final Office Action issued by the US Patent and Trademark Office dated Oct. 24, 2012 in U.S. Appl. No. 12/599,430.
Non-Final Office Action issued by the US Patent and Trademark Office dated Oct. 23, 2012 in U.S. Appl. No. 12/762,944.
Response to Non-Final Office Action issued in U.S. Appl. No. 12/762,733 dated Oct. 25, 2012.
Final Office Action issued by the US Patent and Trademark Office dated Oct. 26, 2012 in U.S. Appl. No. 12/762,836.
Non-Final Office Action issued by the US Patent and Trademark Office dated Oct. 24, 2012 in U.S. Appl. No. 12/559,403.
Non Final Office Action issued by the United States Patent and Trademark Office in U.S. Appl. No. 12/559,413 dated Nov. 9, 2012.
Response to Office Action issued in U.S. Appl. No. 12/762,846 dated Nov. 13, 2012.
Response to Office Action issued in U.S. Appl. No. 12/762,874 dated Nov. 13, 2012.
Response to Office Action issued in U.S. Appl. No. 12/560,111 dated Nov. 26, 2012.
Response to Office Action issued in U.S. Appl. No. 11/930,881 dated Nov. 26, 2012.
Final Rejection issued by the United States Patent and Trademark Office in U.S. Appl. No. 12/559,419 dated Nov. 16, 2012.
Non Final Office Action issued by the United States Patent and Trademark Office in U.S. Appl. No. 12/559,408 dated Nov. 23, 2012.
Response to Office Action issued in U.S. Appl. No. 12/138,199 dated Nov. 29, 2012.
Response to Office Action issued in U.S. Appl. No. 12/650,383 dated Dec. 7, 2012.
Response to Office Action issued in U.S. Appl. No. 12/650,392 dated Dec. 7, 2012.
Final Rejection issued by the United States Patent and Trademark Office in U.S. Appl. No. 12/559,435 dated Dec. 12, 2012.
Final Rejection issued by the United States Patent and Trademark Office in U.S. Appl. No. 12/560,111 dated Dec. 12, 2012.
Clifford et al., Measuring Tilt with Low-g Accelerometers. Freescale Semiconductor, Inc., 2005:8 pages.
McKneely et al., Plug-and-Play and Network-Capable Medical Instrumentation and Database with a Complete Healthcare Technology Suite: MediCAN. Joint Workshop on High Confidence Medical Devices, Software, and Systems and Medical Device Plug-and-Play Interoperability. 2007:122-129.
Montgomery et al., Lifeguard—A Personal Physiological Monitor For Extreme Environments. Conf Proc IEEE Eng Med Biol Soc. 2004;3:2192-2195.
Thongpithoonrat et al., Networking and Plug-and-Play of Bedside Medical Instruments. Conf Proc IEEE Eng Med Biol Soc. 2008;2008:1514-1517.
Yang et al., Research on Multi-Parameter Physiological Monitor Based on CAN Bus. IFMBE Proceed. 2008;19:417-419.
Zeltwanger, Controller Area Network and CANopen in Medical Equipment. Bus Briefing: Med Dev Manuf Technol. 2002:34-37.
Zitzmann and Schumann, Interoperable Medical Devices Due to Standardized CANopen Interfaces. Joint Workshop on High Confidence Medical Devices, Software, and Systems and Medical Device Plug-and-Play Interoperability. 2007:97-103.
Non Final Office Action issued by the United States Patent and Trademark Office in U.S. Appl. No. 13/432,976 dated Dec. 14, 2012.
Final Rejection issued by the United States Patent and Trademark Office in U.S. Appl. No. 12/762,733 dated Dec. 20, 2012.
Final Rejection issued by the United States Patent and Trademark Office in U.S. Appl. No. 12/762,846 dated Dec. 20, 2012.
Final Rejection issued by the United States Patent and Trademark Office in U.S. Appl. No. 12/650,392 dated Jan. 3, 2013.
Non Final Office Action issued by the United States Patent and Trademark Office in U.S. Appl. No. 13/292,923 dated Jan. 14, 2013.
Copy of Non Final Office Action issued by the United States Patent and Trademark Office in U.S. Appl. No. 13/292,923 on Jan. 14, 2013.
Notice of Allowance issued by the United States Patent and Trademark Office in U.S. Appl. No. 11/470,708 dated Jan. 18, 2013.
International Search Report and Written Opinion issued in PCT/US2012/064302 dated Jan. 15, 2013.
Supplemental European Search Report issued in EP 10778376 dated Jan. 31, 2013.
Final Office Action issued by the United States Patent and Trademark Office in U.S. Appl. No. 12/559,039 dated Feb. 11, 2013.
Reddan et al., Intradialytic Blood Volume Monitoring in Ambulatory Hemodialysis Patients: A Randomized Trial. J Am Soc Nephrol. Jul. 2005;16(7):2162-2169.
Final Office Action issued by the United States Patent and Trademark Office in U.S. Appl. No. 12/469,222 dated Feb. 13, 2013.
Non Final Office Action issued by the United States Patent and Trademark Office in U.S. Appl. No. 12/650,383 dated Feb. 15, 2013.
Non Final Office Action issued by the United States Patent and Trademark Office in U.S. Appl. No. 13/346,408 dated Feb. 25, 2013.
Final Office Action issued by the United States Patent and Trademark Office in U.S. Appl. No. 12/650,389 dated Mar. 14, 2013.
Klabunde, Mean Arterial Pressure. Cardiovascular Physiology Concepts. Mar. 8, 2007.http://web.archive.org/web/20070308182914/http://www.cvphysiology.com/Blood%20Pressure/BP006.htm.
Final Office Action issued by the United States Patent and Trademark Office in U.S. Appl. No. 12/762,874 dated Mar. 14, 2013.
Non Final Office Action issued by the United States Patent and Trademark Office in U.S. Appl. No. 13/196,326 dated Mar. 22, 2013.
De Scalzi et al., Relationship Between Systolic Time Intervals and Arterial Blood Pressure. Clin Cardiol. 1986;9:545-549.
Ahlstrom et al., Noninvasive investigation of blood pressure changes using the pulse wave transit time: a novel approach in the monitoring of hemodialysis patients. J Artif Organs. 2005;8(3):192-197.
Final Office Action issued by the United States Patent and Trademark Office in U.S. Appl. No. 12/762,751 dated Mar. 29, 2013.
Extended European Search Report and Written Opinion issued in EP 12848585 dated Jul. 16, 2015.
Office Action and Search Report issued by SIPO in PRC application No. 2012800657084 dated Jun. 24, 2015.

(56) References Cited

OTHER PUBLICATIONS

Office Action issued by the USPTO in U.S. Appl. No. 12/487,283 dated Sep. 22, 2017—17 pages.
Decision on Appeal issued on May 9, 2018, in Appeal No. 2016-002435, U.S. Appl. No. 12/559,392, First Named Inventor Jim Moon (8 pages).
Record of Oral Hearing issued on May 10, 2018, in Appeal No. 2016-002435, U.S. Appl. No. 12/559,392, First Named Inventor Jim Moon (15 pages).
Office Action issued by the USPTO in U.S. Appl. No. 12/487,283 dated Jan. 4, 2019 (22 pages).

\* cited by examiner

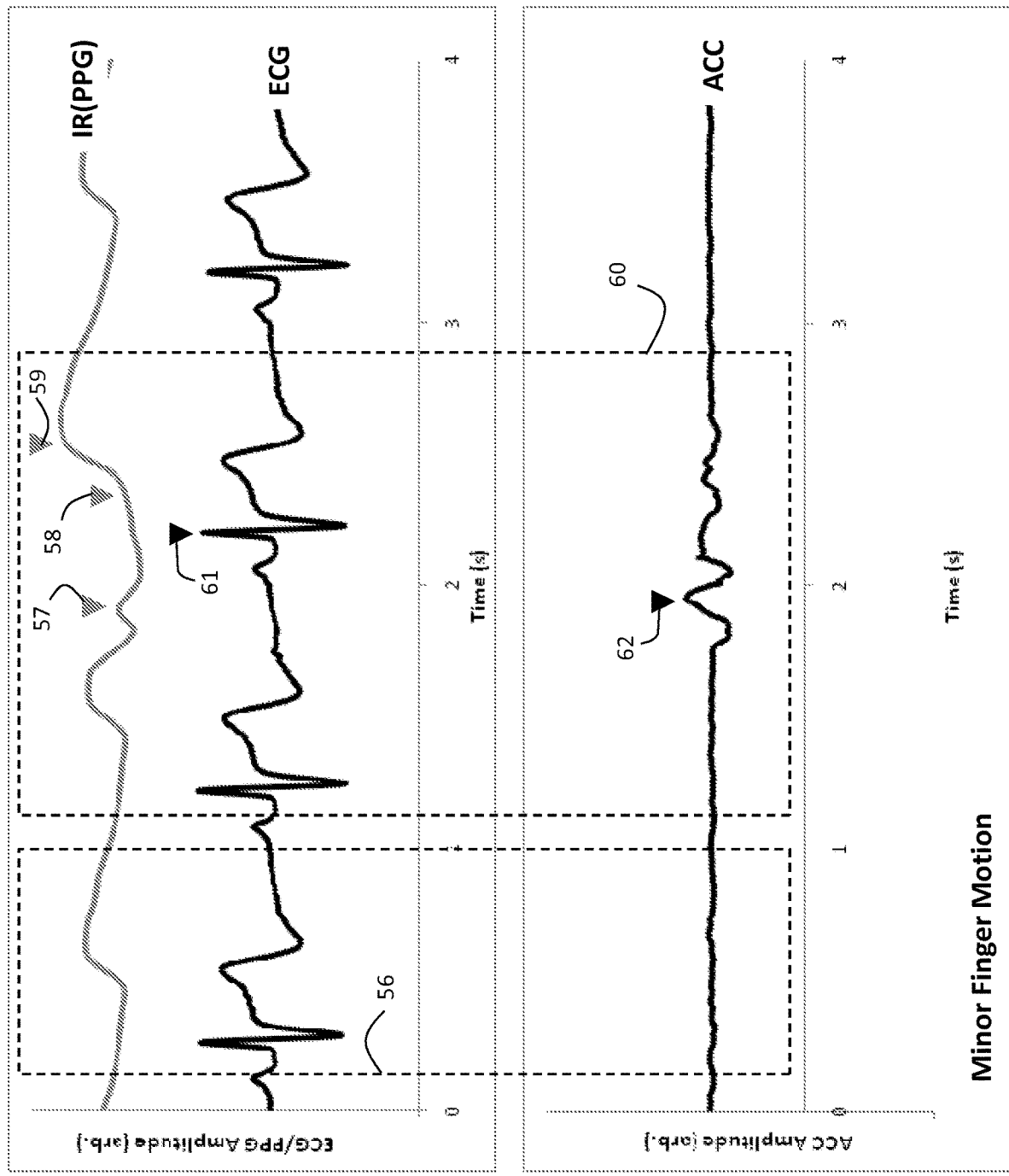

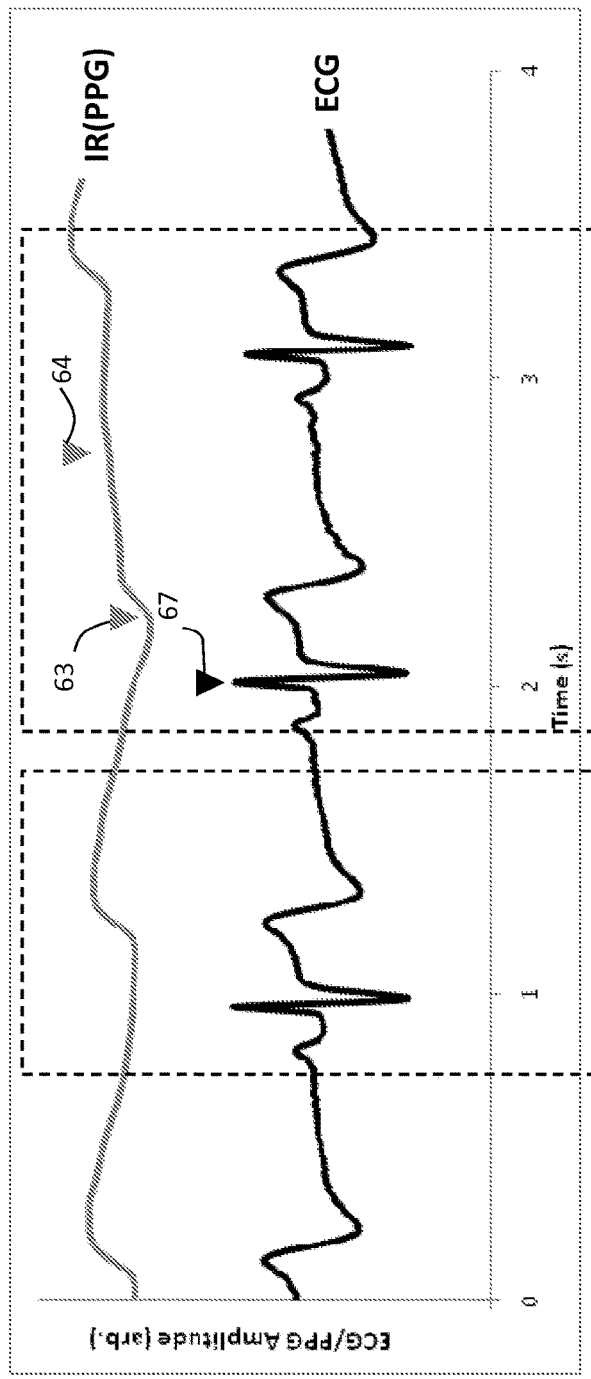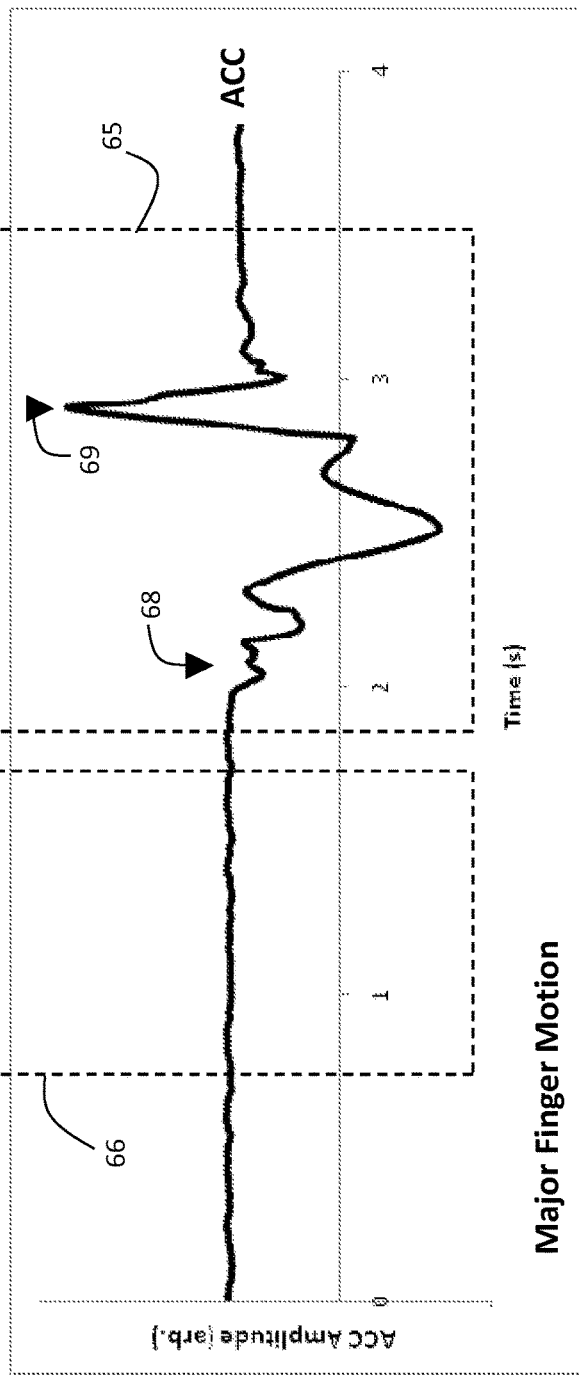
Fig. 11A
Fig. 11B
Major Finger Motion

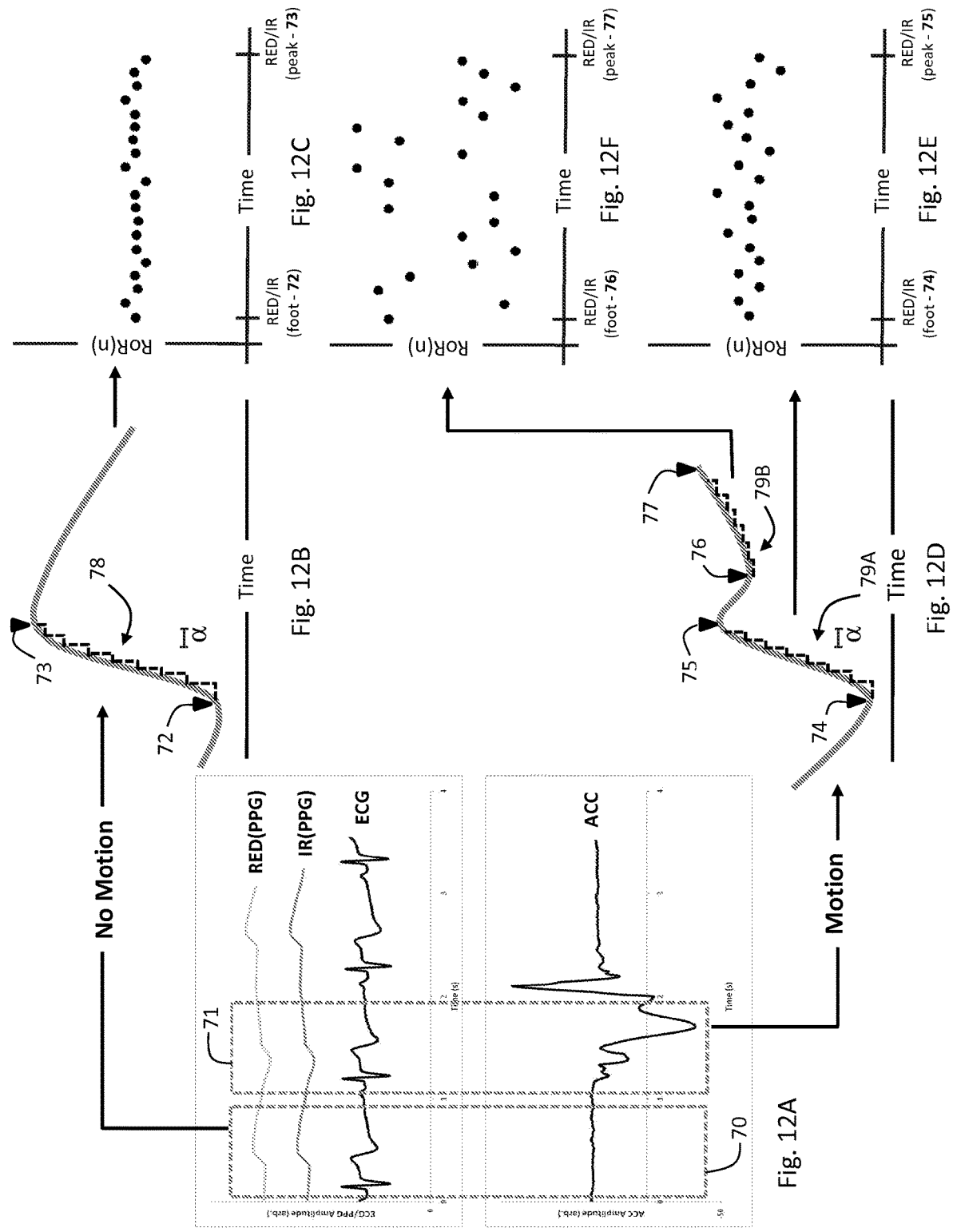

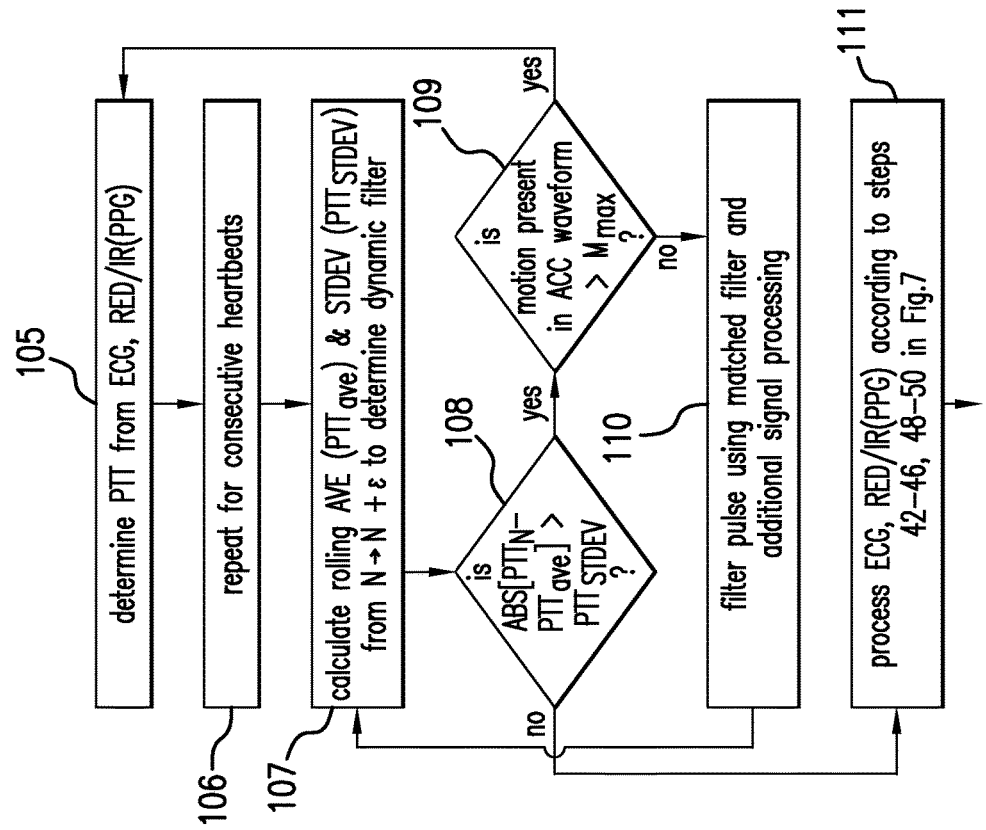
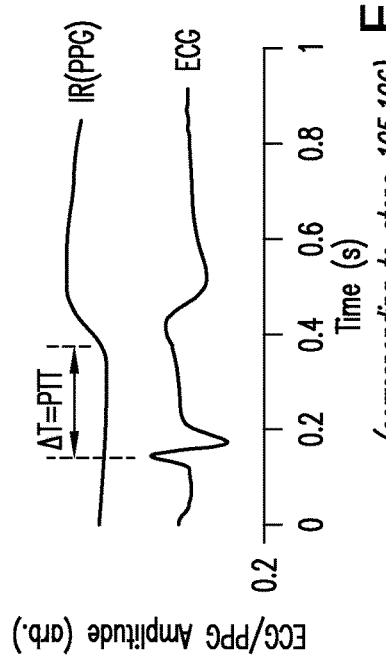
Fig. 13A
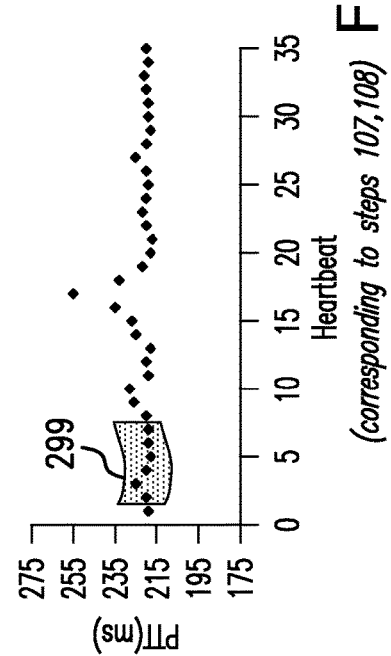
Fig. 13B
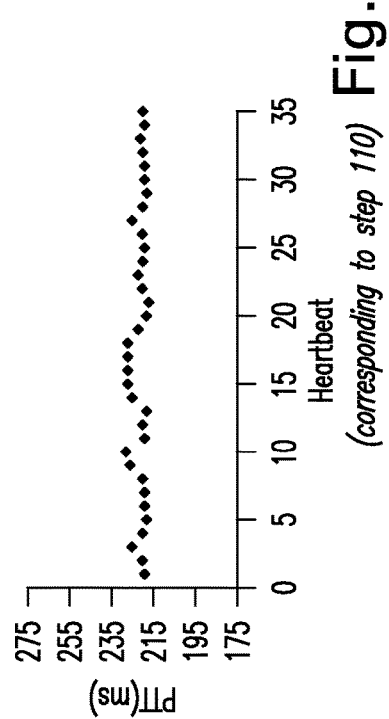
Fig. 13C

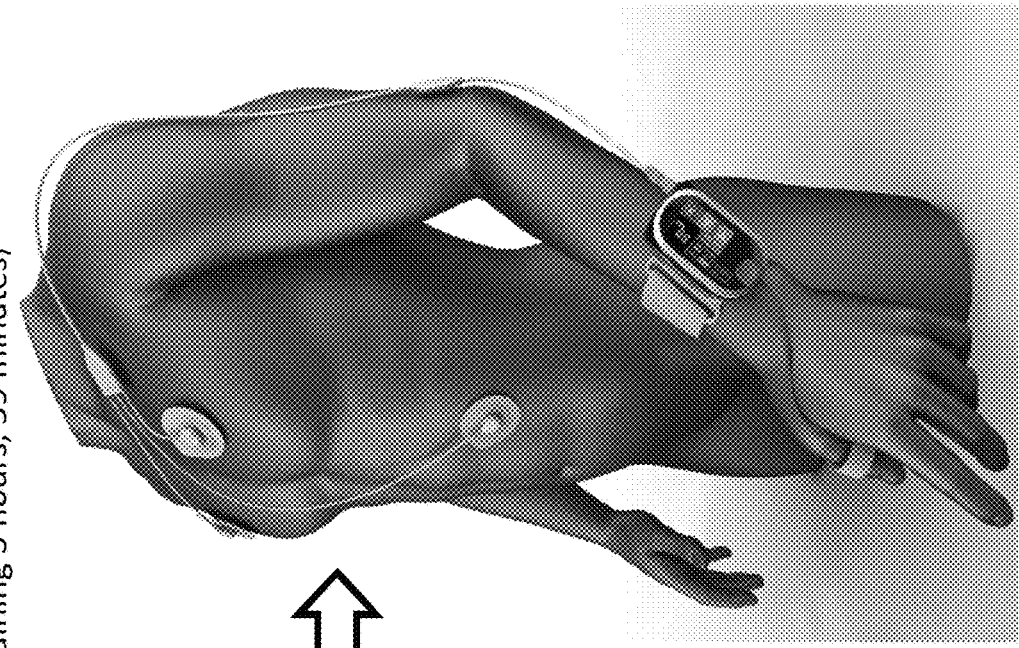
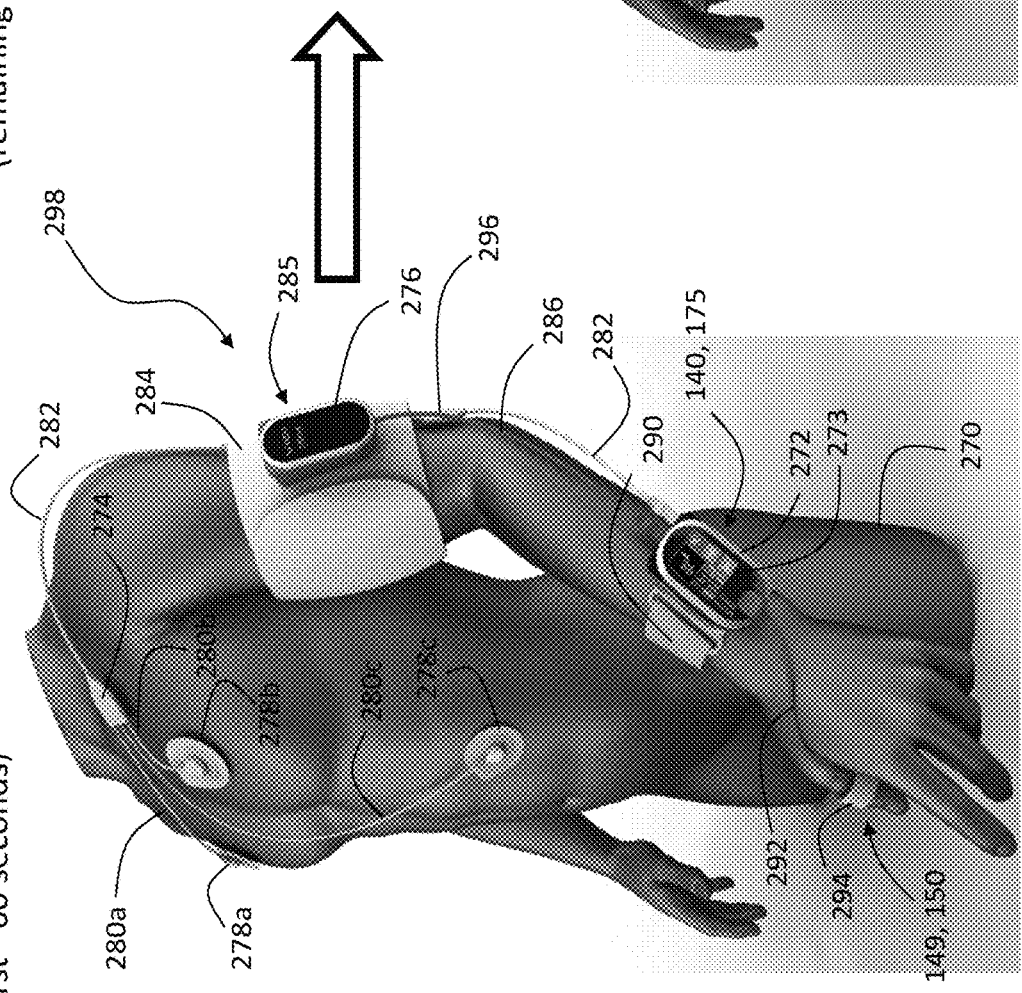
FIG. 23A
FIG. 23B

OPTICAL SENSORS FOR USE IN VITAL SIGN MONITORING

CROSS REFERENCES TO RELATED APPLICATIONS

This application is a continuation-in-part of U.S. patent application Ser. No. 12/171,886, filed Jul. 11, 2008, which claims priority to U.S. Provisional Application No. 60/949,052, filed Jul. 11, 2007; and also a continuation-in-part of U.S. patent application Ser. No. 12/138,194, filed Jun. 12, 2008, which claims priority to U.S. Provisional Application No. 60/943,464, filed Jun. 12, 2007 and U.S. Provisional Application No. 60/983,198, filed Oct. 28, 2007; and also a continuation-in-part of U.S. patent application Ser. No. 12/487,283, filed Jun. 18, 2009, which claims priority to U.S. Provisional Application No. 61/073,681, filed Jun. 18, 2008; and also a continuation-in-part of U.S. patent application Ser. No. 12/650,374, filed Dec. 30, 2009, which is a CIP of U.S. patent application Ser. No. 12/138,194, filed Jun. 12, 2008, which claims priority to U.S. Provisional Application No. 60/943,464, filed Jun. 12, 2007 and U.S. Provisional Application No. 60/983,198, filed Oct. 28, 2007; and also a continuation-in-part of U.S. patent application Ser. No. 12/559,413, filed Sep. 14, 2009, which claims priority to U.S. Provisional Application No. 61/218,055, filed Jun. 17, 2009, and U.S. Provisional Application No. 61/218,057, filed Jun. 17, 2009, and U.S. Provisional Application No. 61/218,059, filed Jun. 17, 2009, and U.S. Provisional Application No. 61/218,060, filed Jun. 17, 2009, and U.S. Provisional Application No. 61/218,061, filed Jun. 17, 2009, and U.S. Provisional Application No. 61/218,062, filed Jun. 17, 2009; each of which is incorporated herein by reference in its entirety, including all tables, figures, and claims.

BACKGROUND OF THE INVENTION

1. Field of the Invention

The present invention relates to medical devices for monitoring vital signs, e.g., saturation of peripheral oxygen, or SpO2.

2. Description of the Related Art

SpO2, sometimes referred to as the 'fifth vital sign', represents a patient's blood oxygen saturation. Medical professionals can detect hypoxemia, i.e. a deficiency of oxygen, by monitoring a patient's SpO2. Values between about 95-100% are considered normal; those below this indicate hypoxemia, and will typically trigger an alarm in a hospital setting.

A technique called pulse oximetry measures SpO2. Technically this parameter is determined from a patient's arterial oxygen saturation, or SpO2, which is a percentage of oxygenated arterial hemoglobin present in their blood. Functional hemoglobin molecules can bind with up to four oxygen molecules to yield 'oxygenated' hemoglobin (HbO2). A hemoglobin molecule bound to less than four oxygen molecules is classified as 'reduced' hemoglobin (Hb). Conventional pulse oximeters feature algorithms that assume only HbO2 and Hb are present in the blood, and measure SpO2 from the ratio of oxygenated hemoglobin to the total amount of hemoglobin (both oxygenated and reduced) according to equation (1):

$$SpO2 = \frac{HbO2}{HbO2 + Hb} \quad (1)$$

HbO2 and Hb feature different absorption spectra in the visible and infrared regions, and can therefore be measured optically. Conventional pulse oximeters thus typically feature light sources (most typically light-emitting diodes, or LEDs) that radiate in the red (near 660 nm) and infrared (typically between 900-950 nm) spectral regions. A photodetector measures a portion of radiation at each wavelength that transmits through the patient's pulsating blood, but is not absorbed. At 660 nm, for example, Hb absorbs about ten times as much radiation as HbO2, whereas at 905 nm HbO2 absorbs about two times as much radiation as Hb. Detection of transmitted radiation at these wavelengths yields two time-dependent waveforms, each called a plethysmogram (PPG), that an oximeter analyzes to solve for SpO2 as defined in equation (1) above.

Specifically, the oximeter processes PPG waveforms measured with red (RED(PPG)) and infrared (IR(PPG)) wavelengths to determine time-dependent AC signals and time-independent DC signals. The term 'AC' signals, as used herein, refers to a portion of a PPG waveform that varies relatively rapidly with time, e.g. the portion of the signal originating by pulsations in the patient's blood. 'DC' signals, in contrast, are portions of the PPG that are relatively invariant with time, e.g. the portion of the signal originating from scattering off of components such as bone, skin, and non-pulsating components of the patient's blood.

More specifically, AC signals are measured from a heartbeat-induced pulse present in both waveforms. The pulse represents a pressure wave, launched by the heart, which propagates through the patient's vasculature and causes a time-dependent increase in volume in both arteries and capillaries. When the pressure pulse reaches vasculature irradiated by the oximeter's optical system, a temporary volumetric increase results in a relatively large optical absorption according to the Beer-Lambert Law. DC signals originate from radiation scattering from static components such as bone, skin, and relatively non-pulsatile components of both arterial and venous blood. Typically only about 0.5-1% of the total signal measured by the photodetector originates from the AC signal, with the remainder originating from the DC signal. Separation of AC and DC signals is typically done with both analog and digital filtering techniques that are well-known in the art.

During pulse oximetry a normalized 'r' value is typically calculated from AC and DC signals using equation (2), below:

$$r = \frac{660 \text{ nm(AC)}/660 \text{ nm(DC)}}{905 \text{ nm(AC)}/905 \text{ nm(DC)}} \quad (2)$$

r, which is sometimes called a 'ratio of ratios' (RoR), represents a ratio of Hb to HbO2. It equates an actual SpO2 value, which ranges from 0-100% O2, to an empirical relationship that resembles a non-linear equation. Above about 70% O2 this equation typically yields values that are accurate to a few percent. Measurements below this value, while not necessarily accurate, still indicate a hypoxic patient in need of medical attention.

Pulse oximeters for measuring SpO2 were originally developed in 1972, and have evolved over the last 30 years to a point where they are commonplace in nearly all vital sign monitors for in-hospital use. Typical pulse oximeters feature a probe encased in a clothespin-shaped housing that includes both red and infrared LEDs, and a photodetector that detects radiation from the LEDs after it passes through a portion of the patient's body. The probe typically clips to a patient's index finger. Most probes operate in a transmission-mode optical geometry, and relay analog waveforms measured by LEDs and the photodetector to an external processing unit. The processing unit is typically integrated into a stand-alone monitor that measures only SpO2 and pulse rate (determined from the AC signal of one of the PPG waveforms), or a complete vital sign monitor that measures SpO2 along with systolic (SYS), mean (MAP), and diastolic (DIA) blood pressure, heart rate (HR), respiratory rate (RR), and temperature (TEMP). In both cases the oximeter probe typically connects to the monitor through a cable. Alternate configurations of SpO2 monitors include those that operate in reflection-mode optical geometries, probes that clip onto appendages other than the patient's finger (e.g. their ear or forehead), and processing units that are worn directly on the patient's body (e.g. their wrist). In some cases PPG waveforms, along with SpO2 and pulse rate values, are sent wirelessly from the oximeter to a remote display.

Because it is based on an optical measurement, pulse oximetry can be extremely sensitive to a patient's motion. Activities such as walking, finger tapping, falling, and convulsing can result in a number of artifacts that distort both the AC and DC components of waveforms measured with the oximeter's optical system. Motion-related activities, for example, can cause the oximeter probe to move relative to the patient's finger, change the amount of ambient light that irradiates the photodetector, and disrupt both arterial and venus blood flow in vasculature measured by the optical system. Each of these events can generate artifacts that, in some cases, are similar to the AC and DC signals within the PPG waveforms. Ultimately this can cause the pulse oximeter to generate inaccurate values and false alarms.

Oximeters suffer other problems outside of their measurement accuracy. Probes encapsulating a patient's index finger can be uncomfortable and awkward, especially when worn for extended periods of time. Pulse oximeters that lack body-worn processing units can only provide measurements when a patient is sedentary and attached to a bedside monitor; they are impractical for ambulatory patients moving about the hospital, making it difficult to provide true continuous monitoring. Most body-worn oximeters typically lack systems for continuously measuring all vital signs, and particularly blood pressure, from a patient.

SUMMARY OF THE INVENTION

The invention described herein provides a body-worn monitor that continuously measures pulse oximetry and other vital signs, along with motion, posture, and activity level, from an ambulatory patient. The system features an oximetry probe that comfortably clips to the base of the patient's thumb, thereby freeing up their fingers for conventional activities in a hospital, such as reading and eating. The probe reversibly secures to the thumb with, e.g., an easy-to-use Velcro strap, disposable tape, or similar closure, or may be provided in the form of a closed ring which slips over the thumb. It measures time-dependent waveforms (RED/IR(PPG)) corresponding to LEDs typically operating near 660 nm and 905 nm. Analog versions of these waveforms pass through a low-profile cable to a wrist-worn transceiver enclosing a processing unit. Also within the wrist-worn transceiver is a wireless system (typically based wireless protocols such as 802.11 and 802.15.4) that sends information through a network to a remote receiver, e.g. a computer located in a central nursing station.

Clinically accurate pulse oximetry measurements made at the base of the patient's thumb require a set of coefficients relating r (from Eq. 2) to SpO2 that are typically determined with a set of empirical experiments (e.g. a 'breathe down' study, described below). These coefficients differ from those used in conventional oximetry measurements because of the differences between vasculature in the base of the thumb and the tip of the index finger. Typically the base of the thumb features relatively fewer capillary beds, and thus the coefficients are preferably adjusted accordingly.

Three motion-detecting sensors (e.g. accelerometers) form part of the body-worn monitoring system. They are typically secured to the patient's torso (e.g. chest), upper arm (e.g. bicep), and lower arm (e.g. wrist), and measure time-dependent motion signals (ACC waveforms). The wrist-worn transceiver receives and processes these motion signals to determine the patient's degree of motion, posture, and activity level. Each sensor typically measures a unique ACC waveform along three axes (x, y, and z), and ultimately yields information that can be processed to determine a separate component of the patient's motion. For example, the sensor worn on the lower arm (which may be within the wrist-worn transceiver) monitors movement of the patient's hand and fingers; such motion typically disrupts the RED/IR(PPG) waveforms. It can therefore be processed and used to exclude certain noise-corrupted artifacts from the SpO2 calculation. Sensors attached to the lower and upper arms each measure signals that are collectively analyzed to estimate the patient's arm height; this can be used to improve accuracy of a continuous blood pressure measurement (cNIBP), as described below. And the sensor attached to the patient's chest measures signals that are analyzed to determine the patient's posture and activity level, which can affect measurements for SpO2, cNIBP, and other vital signs. Algorithms for processing information from the accelerometers for these purposes are described in detail in the following patent applications, the contents of which are fully incorporated herein by reference: BODY-WORN MONITOR FEATURING ALARM SYSTEM THAT PROCESSES A PATIENT'S MOTION AND VITAL SIGNS (U.S. Ser. No. 12/469,182; filed May 20, 2009) and BODY-WORN VITAL SIGN MONITOR WITH SYSTEM FOR DETECTING AND ANALYZING MOTION (U.S. Ser. No. 12/469,094; filed May 20, 2009). As described therein, knowledge of a patient's motion, activity level, and posture can greatly enhance the accuracy of alarms/alerts generated by the body-worn monitor. For example, a walking patient typically yields noisy PPG waveforms, but also has a low probability of being hypoxic due to their activity state. According to the invention, a patient in this condition thus does not typically generate an alarm/alert, regardless of the value of SpO2 that is measured. Similarly, a patient that is convulsing or falling typically yields noisy RED/IR(PPG) waveforms from which it is difficult to extract an SpO2 value. But these activity states, regardless of the patient's SpO2 values, may trigger an alarm/alert because they indicate the patient needs medical assistance.

The body-worn monitor features systems for continuously monitoring patients in a hospital environment, and as the patient ultimately transfers from the hospital to the home. Both SpO2 and cNIBP rely on accurate measurement of PPG and ACC waveforms, along with an electrocardiogram waveform (ECG), from patients that are both moving and at rest. cNIBP is typically measured with the 'Composite Technique', which is described in detail in the co-pending patent application entitled: VITAL SIGN MONITOR FOR MEASURING BLOOD PRESSURE USING OPTICAL, ELECTRICAL, AND PRESSURE WAVEFORMS (U.S. Ser. No. 12/138,194; filed Jun. 12, 2008), the contents of which are fully incorporated herein by reference.

As described in these applications, the Composite Technique (or, alternatively, the 'Hybrid Technique' referred to therein) typically uses a single PPG waveform from the SpO2 measurement (typically the IR(PPG) waveform, as this typically has a better signal-to-noise ratio than the RED(PPG) waveform), along with the ECG waveform, to calculate a parameter called 'pulse transit time' (PTT) which strongly correlates to blood pressure. Specifically, the ECG waveform features a sharply peaked QRS complex that indicates depolarization of the heart's left ventricle, and, informally, provides a time-dependent marker of a heart beat. PTT is the time separating the peak of the QRS complex and the onset, or 'foot', of the RED/IR(PPG) waveforms; it is typically a few hundred milliseconds. The QRS complex, along with the foot of each pulse in the RED/IR(PPG), can be used to more accurately extract AC signals using a mathematical technique described in detail below. In other embodiments both the RED/IR(PPG) waveforms are collectively processed to enhance the accuracy of the cNIBP measurement.

The electrical system for measuring SpO2 features a small-scale, low-power circuit mounted on a circuit board that fits within the wrist-worn transceiver. The transceiver can further include a touchpanel display, barcode reader, and wireless systems for ancillary applications described, for example, in the following applications, the contents of which have been previously incorporated by reference: BODY-WORN MONITOR FEATURING ALARM SYSTEM THAT PROCESSES A PATIENT'S MOTION AND VITAL SIGNS (U.S. Ser. No. 12/469,182; filed May 20, 2009) and BODY-WORN VITAL SIGN MONITOR WITH SYSTEM FOR DETECTING AND ANALYZING MOTION (U.S. Ser. No. 12/469,094; filed May 20, 2009).

In one aspect, the invention provides a system and method for monitoring a physiological property of a patient's blood (e.g. a SpO2 value). The invention features a first sensor with two radiation sources that emit optical radiation at first and second wavelengths, and a photodetector configured to detect the radiation after it passes through a portion of the patient. A finger-ring housing that houses the radiation sources and the photodetector features a ring-shaped mounting portion that fits or wraps around a base of the patient's thumb. A processing unit, worn on the patient's wrist and operably connected to the finger-ring sensor, receives signals from the photodetector and includes both a motion sensor and a processor. The processor is configured to process: i) the first and second signals to determine AC signals; ii) at least one of the AC signals and the motion signal to determine selected AC signals; and iii) the selected AC signals, or signals derived therefrom, to determine the physiological property of the patient's blood.

In certain embodiments, the mounting portion comprises a curved, ring-shaped portion that partially surrounds the base of the patient's thumb, while leaving the tip uncovered. The ring-shaped portion can connect to a flexible strap made of, e.g., nylon or fabric. Typically the first and second radiation sources are proximal to one another (and are often within the same electronic package) and are separated from the photodetector by an angle between 75-110 degrees. In these and other embodiments the processing unit includes an input port (e.g. a serial port operating a serial protocol, such a control area network, or CAN protocol) configured to receive an electrical signal (e.g. a digitized ECG signal). The ECG signal, for example, is generated by a series of body-worn electrodes connected to differential amplifier circuit. The cable that supplies the ECG signal can include this circuit, and can plug directly into the serial input port. The ECG signal includes a time-dependent marker (e.g. a QRS complex) that precedes both the first and second PPG waveforms generated by each heartbeat by less than predetermined time period (e.g. 500 ms). It can be processed to determine heart rate, and can additionally be processed to detect both the AC and DC signals within the PPG waveforms, along with motion that may disrupt them. If motion is detected, the system can be instructed to simply ignore the AC and DC components; this is typically done if motion exceeds a pre-determined level known to corrupt these signals beyond an acceptable level. Alternatively, if motion is present but is less than the pre-determined level, its influence over the AC and DC components may be removed using frequency-domain filtering, deconvolution, or similar techniques.

In other embodiments both cNIBP and SpO2 are simultaneously detected from both the PPG and ECG signals. cNIBP is determined, for example, from a time difference between a peak of a QRS complex in the ECG signal and an onset point in one of the AC signals. The time difference, for example, is PTT, and cNIBP is determined according to the Composite Technique. In this case, cNIBP is most accurately determined when the finger-ring sensor is worn on the base of the patient's thumb. For this configuration, parameters relating ratios of the AC and DC signals to SpO2 need to be determined beforehand using, e.g., conventional breathe down studies.

In another aspect, the invention provides a method for simultaneously measuring both SpO2 and a motion-related event (e.g. a patient's posture, activity level, and degree of motion) from the patient. Typically posture may be measured with a single sensor (e.g. an analog or digital three-axis accelerometer) mounted on the patient's torso. The accelerometer can be mounted alongside the ECG circuit in a terminal portion of the ECG cable. In this embodiment, posture is typically determined from a vector corresponding to orientation of the patient's torso. Specifically, an angle separating the vector from a pre-determined coordinate system ultimately yields posture, as is described in detail below. Activity level (corresponding, e.g., to moving, walking, falling, convulsing) is another motion-related event determined in this embodiment. It can be calculated from a mathematical transform of time-dependent variations of a motion signal that yields a frequency-domain spectrum. Portions of the spectrum (e.g. the power of specific frequency components) are compared to pre-determined frequency-dependent parameters to determine the activity level. Other operations, such as a mathematical derivative of the time-dependent motion signal, or a series of 'decision rules' based on a decision-tree algorithm, can also yield the activity level.

In another aspect, the invention provides a complete body-worn vital sign monitor for measuring all the patient's vital signs, including SpO2, cNIBP, and oscillometric blood pressure (SYS, DIA, and MAP). Typically in this embodiment the body-worn monitor features a wrist-worn processing unit that includes, for example, multiple input ports to operably connect with stand-alone systems for measuring some of the vital signs (e.g. to receive cables associated with systems for measuring ECG and oscillometric blood pressure). Additional ports may also be used to collect signals from external sensors that measure, e.g., glucose level, respiration rate, and end-tidal $CO_2$. To simplify data collection, each port typically operates on a common communication protocol, such as the CAN protocol. Input ports corresponding to ECG and oscillometric blood pressure are typically located on a common side of the processing unit that typically faces away from the patient's hand. In this embodiment any cable connecting to an input port may include an accelerometer to characterize the patient's motion.

In certain embodiments the processing unit features a touchpanel display that renders a first user interface that displays information describing oxygen saturation, a second user interface that displays information describing blood pressure, and a third user interface that displays information describing ECG signals. The processing unit can also include a barcode scanner that scans a barcode of a medical professional (located, e.g., on their badge). In response, the wrist-worn transceiver can render a user interface corresponding to the medical professional. This prevents the patient from viewing medical information that may, for example, cause unnecessary alarm.

In other embodiments the processing unit includes a speaker for voice communications, or for generating audible voice messages intended for the patient. The processing unit can also include a wireless transmitter that communicates through, e.g., a hospital network.

In another aspect, the invention provides a method for measuring SpO2 and cNIBP by processing ECG, PPG, and motion signals with filters that analyze both PTT and AC signals of the PPG waveforms with a mathematical filter. The filter, for example, can be a 'matched filter', described in detail below. Typically only signals that are generated when motion is relatively low are considered in this embodiment. For example, signals are typically not processed further when the motion sensors indicate that motion is greater than an acceptable level. Filtering PTT values includes, for example, determining values that lie outside a pre-determined range using statistical filters (e.g. a simple average and standard deviation). More sophisticated techniques, such as calculating a power value from a frequency-domain spectrum corresponding to the time-dependent motion signal, and then comparing this to a pre-determined value, can be used to estimate if either the PTT values or PPG signals are affected by motion. SpO2 values are typically calculated from ratios describing the AC and DC signals measured from individual pulses using optical systems operating in the red and infrared optical spectral regions. One or more ratios can be calculated for the pulse.

In another aspect, the invention provides a method for suppressing an alarm/alert based on the SpO2 value by processing the patient's posture and activity state. For example, the alarm can be suppressed if the patient's posture is upright (e.g. standing up), as patients having this posture are typically not in immediate need of medical assistance. Similarly, the alarm can be suppressed if the patient's posture changes from lying down to sitting or standing up (or, alternatively, the other way around). In this case the change in posture, which can be determined with the chest-worn accelerometer, may disrupt the PPG waveforms to the point where an alarm/alert would be falsely generated in the absence of such alarm suppression.

Still other embodiments are found in the following detailed description of the invention, and in the claims.

BRIEF DESCRIPTION OF THE DRAWINGS

FIGS. 10A and 10B are graphs, respectively, of time-dependent IR(PPG), ECG, and ACC waveforms measured when a patient is undergoing minor finger motion;

FIGS. 11A and 11B are graphs, respectively, of time-dependent IR(PPG), ECG, and ACC waveforms measured when a patient is undergoing major finger motion;

FIG. 12A is a graph of time-dependent RED/IR(PPG), ECG, and ACC waveforms similar to those shown in FIGS. 9A,B-11A,B measured during periods of motion and no motion;

FIGS. 12B and 12D are graphs of the IR(PPG) waveforms of FIG. 12A measured, respectively, during periods of motion and no motion, along with a graphical indication of how multiple RoRs are calculated from the waveforms;

FIG. 12C is a graph of data points representing RoRs between components of the RED(PPG) and IR(PPG) waveforms measured during periods of no motion and at periodic intervals between the foot and peak of the waveform shown in FIG. 12B;

FIGS. 12E and 12F are graphs of data points representing RoRs between components of the RED(PPG) and IR(PPG) waveforms measured during periods of motion at periodic intervals between the foot and peak of the waveform shown in FIG. 12D;

FIG. 13A shows a graph of time-dependent ECG and IR(PPG) waveforms that are processed to determine a PPT (corresponding to steps 105 and 106 in FIG. 13D);

FIGS. 13B and 13C are graphs, respectively, of PTT versus heartbeat before (corresponding to steps 107 and 108 in FIG. 13D) and after (corresponding to step 110 in FIG. 13D) applying a matched filter to the IR(PPG) waveform used to calculate PTT as shown in FIG. 13A;

FIG. 13D is a flow chart showing an algorithm for analyzing PTT and applying a matched filter to an IR(PPG) waveform when motion-related noise is present in the waveform;

FIGS. 23A and 23B show images of the body-worn monitor of FIG. 1 attached to a patient with and without, respectively, a cuff-based pneumatic system used for calibrating the cNIBP measurement.

DETAILED DESCRIPTION OF THE INVENTION

Figure 1:
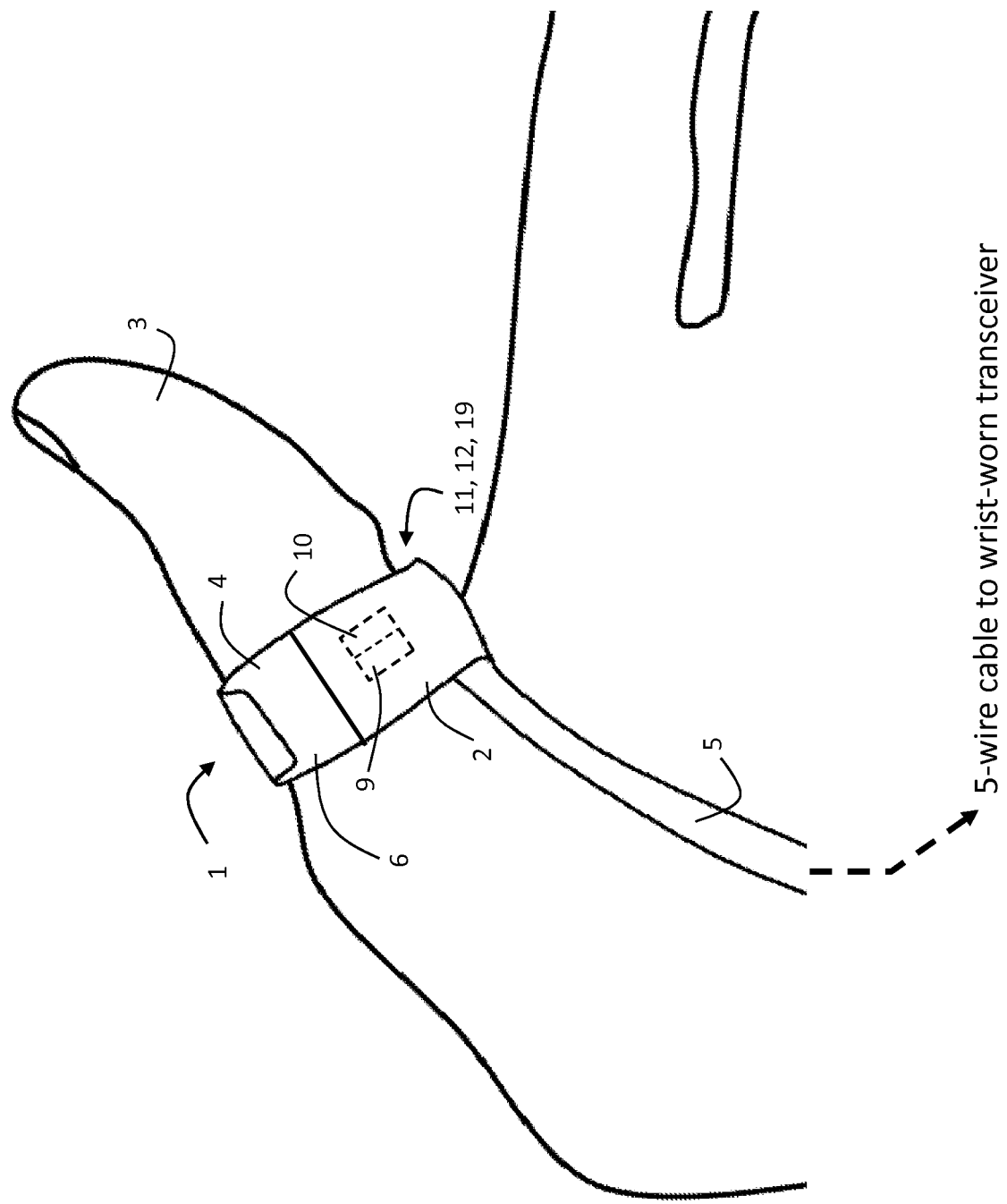
FIG. 1 shows a schematic drawing of a pulse oximeter probe configured as a finger-ring sensor worn around the base of a patient's thumb.
Figure 2:
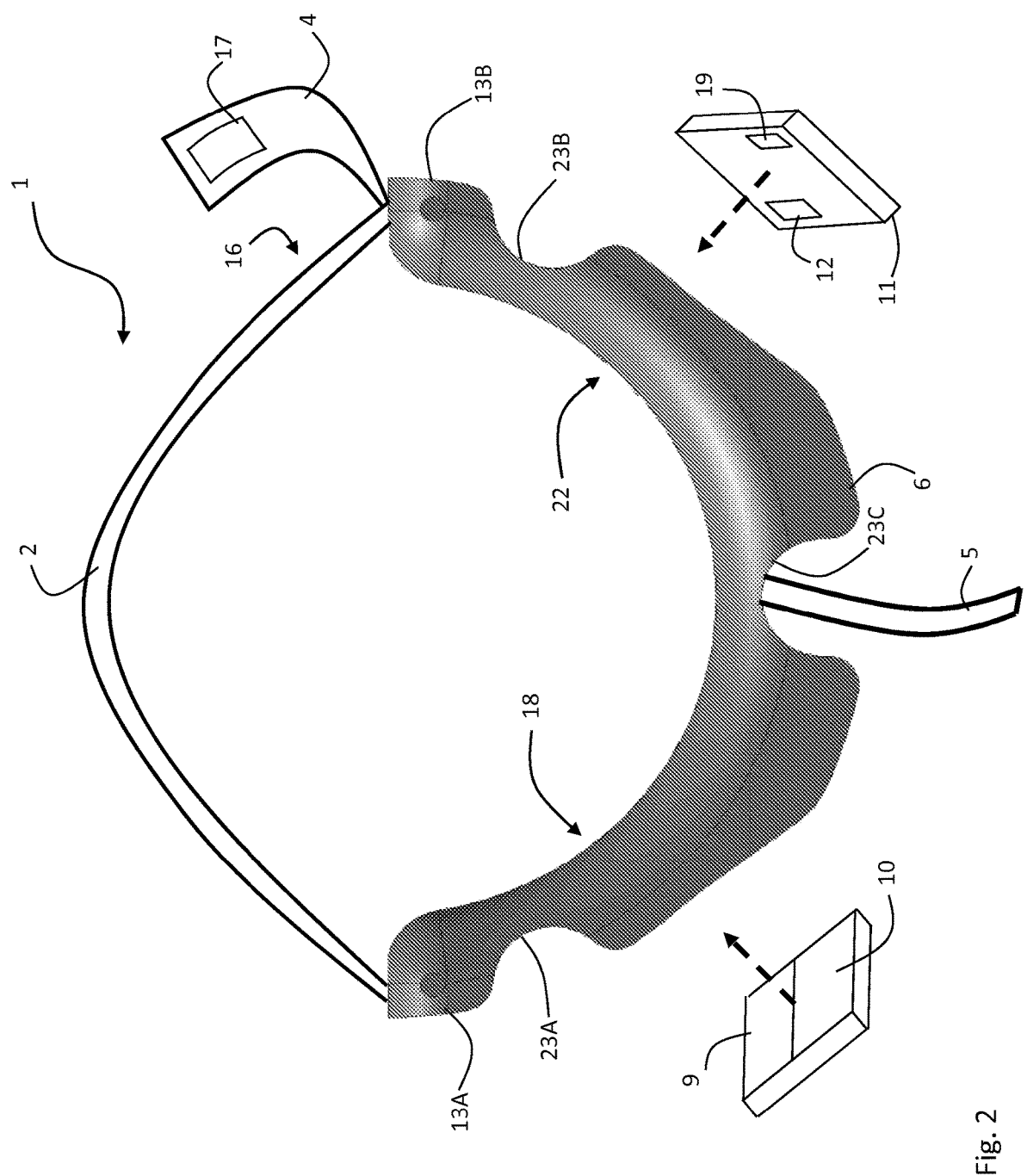
FIG. 2 shows an expanded, schematic drawing of the pulse oximeter probe of FIG. 1 with a dual-wavelength LED and photodetector separated from the finger-ring sensor.

FIGS. 1 and 2 show a pulse oximeter probe 1 shaped as a finger ring that wraps around a base of patient's thumb 3 to measure SpO2 and cNIBP. The probe 1 is designed to be comfortably worn for extended periods (e.g. several days) while freeing up the patient's thumb and hands for activities such as reading and eating that are commonplace in, e.g., a hospital. Motion corresponding to these and other activities can affect the SpO2 measurement and is detected with a network of accelerometers worn on the patient's body. The probe 1 makes a transmission-mode optical measurement along an inner portion of the thumb 3 with a pair of embedded LEDs 9, 10 operating at, respectively, 660 and 905 nm, and a single photodetector 12 that detects these wavelengths after they pass through vasculature and other tissue lying beneath the LEDs 9, 10. Specifically, both LEDs 9, 10 and the photodetector 12 are positioned to measure blood pulsing in portions of the princeps pollicis artery, which is the principal artery of the thumb and stems from the radial artery. As described in detail below, measuring blood flowing in this artery enhances the accuracy of the cNIBP measurement. A small circuit board 11 supports the photodetector 12 and may additionally include, for example, a trans-impedance amplifier for amplifying photocurrent from the photodetector 12 and converting it into a corresponding voltage. The circuit board 11 also includes a resistor 19 that identifies specific wavelengths emitted by the LEDs 9, 10; these wavelengths, in turn, influence values of correlation coefficients that relate RoR to SpO2, as described below. Some of these circuit elements are described in more detail below with reference to FIGS. 21 and 22.

Figure 22:
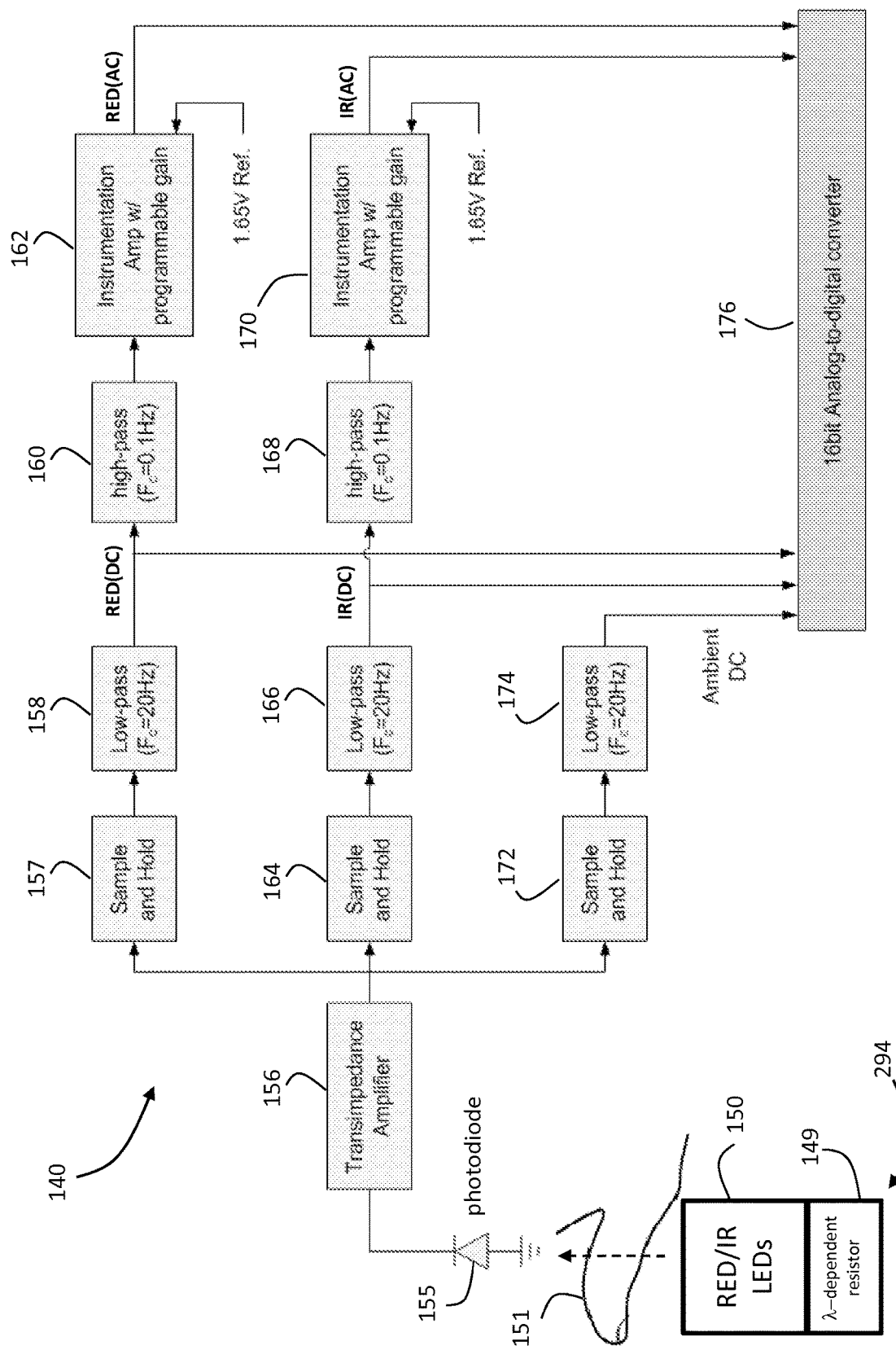
FIG. 22 is an electrical diagram of a circuit used to amplify and filter the RED/IR(PPG) waveforms to generate the RED/IR(AC) and RED/IR(DC) components used to calculate SpO2.

A ring-shaped, flexible plastic housing 6 formed into a cylindrical radius of curvature features rectangular openings 18, 22 that support the LEDs 9, 10 and circuit board 11. The housing 6 features three cut-out portions 23A-C, or 'living hinges', that make it easily bendable and able to accommodate thumbs of difference sizes. It is held in place around the base of the thumb with a flexible nylon strap 2 threading through two D-ring openings 13A, 13B located the housing's distal ends. A portion 4 of the strap 2 features a patch 17 of Velcro (containing, e.g., 'hooks') that adheres to a mated patch 16 (containing, e.g., 'loops') on the strap's main portion; the patches 16, 17 temporarily adhere to each other when the housing 6 is worn on the patient's thumb 3, and easily detach so that it can be removed. The straps 2, 4 allow the probe 1 to be securely fastened, which in turn minimizes motion relative to the measurement site. A flexible, cable 5 connects the oximeter probe 1 to a wrist-worn transceiver, similar to the one shown in FIG. 24. The cable 5 carries 110 signals from the wrist-worn transceiver that drive the LEDs according to the timing diagram in FIG. 20, and analog signals measured by the photodetector to an amplifying/filtering circuit within the transceiver, as shown in FIG. 22. There, the analog signals are amplified, filtered, digitized, and processed to measure SpO2, as described in detail below.

Figure 3:
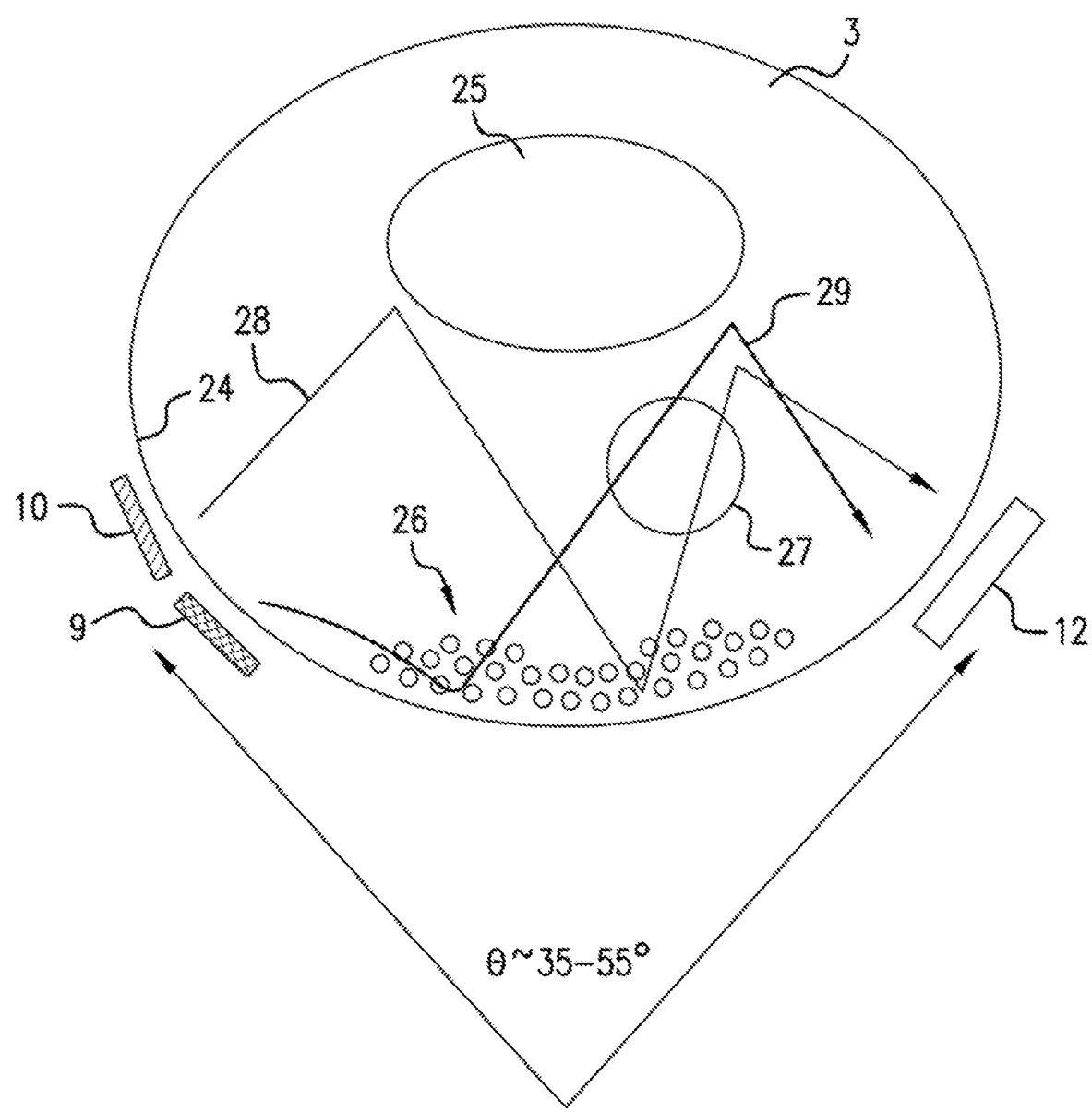
FIG. 3 shows a schematic drawing of a patient's thumb 3 depicting the angular separation of embedded LEDs 9, 10 relative to photodetector 12 in the pulse oximeter probe.
Figure 20:
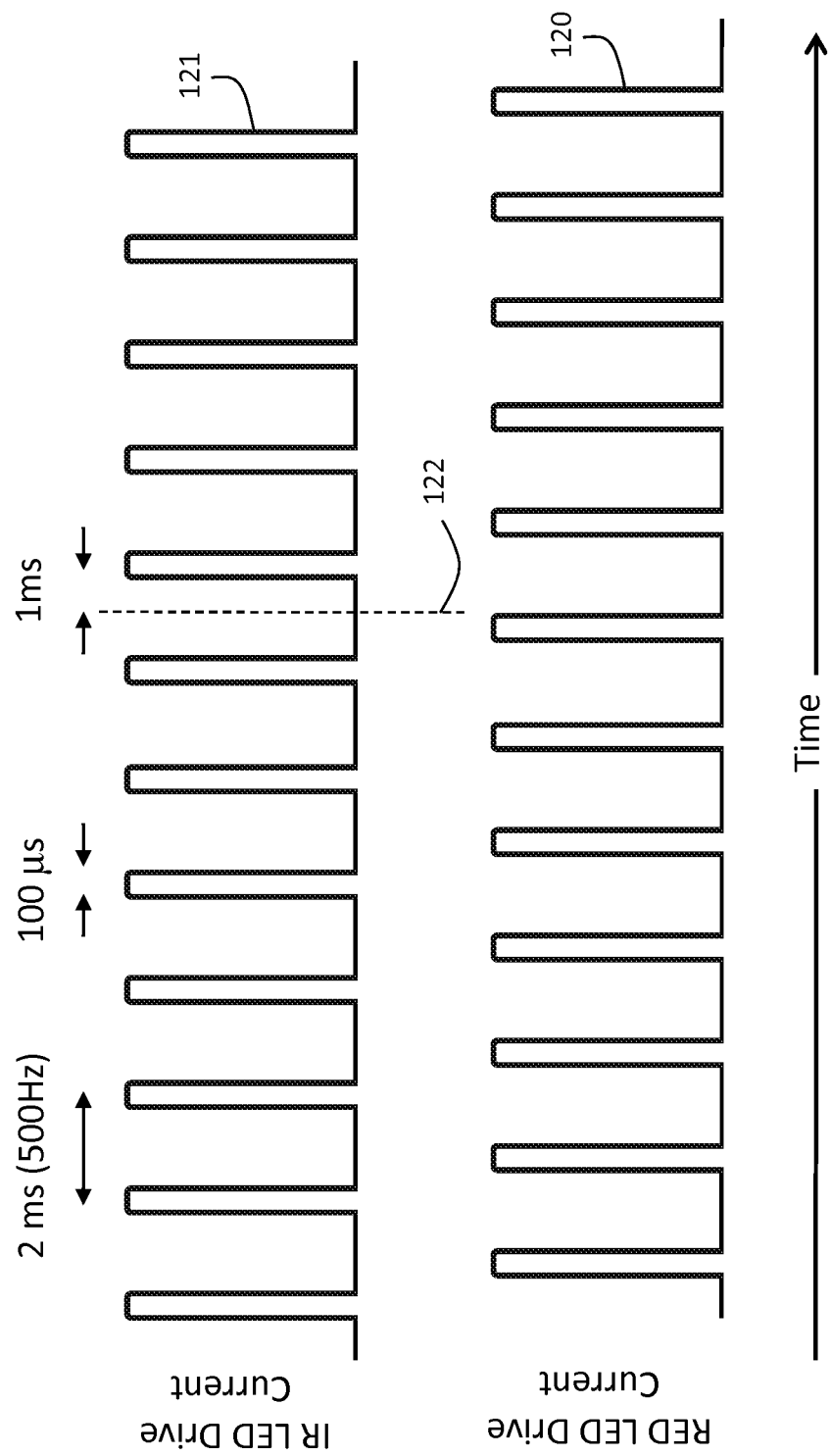
FIG. 20 is an electrical timing diagram showing how the 660 nm and 905 nm LEDs are driven in the pulse oximeter probe described in FIG. 1.

As shown in FIG. 3, during a pulse oximetry measurement the LEDs 9, 10 intermittently emit beams 28, 29 of radiation at 660 nm and 905 nm at roughly 500 Hz according to the timing diagram in FIG. 20. Once emitted, the beams 28, 29 pass through the base of the thumb 3 and rapidly diverge to scatter off tissue such as skin 24, bone 25, capillaries 26 near the thumb's outer surface, and a portion of the princeps pollicis artery 27 before reaching the photodetector 12. To increase the amount of radiation that passes through the artery 27 and capillaries 26, and thereby optimize signal quality, the LEDs 9, 10 and photodiode 12 are separated by approximately 35-55 degrees. Optical components separated at this angle tend to increase the relative contribution of signal coming from the artery 27; ultimately this improves the accuracy of the cNIBP measurement, as PTT values measured from arterial components correlate better to blood pressure than those measured from capillary components. Both the capillaries 26 and princeps pollicis artery 27 carry blood that pulsates with each heartbeat and absorbs radiation emitted by the LEDs 9, 10. This results in separate time-dependent optical waveforms (i.e. RED/IR (PPG), shown in FIG. 6, generated by the 660 and 905 nm radiation. Both waveforms feature AC signals corresponding to the time-dependent pulsating blood, and DC signals corresponding to time-independent scattering off the skin 24, bone 25, and non-pulsating components of the capillaries 26 and artery 27. Prior to any filtering the AC component typically represents about 0.5-1% of the total signal.

Collectively processing both the AC and DC signals of the RED/IR(PPG) waveforms yields a SpO2 value. The body-worn monitor calculates these components using a number of signal-processing methodologies that are additionally important for determining PTT-based cNIBP. Ultimately the AC and DC components yield a RoR which then relates to a SpO2 using a series of empirically determined coefficients. In one embodiment, for example, the RoR is determined by first measuring RED/IR(PPG) waveforms, and then passing them through a low-pass filter characterized by a 20 Hz cutoff. The averaged baseline components of each waveform are sampled and stored in memory, and represent RED/IR (DC). Both waveforms are then additionally filtered with high-pass filter having a 0.1 Hz cutoff frequency, which is typically implemented with a finite impulse response function, and finally amplified with a variable gain amplifier. These steps can be done with either analog electronic or digital software filters. Components passing through this filter are isolated as described below with reference to FIGS. 6 and 7 to yield RED/IR(AC). Once determined, the AC and DC signals are processed to yield a RoR value, described in equation (3), which relates to SpO2:

$$RoR = \frac{RED(AC)/RED(DC)}{IR(AC)/IR(DC)} \quad (3)$$

Figure 4:
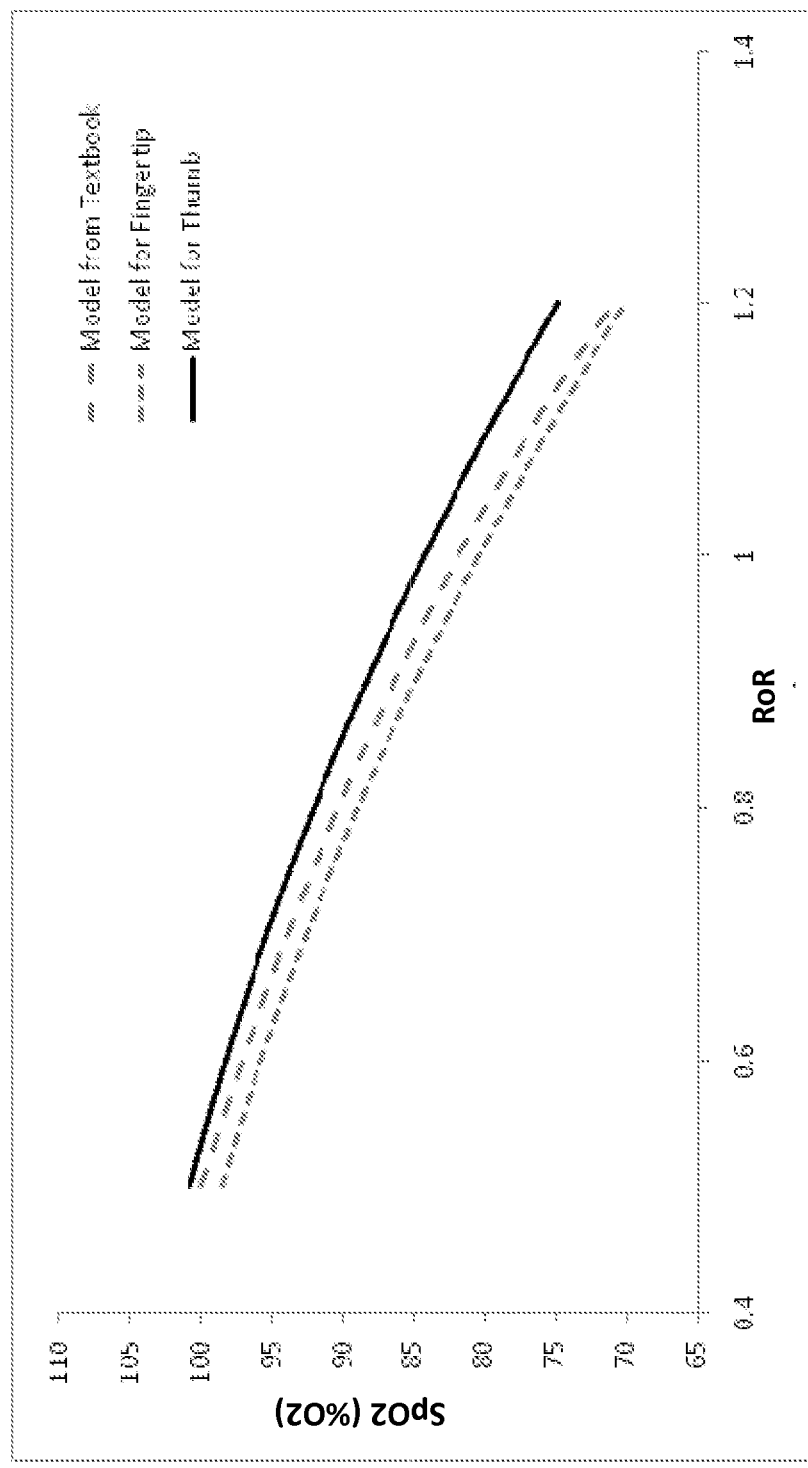
FIG. 4 is a graph showing a relationship between SpO2 and a 'ratio of ratios' (RoR) for measurements from theoretical model in a medical textbook, made from the tip of a patient's index finger, and made from the base of a patient's thumb.

FIG. 4 shows an empirical relationship between RoR and SpO2 for measurements made at the base of the thumb with the oximeter probe shown in FIGS. 1 and 2 (solid line), along with similar relationships for measurements made at the tip of the index finger with an off-the-shelf oximeter probe (small dashes), and the theoretical curve for measurements made from the tip of the index finger (large dashes). Curves corresponding to measurements made from the index finger and thumb are determined empirically from a group of patients measured under similar conditions. As is clear from the figure, the relationships between RoR and SpO2 are similar, but slightly offset due to differences in the measurement site. Without being bound to any theory, these differences may be due to the relatively low density of capillary beds near the base of the thumb as compared to those in the tip of the index finger. The relationship for all curves in FIG. 4 is non-linear, particularly for SpO2 values ranging from about 70-100%. Values below 70% can be accounted for with a different non-linear model, such as one based on a second-order polynomial. Coefficients a, b, and c for this model are determined by fitting the empirical data to a corresponding mathematical function like the second-order polynomial shown in equation (4) below:

$$SpO2 = (a + b*RoR + c*RoR^2) \times 100 \quad (4)$$

Optimized values for a, b, and c coefficients corresponding to measurements made at the base of the thumb are shown in Table 1, below:

TABLE 1 coefficients for equation 4 relating RoR to SpO2 for measurements made at the base of the thumb

| Parameter | Value |
|---|---|
| a | 107.3 |
| b | −3.0 |
| c | −20.0 |

The exact values of parameters shown in Table 1 will depend of the specific wavelengths of the LEDs used in the pulse oximeter probe. This is because the SpO2 measurement is fundamentally determined by the relative optical absorption of Hb and HbO2 in the red and infrared spectral regions, and absorption, in turn, will depend on the wavelength emitted by the LEDs. The absorption spectra of Hb and HbO2 are relatively flat in the infrared spectral region, but strongly diverge in the red spectral region. The coefficients shown in Table 1 are thus relatively sensitive to the exact wavelength of the red LED. For this reason, a series of empirical studies need to be performed using pulse oximeter probes featuring LEDs of varying wavelengths surrounding the red emission wavelength (e.g. 600-610 nm) prior to manufacturing. Such a study, for example, is described with reference to FIG. 8. It is typically classified as a 'breathe down' study because it involves lowering the SpO2 values of a series of patients (typically about 10-15) under medical supervision. SpO2 is typically lowered by decreasing the amount of oxygen each patient inhales through a specialized ventilator mask; this is often done in a room with a reduced temperature. Blood from the patients is extracted from an arterial line and analyzed with a blood gas analyzer to determine its oxygen content. Simultaneously, a pulse oximeter probe with known LED wavelengths is attached to each patient (in this case at the base of the thumb) and used to measure the RoR described in equation (3). SpO2 values for this experiment, as measured with the blood gas analyzer, typically range from 70-100%. Simultaneous studies are typically done using pulse oximeter probes having LEDs with different red emission spectra. Upon completion of the studies, the wavelength-dependent values of RoR are related to SpO2, as determined by the blood gas analyzer, to calculate coefficients a, b, c as described in Table 1. In general, a different set of coefficients will result for the different LED wavelengths. These coefficients and the optical wavelengths they correspond to, along with a resistor value described below, are stored in a database in memory on the wrist-worn transceiver.

Prior to manufacturing of the pulse oximeter probe (e.g. the probe shown in FIG. 1), the wavelengths of the LEDs are determined, typically with a resolution of about 1 nm, using an emission spectrophotometer. LEDs are then sorted by wavelength and associated with a resistor having a value that is stored in the above-described database. During manufacturing, the resistor is soldered to the circuit board (and optionally trimmed with a laser to give it a well-defined resistance) within the pulse oximeter probe shown in FIG. 1. During an actual measurement, the wrist-worn transceiver delivers a voltage through the cable connecting it to the pulse oximeter probe that decreases in value after passing through the resistor. This voltage drop is sensed by the transceiver using the analog-to-digital converter and processor, and then used to calculate the resistor value. The value is compared to the database, and ultimately used to select the appropriate a, b, and c coefficients described above. Ultimately this maximizes accuracy of the SpO2 calculation.

Measurements made at the base of the thumb provide accurate SpO2 values and increase patient comfort. Additionally, the IR(PPG) measured from this site, when processed in combination to the ECG waveform, yields a PTT value that can be processed with the Composite Technique to yield an accurate cNIBP measurement. As described above, an IR(PPG) waveform measured from primarily from the princeps pollicis artery increases the accuracy of the cNIBP measurement. With an initial pressure-based calibration (performed e.g. by the pneumatic system 285 shown in FIG. 23A) SYS and DIA can be explicitly determined for each heartbeat using an algorithm described in the above-mentioned patent applications, the contents of which have been previously incorporated herein by reference. Typically, PTT values are processed over a 20-40 second time period (often implemented as a 'rolling average') using statistical filtering to improve accuracy. To better define the onset of the PPG waveform, and thus improve the accuracy to which SYS and DIA are determined, times corresponding to RED (foot) and IR(foot) are typically averaged together. When compared to SYS and DIA values measured under clinical conditions with a femoral arterial line, cNIBP measurements made from this particular location were well within the FDA's standards for accuracy (+/−5 mmHg) and standard deviation (8 mmHg). For this and other reasons the base of the thumb appears to be a uniquely good location for measuring both SpO2 and cNIBP.

Figure 5:
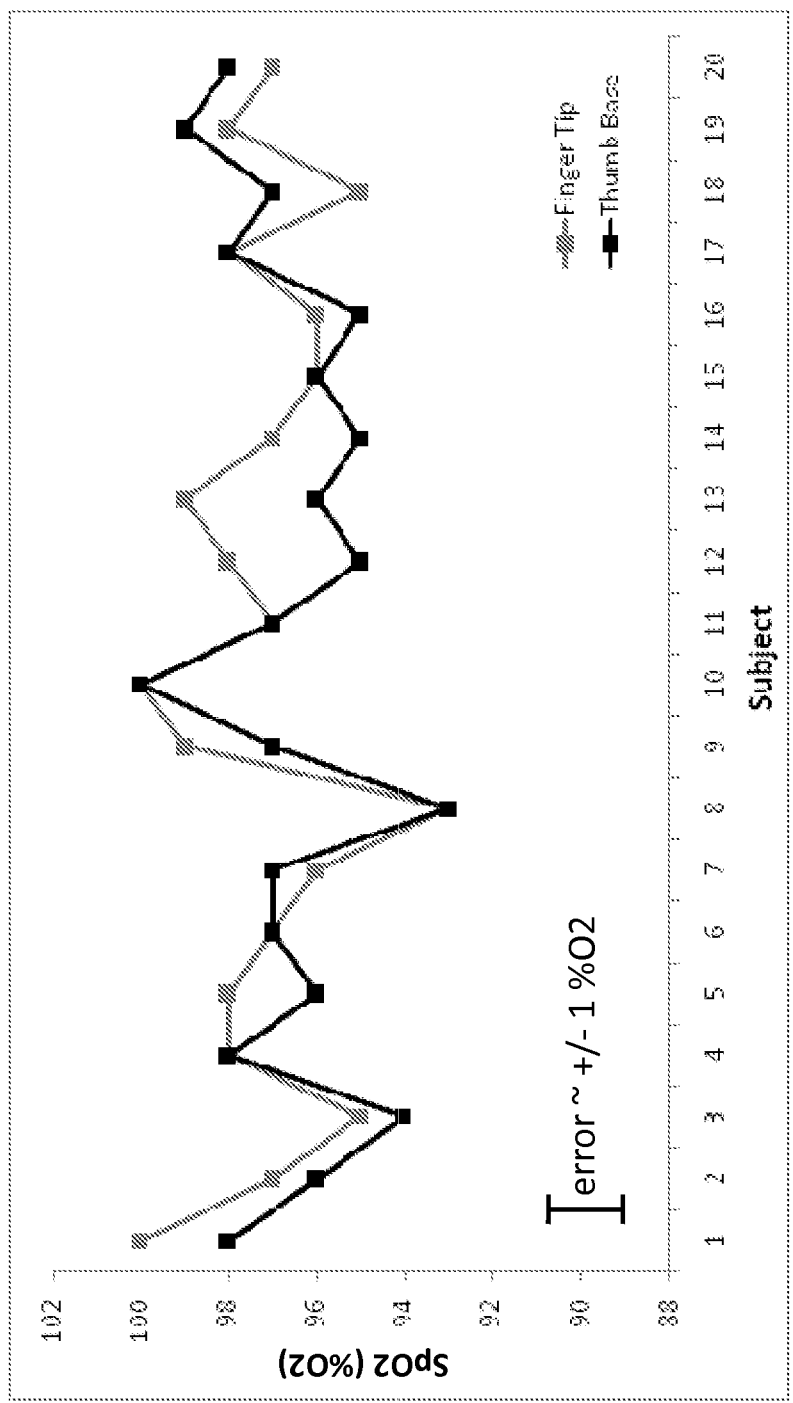
FIG. 5 is a graph comparing measurements from 20 unique patients made with the thumb-worn pulse oximeter probe of FIG. 1 to those made at the tip of the index finger with a commercial oximeter probe.

FIG. 5 shows a direct comparison between SpO2 measured from the base of the thumb and tip of the index finger from a group of 20 separate patients. Each patient was measured for a 30-second period from the tip of finger with a commercially available oximeter probe, and then for a comparable period from the base of the thumb with an oximeter probe substantially similar to that shown in FIGS. 1 and 2. During the measurement an average value for SpO2 was detected from each location. For these patients the relationships between RoR and SpO2 shown in FIG. 4 were used for both sets of measurements. As is clear from the data, the correlation for these measurements is within experimental error (estimated at 1% SpO2 for each measurement) for all 20 patients. The mean difference between the two measurements (thumb SpO2-index finger SpO2) is −0.6% O2, and the standard deviation of the differences is 1.39% O2. Measurements were made over a range of 93-100% O2.

Figure 6:
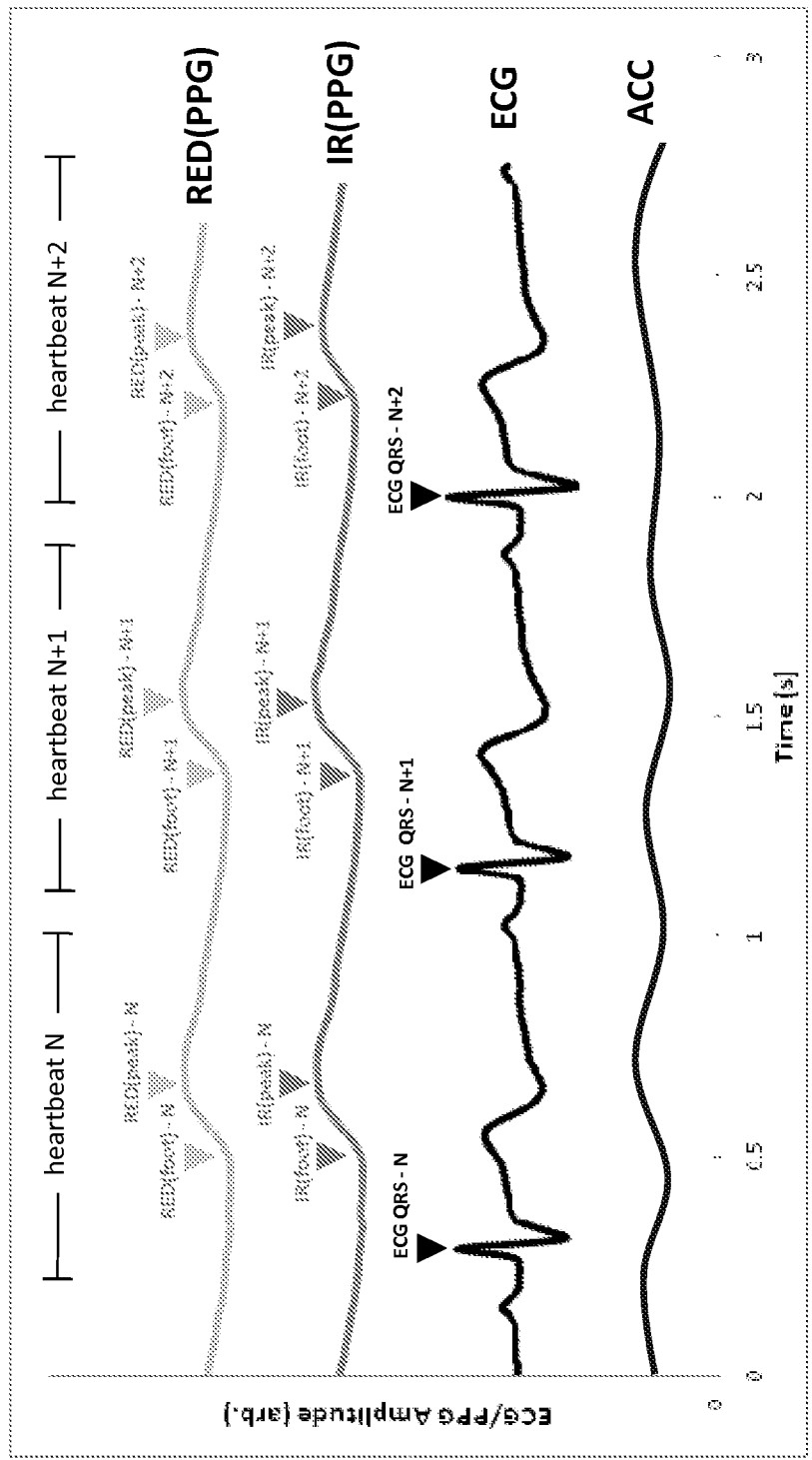
FIG. 6 is a graph showing time-dependent waveforms measured with an accelerometer (ACC), ECG system (ECG), and the 660 and 905 nm LEDs (RED(PPG) and IR(PPG), respectively) within the pulse oximeter probe of FIG. 1.

The pulse oximeter system described above is integrated into a complete, body-worn monitoring system, shown in FIGS. 23A and 23B, that measures and analyzes ECG, ACC, RED(PPG) and IR(PPG) waveforms to characterize the patient's vital signs, degree of motion, activity level, and posture. FIG. 6, for example, shows the various time-dependent waveforms measured concurrently over a 3-second period using such a system. The ACC waveform represents a measurement along a single axis made by one of the three accelerometers incorporated in the body-worn monitor. Typically this is the accelerometer included in the wrist-worn transceiver, as this site is closest to the measurement site for SpO2. SpO2 values are determined by measuring the red and infrared waveforms between the peak and foot values, indicated by colored triangles in the figure and described in more detail below. Typically these peak values are determined by filtering each waveform as described above, and then taking a first derivative and evaluating a zero-point crossing, indicating the point where the waveform's slope changes from a positive to negative value. Values for these parameters can be averaged over several pulses and processed with statistical techniques (e.g. averaging after excluding values outside of +/−1 standard deviation) to yield the RED/IR(peak) values for individual pulses within the RED/IR(PPG) waveforms. RED/IR(foot) values for each pulse are used for PTT-based cNIBP measurements, and are typically processed with statistical techniques as described above. The foot of each waveform is best calculated by measuring a peak from the second derivative of the RED/IR(PPG) waveforms. RED/IR(DC) values (not shown in the figure) are typically determined by sampling RED/IR(PPG) waveforms after passing analog versions of these waveforms through a low-pass filter as described above.

Electrodes adhered to the patient's chest and connected to an ECG circuit in the body-worn monitor measure a three-lead ECG, with FIG. 6 showing a time-dependent waveform taken from Lead II. The ECG waveform features a series of QRS complexes, indicated by the black triangles, with each QRS complex corresponding to a single heartbeat. The QRS complex typically proceeds each pulse in the RED/IR(PPG) by between about 100-200 milliseconds, and is easy to detect because of its sharp, well-defined features. Moreover, as described in more detail below with reference to FIGS. 9A,B-11A,B, the ECG waveform and its associated QRS complexes are relatively insensitive to motion, in contrast the both the RED/IR(PPG) waveforms. This means each QRS complex can serve as a marker or 'fiducial' for detecting AC signals in the two PPGs. Specifically, during a measurement an algorithm operating on the wrist-worn transceiver detects a QRS complex (e.g. ECG QRS-N) and then sequentially analyzes both the RED/IR(PPG) waveforms at times within 500 ms of this feature. If RED/IR(foot) and RED/IR(peak) cannot be determined during this time interval using the first and second derivative tests described above, the algorithm determines that they are immeasurable (most likely because of noise in the PPG), and begins searching for similar values corresponding to the next heartbeat. If the ACC waveform indicates a high degree of motion, then the RED/IR(PPG) waveforms are processed as described below to determine if foot and peak parameters can be extracted from them. If not, the waveforms are determined to be immeasurable, the first and second derivative tests are not performed, and the ECG and PPG waveforms corresponding to the N+1 heartbeat are investigated. This process is repeated, typically for a total time of between 5-10 seconds, for as many heartbeats as possible.

If no more than an acceptable level of motion is present, as indicated by the ACC waveform, then the values for RED/IR(foot) and RED/IR(peak) can be processed to determine an RoR for each heartbeat. This value can then be analyzed with the statistical techniques described above to limit artifacts and ultimately generate a SpO2 value with the greatest possible accuracy. In one embodiment, to convert the RED/IR(peak) and RED/IR(foot) values into AC values used for the RoR calculation, the amplitude of each pulse in the RED/IR(PPG) waveforms is calculated as shown in equations (5) and (6) below:

$$RED(AMP) = RED(peak) - RED(foot) \tag{5}$$

$$IR(AMP) = IR(peak) - IR(foot) \tag{6}$$

The DC values for the RED/IR(PPG) waveforms are then determined by first calculating any DC offset values (RED/IR(DC)) supplied to the differential inputs of the analog-to-digital converter; these inputs are indicated, for example, by RED/IR(DC) labels in FIG. 22. Once digitized, these values can then be used to calculate an 'effective' DC value, RED/IR(DC*), for both the red and infrared wavelengths, as described below in equations (7) and (8). Ambient light, defined as AMBIENT(DC), is accounted for by measuring any radiation incident on the photodetector when neither the red or infrared LEDs are turned on (this occurs, for example, between current pulses that drive the respective LEDs, as shown in FIG. 20).

$$RED(DC*) = \frac{RED(peak) + RED(foot)}{2} + RED(DC) - AMBIENT(DC) \tag{7}$$

$$IR(DC*) = \frac{IR(peak) + IR(foot)}{2} + IR(DC) - AMBIENT(DC) \tag{8}$$

An RoR value is then determined from equations (5)-(8):

$$RoR = \frac{RED(AMP)/RED(DC*)}{IR(AMP)/IR(DC*)} \tag{9}$$

The ACC waveform in FIG. 6 provides an accurate indication of the patient's motion. Typically this waveform, along with two others corresponding to additional axes of a coordinate system, is sensed with a solid-state device called an accelerometer. An accelerometer is typically a micro electrical-mechanical system (MEMS) device that measures the acceleration of the part of the body that it is attached to. The ACC waveform measured by the accelerometer features DC values that indicate the position of the accelerometer relative to a gravity vector, and AC values that indicate movement-induced acceleration. Suitable accelerometers typically have a response times less than about 1 microsecond, and are thus more than adequate for detecting most types of patient motion, which typically occurs in less than 15 Hz. Processing the ACC waveforms yields at least three valuable pieces of information relevant to the SpO2 measurement: it can determine i) a patient's posture; ii) their activity state (e.g. are they lying down, walking, sitting, standing); and iii) whether or not the patient's hand in moving, thereby indicating that the IR/RED(PPG) waveforms may be corrupted by noise, and thus more likely to yield erroneous values for SpO2. Additional processing of the ACC waveforms yields the patient's arm height, from which hydrostatic changes in blood pressure can be estimated and used to calibrate the cNIBP measurement. The process for detecting each of these scenarios is summarized below, and in detail in the following patent applications, the contents of which have been fully incorporated herein by reference: BODY-WORN MONITOR FEATURING ALARM SYSTEM THAT PROCESSES A PATIENT'S MOTION AND VITAL SIGNS (U.S. Ser. No. 12/469,182; filed May 20, 2009) and BODY-WORN VITAL SIGN MONITOR WITH SYSTEM FOR DETECTING AND ANALYZING MOTION (U.S. Ser. No. 12/469,094; filed May 20, 2009).

Figure 7:
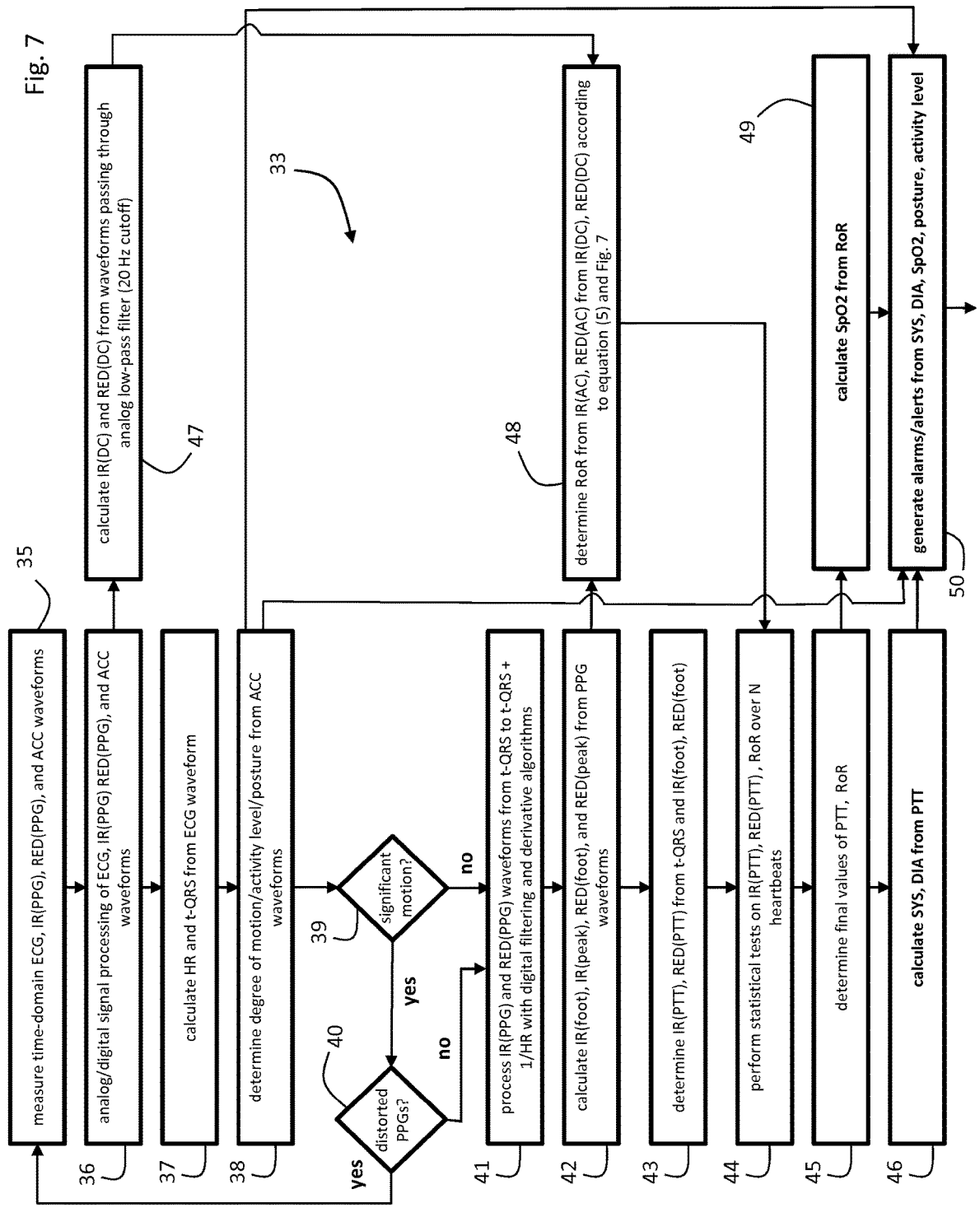
FIG. 7 is a flow chart describing an algorithm for measuring SpO2 and patient motion with the pulse oximeter probe of FIG. 1.

FIG. 7 shows a flow chart describing an algorithm 33 that collectively determines SpO2, SYS, and DIA, along with a patient's motion, posture, and activity level, by processing the time-dependent RED/IR(PPG), ECG, and ACC waveforms shown in FIG. 6. The algorithm 33 begins with measuring the ECG, RED/IR(PPG), and ACC waveforms (nine total waveforms measured with three separate accelerometers) using a body-worn monitor, similar to that shown in FIGS. 23A, 23B (step 35). RED/IR(PPG) waveforms are measured with the pulse oximeter probe described above, and the ECG waveform is measured with an ECG circuit that terminates an ECG cable and attaches to at least three electrodes worn on the patient's chest. Three accelerometers are typically disposed, respectively, in the wrist-worn transceiver, in a cable that attaches to the patient's bicep, and on the chest proximal to the ECG circuit. A series of analog filters (performed with hardware components described with reference to FIG. 22) and digital filters (performed in software using well-known frequency-domain techniques, such as using a 'matched filter', described below) process each waveform to remove unwanted and relatively high-frequency electrical and mechanical noise (step 36). Such filtering, for example, increases the accuracy to which data points corresponding to IR/RED(peak) and IR/RED(foot) can be determined. Typically RED/IR(DC) values are determined directly from waveforms that pass through a low-pass filter characterized by a 20 hz cutoff frequency, as described in equations (7) and (8), above (step 47). After filtering, the ECG QRS for each heartbeat is detected with a beat-picking algorithm described, for example, in the following reference, the contents of which are incorporated herein by reference (step 37): 'ECG Beat Detection Using Filter Banks', Afonso et al., *IEEE Trans. Biomed Eng.*, 46:192-202 (1999). Heart rate is typically determined from the inverse of time separating neighboring QRS complexes. Degree of motion, posture, and activity level are then determined from the nine ACC waveforms, as described in detail in the above-referenced patent applications, and briefly below (step 38). Each of these parameters features its own unique classification. For example, degree of motion can be ranked numerically depending on the magnitude of acceleration detected from one or more accelerometers. Posture is typically divided into well-known categories such as standing, lying on back, lying prone, etc. Activity levels include activities such as walking, falling, resting, and convulsing.

If the algorithm determines that no significant motion is present (step 39), it proceeds to process the RED/IR(PPG) waveforms, starting at a time corresponding to the ECG QRS generated by a first heartbeat, and continuing the processing until a pre-determined time delta (e.g. 500 ms) or a time corresponding to a neighboring heart beat is reached (step 41). As used herein, 'significant motion' refers to an amount of motion that would render the RED/IR(PPG) waveforms unreliable for calculation of SpO2. This processing typically involves further digitally filtering the waveforms to remove any high-frequency noise, and then determining IR/PPG(peak) values from the first derivative of each waveform, and IR/PPG(foot) values from the second derivative of each waveform (step 42). If during step 39 motion is determined to be present, the algorithm proceeds to analyze both RED/IR(PPG) waveforms to determine if they are distorted in any way (step 40). Such analysis, for example, can involve complex methods such as comparing a pulse from one or both of the PPG waveforms to a 'known good pulse' collected during a period of relatively low motion. In this case, the comparative method can be a linear or non-linear numerical fitting algorithm, such as a least-squares or Levenburg-Marquardt algorithm, or based on a standard correlation algorithm that determines agreement between the immediate pulse and the known good pulse. This latter approach can be implemented as a 'matched filter', and is described in detail below with regard to equations (13) and (14). A matched filter algorithm, for example, is preferably implemented in step 36 to improve the signal-to-noise ratio of both the PPG and, to a lesser extent, the ECG waveform prior to processing these signals. Or it could be implemented during step 40 to determine a degree of correlation between the immediate pulse in the PPG waveform and a known good pulse to determine if the immediate pulse is corrupted by motion. A derivation of the matched filter is provided, for example, in Turin, 'An introduction to matched filters', *IRE Transactions of Information Theory* 6: 311-329 (1960), the contents of which are incorporated herein by reference.

A relatively simple method for determining a known good pulse involves, for example, determining the standard deviation of the PPG waveform during a time period commensurate with the ECG QRS (at this point the pulse is not evident in the PPG waveform), and comparing this to a pre-determined metric to estimate the motion-induced noise in the waveform. If either PPG is determined to be significantly distorted by motion, it is not included in the algorithm, and the processes of collecting and analyzing RED/IR(PPG), ECG, and ACC waveforms is repeated (steps 35-38, 47).

As described above, values for RED/IR(foot) and RED/IR(peak) can be used to calculate both SpO2 and cNIBP. For the cNIBP calculation, RED/IR(PTT) values are determined from the time difference separating the ECG QRS and RED/IR(foot). Values corresponding to RED/IR(AC) are determined from the waveforms between the RED/IR(foot)

and RED/IR(peak) values, as described above in equation (9), and below in equations (10)-(11). This yields a RoR for each heartbeat-induced pulse in the waveforms. Both RED/IR(AC) and RED/IR(PTT) values are typically determined for each heartbeat measured over a pre-determined period ranging from about 10-30 seconds, and then subjected to a series of statistical tests (step 44) that typically involve taking the average and standard deviation of each value over the time period. A 'rolling average' can also be used during step 44 so that fresh values are determined, e.g., every second. Values that lie outside of one standard deviation from the average are typically removed, and then the average is recalculated. The final average value of PTT is then determined as the average of the averaged RED/IR(PTT) values, while the final average value of RED/IR(AC) is determined in a similar manner from the RoR values determined for each pulse (step 45). The algorithm calculates cNIBP values of SYS and DIA directly from the averaged PTT value, as described in detail in the above-referenced patent applications (step 46). Using equation (4), it calculates SpO2 from the RoR values determined during step 45.

To accurately generate alarms/alerts when continuously monitoring a patient, it is often necessary to consider both the patient's vital signs and their motion. Thus, during step 50, an alarm/alert is only generated from SYS, DIA, and SpO2 values after processing the patient's degree of motion, posture, and activity level (determined during step 38). For example, if the patient is determined to be walking with a normal gate, it can be assumed that their values of SYS, DIA, and SpO2 do not warrant an alarm/alert, even if one or all of these parameters exceeds a pre-determined alarm threshold. Conversely, an alarm/alert for a falling or convulsing patient would likely be generated even if the values for SYS, DIA, and SpO2 fall within the pre-determined alarm thresholds. Specific methodologies for alarms/alerts that consider both vital signs and patient motion are found in the above-referenced patent applications, the contents of which have been previously incorporated by reference.

Figure 8:
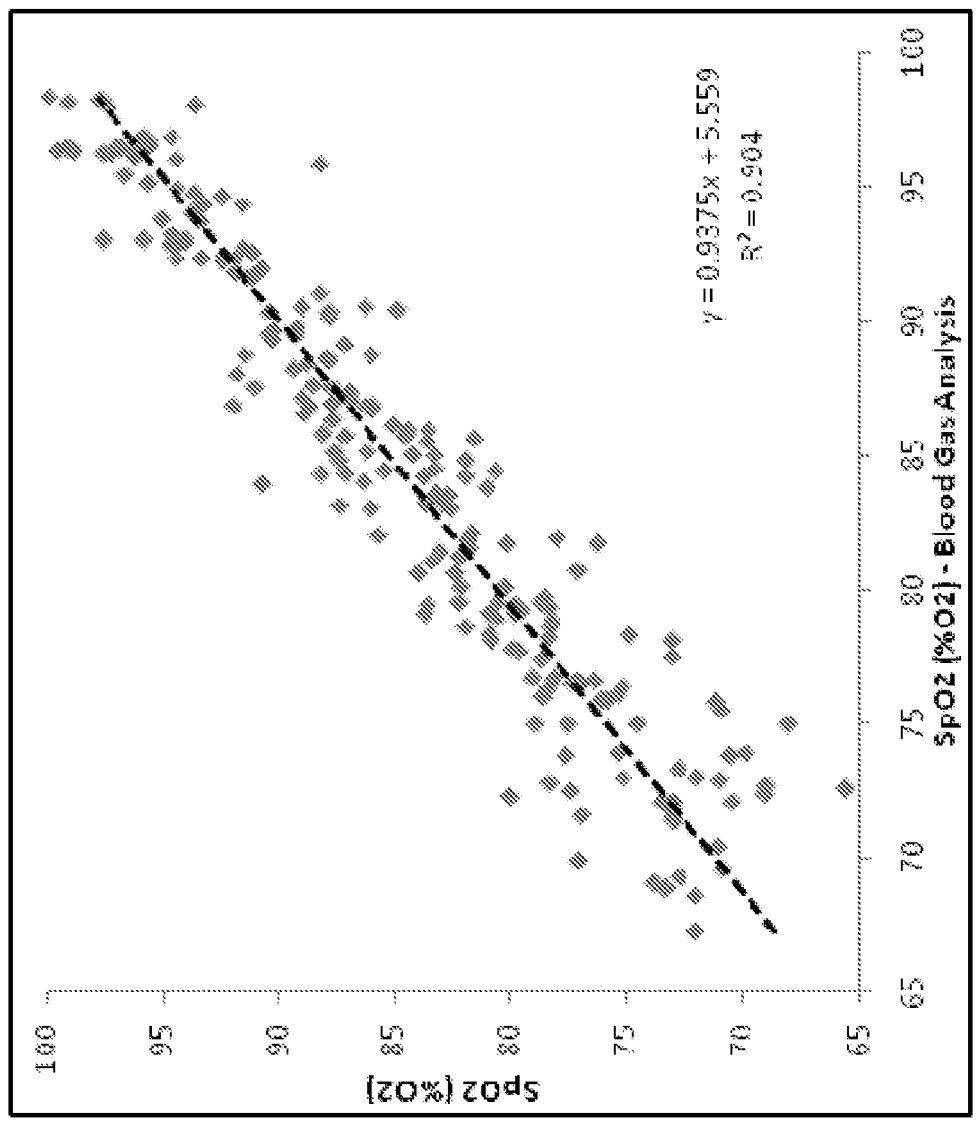
FIG. 8 is a graph showing data collected during a breathe down study indicating correlation between SpO2 measured with the pulse oximeter probe shown in FIG. 2 and SpO2 measured with a blood gas analyzer, which in this case represents a 'gold standard'.

As shown in FIG. 8, SpO2 data collected with the pulse oximeter probe shown in FIG. 2 and processed with the algorithm shown in FIG. 7 correlate well with that analyzed with a blood gas analyzer, which in this case represents a 'gold standard'. Data shown in the figure were collected during a conventional breathe down study, wherein SpO2 values of 15 healthy volunteers were systematically lowered from a normal value near 100% O2 to an abnormal value near about 70% O2 by carefully controlling the subjects' oxygen intake. In total, about 20 data points were measured for each subject over this range. Blood samples for the blood gas analyzer were extracted using an in-dwelling catheter, similar to a conventional arterial line, inserted in the subjects' radial artery. Data in the graph measured according to the invention described herein (shown along the y-axis) correlate well with the gold standard (x-axis), yielding an r^2 value of 0.9. The BIAS for this correlation is −0.3% O2, and the standard deviation is 2.56% O2. Data were collected and analyzed with a prototype system, and indicate the efficacy of the invention described herein. They are expected to further improve with a production-quality system. As is clear from the graph, correlation for relatively low SpO2 values (e.g. those near 70% O2) is worse than that for relatively high SpO2 values (e.g. those near 95%); such a measurement response is typical for commercially available pulse oximeters, and is primarily due to a decreasing signal-to-noise ration in the RED(PPG), which decreases with SpO2.

Figure 9A:
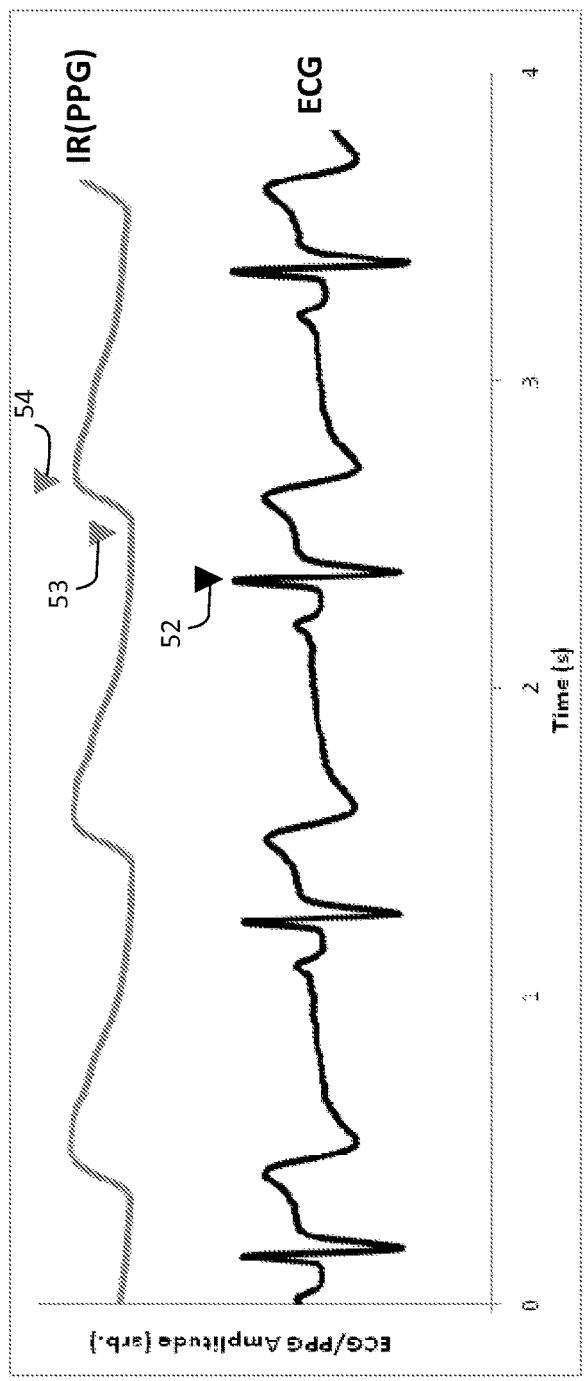
FIGS. 9A and 9B are graphs, respectively, of time-dependent IR(PPG), ECG, and ACC waveforms measured when a patient is not undergoing motion.

FIGS. 9A,B-11A,B indicate how different degrees of motion from a patient's fingers can influence both ECG and PPG signals, thereby affecting the accuracy of both SpO2 and cNIBP measurements. In these figures the IR(PPG) is shown, as this signal typically has a better signal-to-noise ratio than that of the RED(PPG). The ACC waveform is typically measured along the vertical axis of the accelerometer embedded in the wrist-worn transceiver. The magnitude of the axes for ECG, PPG, and ACC waveforms are the same for all figures.

Figure 9B:
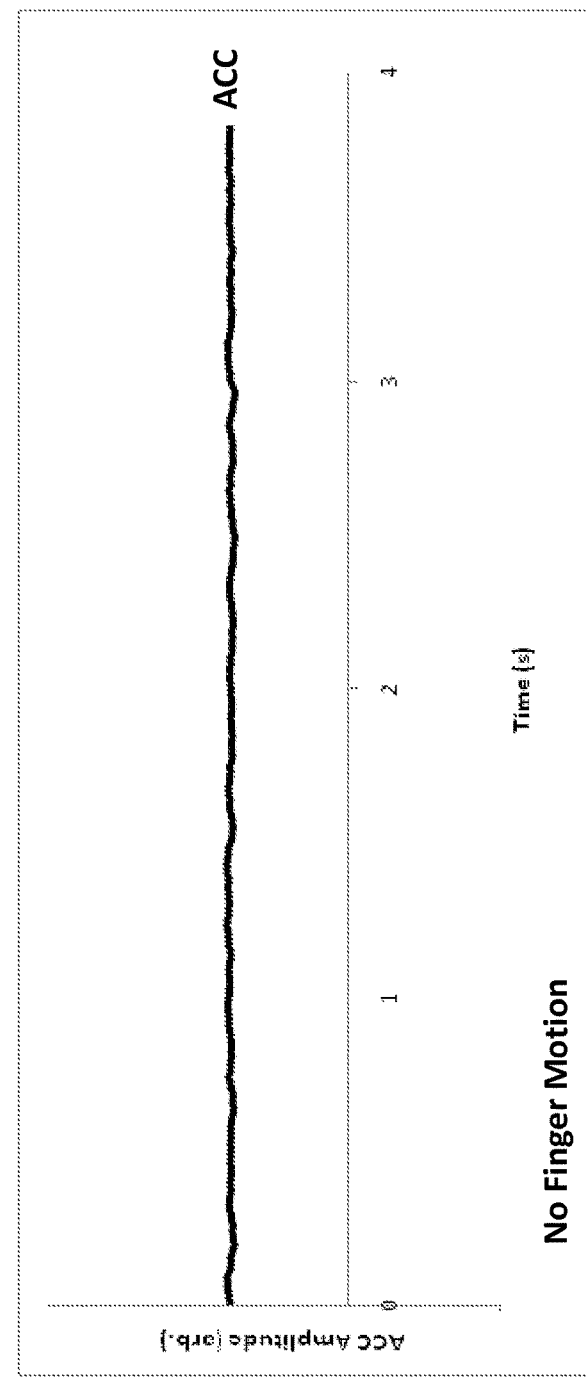

In FIG. 9B, for example, the ACC waveform is relatively flat and lacking any significant time-dependent features, indicating that the patient is not moving and is relatively still. Consequently the IR(PPG) in FIG. 9A, which is strongly affected by motion, features well-defined values for IR(foot), indicated by marker 53, and IR(peak), indicated by marker 54. Likewise the ECG waveform features a QRS complex, indicated by marker 52, which is undistorted. The fidelity of these features indicate that both SpO2 and cNIBP values can typically be accurately determined during periods of little or no motion, as indicated by the ACC waveform in FIG. 9B.

FIGS. 10A,B show how minor amounts of finger motion affect both the ECG and IR(PPG) waveforms. As shown by a portion of the dashed box 60 in FIG. 10B, finger motion is manifested by a time-dependent change in the ACC waveform, the beginning of which is indicated by marker 62, which persists for a little less than one second. This is in stark contrast to the portion of the ACC waveform in the preceding dashed box 56, which indicates no motion. Finger motion has basically no effect on the ECG waveform and its associated QRS complex, as indicated by marker 61. But the motion causes a minor amount of distortion of the IR(PPG) waveform. Specifically, when the motion is maximized (i.e. at the time corresponding to marker 62) a small bump indicated by marker 57 appears in the IR(PPG) waveform. This bump is an artifact that, in the absence of the ACC waveform, could be misinterpreted as a pulse containing both a foot and peak in the IR(PPG) waveform. Additionally, the minor finger motion distorts the foot (marker 58) and peak (marker 59) of the subsequent pulse in the IR(PPG) waveform, making it difficult to accurately determine these parameters using the derivative tests described above. Thus, rather than erroneously interpreting these features and generating inaccurate values for both SpO2 and cNIBP, an algorithm described herein can disregard them based on the magnitude of the ACC waveform, and continue its calculation of vital signs once the finger motion is reduced to an acceptable level.

FIGS. 11A,B show the affects of a major amount of finger motion on both the ECG and IR(PPG) waveforms. Here, the period of motion is indicated in both figures by the dashed box 65, which contrasts with the preceding period where motion is not present, shown in the dashed box 66. The ACC waveform in FIG. 11B indicates the finger motion lasts for roughly one second, beginning and ending at times indicated, respectively, near markers 68 and 69. The motion is complex and peaks in intensity at marker 69. Even for major finger motion the ECG waveform and its QRS complex, indicated by marker 67, are relatively undistorted. But the IR(PPG) measured during the period of motion is strongly distorted to the point that its peak value, indicated by marker 64, is relatively flat and basically immeasurable. This makes it difficult to accurately measure IR(AC) and the subsequent SpO2 value calculated from this parameter. The IR(foot) value, indicated by marker 63, is also distorted, but to a lesser degree than the corresponding peak value.

Data shown in FIGS. 9A,B-11A,B indicate that motion can be detected and accounted for during pulse oximetry measurements to minimize the occurrence of false alarms and, additionally, make accurate readings in the presence of motion. For example, Equation (9), above, yields a single RoR value for each pulse in the RED/IR(PPG) waveforms. However the method for calculating SpO2 based on a single value is limited, as only one RoR can be calculated for each heartbeat; if values from several heartbeats are averaged together it can thus take several seconds to update the SpO2 value. And the single RoR value can be strongly influenced by motion during pulses within the RED/IR(PPG) waveforms, as described above with reference to FIGS. 9A, B-11A, B.

Alternatively, RoR can be calculated using a method indicated schematically in FIGS. 12A-F. In this method, multiple 'sub-ratios' between AC components corresponding to RED/IR(PPGs) are calculated from the foot of each pulse to its corresponding peak, determined as described above. The sub-ratios are calculated for each time interval of cc (typically 33 ms, corresponding to 30 Hz) and only during periods of no motion, as determined from the ACC waveforms. Once a group of sub-ratios are determined for a given pulse, they can be processed with a variety of statistical techniques, described in detail below, to estimate an accurate RoR for a given pulse. This RoR can then be further processed for multiple pulses. A pulse oximetry measurement based on sub-ratios has the advantage of being relatively accurate and having a faster update rate when compared to the method associated with equation (9), which calculates just a single RoR for each pulse in the RED/IR (PPG) waveforms. Such a measurement is described in more detail in the following reference, the contents of which are incorporated herein by reference: Wukitsch et al., 'Pulse Oximetry: Analysis of Theory, Technology, and Practice', *Journal of Clinical Monitoring*, 4:290-301 (1988).

FIG. 12A shows ACC, ECG, and RED/IR(PPG) waveforms measured during periods of no motion (indicated by the dashed box 70) and motion (indicated by the dashed box 71). As with FIGS. 9A-11A, motion in FIG. 12A is indicated by sharp, abrupt changes in the ACC waveform generated along a vertical axis by an accelerometer mounted in the wrist-worn transceiver. The ECG waveforms shown in both dashed boxes 70, 71 are relatively immune to motion, and thus feature QRS complexes that can be measured easily. They serve as fiducial markers for analyzing the RED/IR (PPG) waveforms which, unlike the ECG waveform, are strongly affected by motion.

FIG. 12B shows the IR(PPG) from dashed box 70 in FIG. 12A, which is measured when the patient is not moving. In this case, the waveform features a smooth, systematic rise time that is relatively easy to process with first and second derivative tests to determine its peak (indicated by marker 73) and foot (indicated by marker 72). Typically sub-ratios are only calculated between these markers 72, 73, as they are characterized by a relatively large amplitude change in the RED/IR(PPG) and are more indicative of a patient's actual SpO2 value than sub-ratios calculated in the second half of the waveform, characterized by a relatively gradual decrease in intensity. A single sub-ratio is calculated from both the RED/IR(PPG) waveforms for each time interval cc, as indicated by the dashed lines 78. FIG. 12C shows the resulting sub-ratios, indicated as dark circles with values of RoR(n) in the graph; the values of each of these data points are indicated below by equation (10):

$$RoR(n) = \frac{\left[\frac{RED(PPG:n+\alpha) - RED(PPG:n)}{RED(PPG:n+\alpha/2) + RED(DC) - AMBIENT(DC)}\right]}{\left[\frac{IR(PPG:n+\alpha) - IR(PPG:n)}{IR(PPG:n+\alpha/2) + IR(DC) - AMBIENT(DC)}\right]} \quad (10)$$

where RED/IR(DC) and AMBIENT(DC) are assumed to be constant throughout the entire pulse, and are described above.

Because the patient is not moving, the sub-ratios in FIG. 12C are relatively constant and show little variation in the graph. They can be statistically processed with a variety of statistical techniques, some of which are described in the above-mentioned reference, to determine an 'effective RoR' for each pulse in the RED/IR(PPG) waveforms. For example, each value of RoR(n) from equation (10) can be processed with a weighted average defined by wt(n) to determine the effective RoR, as shown below in equation (11):

$$\text{effective } RoR = \frac{\sum_{n \to foot}^{n \to peak} RoR(n) * wt(n)}{\sum_{n \to foot}^{n \to peak} wt(n)} \quad (11)$$

In one embodiment, each weight wt(n) is determined by comparing an SpO2 calculated from its corresponding RoR (n) to a preceding value for SpO2 and determining the weight based on the correlation. For example, if the preceding value for SpO2 is 98% O2, a value for SpO2 in the range of 70-80% O2 calculated from RoR(n) is likely erroneous; the RoR(n) is therefore give a relatively low weight wt(n). Additionally, a relatively large change in the RED/IR(PPG) amplitude during the sub-ratio measurement period n typically indicates that the corresponding value of RoR(n) has a relatively high accuracy. Such values are thus given a relatively high weight wt(n). In general, a number of established statistical techniques can be used to weight the collection of RoR(n) values to generate the effective RoR, as defined above in equation (11).

In another embodiment, the collection of RoR(n) values, such as those shown in FIG. 12C, are processed to determine an average and standard deviation. Values lying more than one standard deviation outside the average are then removed from the calculation, and the average is then recalculated. This technique, while typically less accurate than that indicated by equation (11), has the advantage of not requiring a series of weights with arbitrary definitions. In yet another embodiment, the collection of RoR(n) values are fit with a numerical function, such as a linear or non-linear function, and the effective RoR value can be estimated from the coefficients derived from the fit.

The dashed box 71 in FIG. 12A indicates a more complicated situation where profound motion is present in the ACC waveform; this, in turn, strongly influences the morphology of the RED/IR(PPG) waveforms, while having little affect on the ECG waveform. FIG. 12D shows the resulting IR(PPG) waveform, along with markers 74-77 indicating various points along the waveform where its foot and peak, in theory, could be determined. For example, application of the first and second first derivative tests could indicate two successive pulses, with the pulse between markers 74, 75 and 76, 77 yielding sub-ratios indicated, respectively, by the dashed lines 79A and 79B. The actual pulse, while still affected by motion-related noise, lies roughly between the markers 74, 75, and results in the sub-ratios calculated according to dashed lines 79A and shown in FIG. 12E. These sub-ratios are relatively noisy compared to those for the motion-free measurements indicated in FIG. 12C, but if processed with a weighted average like that indicated in equation (11) would likely yield a SpO2 value with suitable accuracy. In contrast, the 'pulse' between markers 76 and 77 is not caused by an actual heartbeat, and instead is an artifact resulting solely from motion. Thus, sub-ratios calculated between these markers 76, 77, as indicated by dashed lines 79B, result in artificial data points characterized by a large variation, as shown in FIG. 12F. The presence of motion, as indicated by the ACC waveform, drives the algorithm to remove these data points from a SpO2 calculation, as they will not result in an accurate value.

FIGS. 13A-D show an alternate embodiment of the invention that uses PTT to estimate if a pulse is corrupted by noise, and if so deploys a 'matched filter' to process both the RED/IR(PPG) waveforms to maximize signal-to-noise ratios of the pulses therein. With this embodiment the body-worn monitor can determine accurate SpO2 and cNIBP values even when motion-related noise is present. To illustrate this approach, FIGS. 13A-C feature a series of graphs on its left-hand side that show: i) how PTT is calculated from the time separating a peak of the ECG QRS and corresponding foot of the IR(PPG) (FIG. 13A); 2) PTT measured from an unfiltered PPG waveform plotted as a function of heartbeat (13B); and 3) PTT measured from a PPG waveform processed with a matched filter, and plotted as a function of heartbeat (FIG. 13C). FIG. 13D, shown in the right-hand side of the figure, is a flowchart corresponding to these graphs that illustrates this two-part method for making measurements when motion-related noise is present. The flowchart, in particular, shows an alternative series of steps 105-111 for processing the ECG, RED/IR(PPG), and ACC waveforms that replace steps 37-41 in FIG. 7.

FIG. 13A shows PTT calculated from the time difference (ΔT) separating the ECG QRS and the foot of the IR(PPG) waveform. This waveform is typically used in place of the RED(PPG) because of its superior signal-to-noise ratio. As described above, the QRS features a sharp, easily measurable peak informally marking the beginning of the cardiac cycle. In this case the IR(PPG) waveform follows this feature by about 220 ms; its foot is typically calculated by taking the second derivative of the waveform after performing some initial filtering to remove high-frequency noise, and then looking for a zero-point crossing. Referring to the flow chart shown in FIG. 13D, PTT is determined during step 105, and the process is repeated for consecutive heartbeats during a measurement interval, which is typically 10-20 seconds (step 106).

Once PTT is determined for each heartbeat in the measurement interval, a series of simple statistical filters are applied to detect pulse that may be corrupted by motion, and can thus potentially yield inaccurate values. In each step 17, for example, a simple average (AVE) and standard deviation (STDEV) are first calculated in a rolling manner, beginning at pulse N and extending out E pulses, where E is the number of pulses within the above-described interval. These statistical parameters can be updated for each subsequent pulse because of the rolling calculation. If the PTT value for the immediate pulse is more than 1 STDEV greater than the AVE for the preceding E pulses, as shown in step 108, it is flagged as potentially originating from a IR(PPG) that is corrupted by motion. This simple filtering process is shown schematically by the window 299 in FIG. 13B (data points outside this window 299 are flagged), and is indicated in the flow chart by step 107. A rapid change in PTT, however may be a real occurrence resulting from an actual fluctuation in blood pressure. Thus, the algorithm processes a corresponding ACC waveform generated by the accelerometer within the wrist-worn transceiver to determine if motion was indeed present during a time interval consistent with the PTT and its associated pulse (step 109). During step 109 it may be determined that motion exceeded a pre-determined coefficient (e.g. $M_{max}$) $M_{max}$ can be determined, for example form the power spectrum of time-dependent ACC waveforms that are known to corrupt RED/IR(PPG) waveforms, such as those shown in FIGS. 14-17 and described below. In this case the pulse is considered to be corrupted to an extent that neither PTT nor parameters associated with SpO2 (e.g. RED/IR(foot) and RED/IR(peak) can be accurately measured. The algorithm then returns to step 105 to resume calculating PTT form the DCG and IR(PPG) waveforms.

On the other hand, if motion is determined to be less than $M_{max}$ in step 109, then it is assumed that the PTT and corresponding pulse may be relatively uncorrupted, but are in need of additional filtering to potentially remove any noise that may have caused the abnormal PTT value. In this case, the pulse is filtered with a matched filter (also referred to as a 'North filter' when used in telecommunications). A matched filter is one which features an ideal frequency response that maximizes the signal-to-noise ratio for a given signal of a known shape in the time domain, particularly when the signal is subject to random, stochastic noise, such as that caused by motion. It involves mathematically convolving the immediate pulse with a known good pulse, or 'pulse template', using a mathematical cross-correlation algorithm. The cross-correlation yields filtering parameters that, once incorporated, represent a linear filter that in theory can optimize the signal-to-noise ratio of the immediate pulse. Specifically, for this application, a digital matched filter features an impulse response characterized by coefficients h(k). This function represents the time-reversed replica of the ideal signal to be detected, i.e. a pulse in the IR(PPG) measured during a time period where motion (as determined from the ACC waveform) is not present. Alternatively, h(k) can be determined from a standard, pre-programmed pulse, determined from waveforms measured from a large group of patients, which represents a known good pulse. In still other embodiments, this 'textbook' pre-programmed pulse is used initially in the matched filter, and then updated as subsequent known good pulses are measured from the patient. The subsequent known good pulse can be just a section of a pulse (e.g., near the foot or peak) that is known to be uncorrupted by noise. In any case, assuming this pulse is represented by the pulse template function $x_{tp}(k)$, then the coefficients h(k) of the matched filter are given by equation (13):

$$h(k)=x_{tp}(N-k-1), \text{ where } k=0,1,\ldots N-1 \quad (13)$$

The digital matched filter can be represented as a finite impulse response filter with a typical transversal structure, with the output y(i) of the filter shown in equation (14):

$$y(i)=\int_{k=0}^{k=N-1} h(k)x(k)dk \quad (14)$$

where x(k) are the samples of the immediate pulse (i.e. the input pulse requiring filtering), $x_{tp}(k)$ are the samples of the pulse template, N is the filter length, and i is a time shift index. From equations (13) and (14) it is evident that when the pulse template and the immediate pulse are identical, the output of the matched filter will be at its maximum value.

The matched filter improves the signal-to-noise ratio of the immediate input pulse by an amount that is directly related to the length of the filter (N). A filter length that is greater than or equal to the interval between heart beats is required; preferably the filter length is greater than multiple heart beats.

Upon completion of step 110, PTT is calculated from the filtered waveform, and the rolling AVE and STDEV statistics are recalculated (step 107). If the difference between the immediate PTT, as calculated from the filtered waveform, is within +/−1 STDEV of the average as per step 108, then the pulse is considered to be free of motion-related artifacts that may cause erroneous values of SpO2 and cNIBP. Such a case is shown graphically in FIG. 13C. At this point, as indicated by step 111, the ECG and RED/IR(PPG) are processed as per steps 42-46 and 48-50 in FIG. 7, and SpO2 and cNIBP are determined.

A patient's activity level, as characterized by ACC waveforms, can have a significant impact on the RED/IR(PPG) and ECG waveforms used to measure both SpO2 and cNIBP. For example, FIGS. 14-17 show time-dependent graphs of ECG, PPG, and ACC waveforms for a patient who is resting (FIG. 14), walking (FIG. 15), convulsing (FIG. 16), and falling (FIG. 17). Each graph includes a single ECG waveform 80, 85, 90, 95, PPG waveform 81, 86, 91, 96, and three ACC waveforms 82, 87, 92, 97. In all cases the PPG waveforms correspond to the IR(PPG) for the reasons described above. The ACC waveforms correspond to signals measured along the x, y, and z axes by a single accelerometer worn on the patient's wrist, similar to the accelerometer used to generate ACC waveforms in FIGS. 9B-11B.

Figure 14:
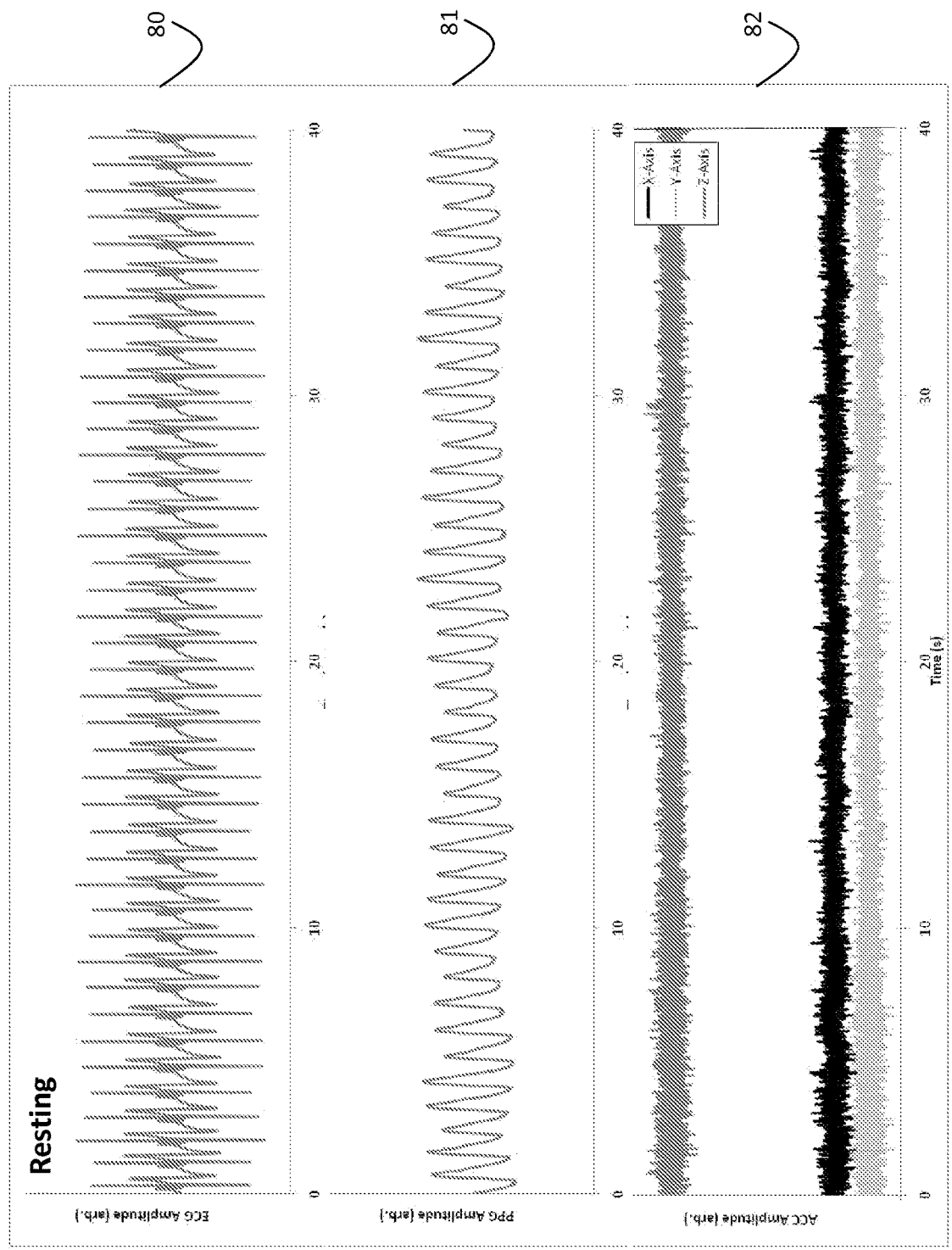
FIG. 14 shows a graph of time-dependent waveforms (ECG, PPG, and ACC) generated from a resting patient by, respectively, the ECG system, the optical system, and the accelerometer system of FIG. 1.

The figures indicate that time-dependent properties of both ECG 80, 85, 90, 95 and PPG 81, 86, 91, 96 waveforms can be strongly affected by certain patient activities, which are indicated by the ACC waveforms 82, 87, 92, 97. Accuracy of SpO2 and cNIBP calculated from these waveforms is therefore affected as well. FIG. 14, for example, shows data collected from a patient at rest. This state is clearly indicated by the ACC waveforms 82, which feature a relatively stable baseline along all three axes of the accelerometer. High-frequency noise in all the ACC waveforms 82, 87, 92, 97 shown in FIGS. 14-17 is due to electrical noise, and is not indicative of patient motion in any way. The ECG 80 and PPG 81 waveforms for this patient are correspondingly stable, thus allowing algorithms operating on the body-worn monitor to accurately determine SpO2 (from the PPG waveform 81), along with heart rate and respiratory rate (from the ECG waveform 80), cNIBP (from a PTT extracted from both the ECG 80 and PPG 81 waveforms). Based on the data shown in FIG. 14, algorithms operating on the body-worn monitor assume that vital signs calculated from a resting patient are relatively stable; the algorithm therefore deploys normal threshold criteria for alarms/alerts, described below in Table 3, for patients in this state.

Figure 15:
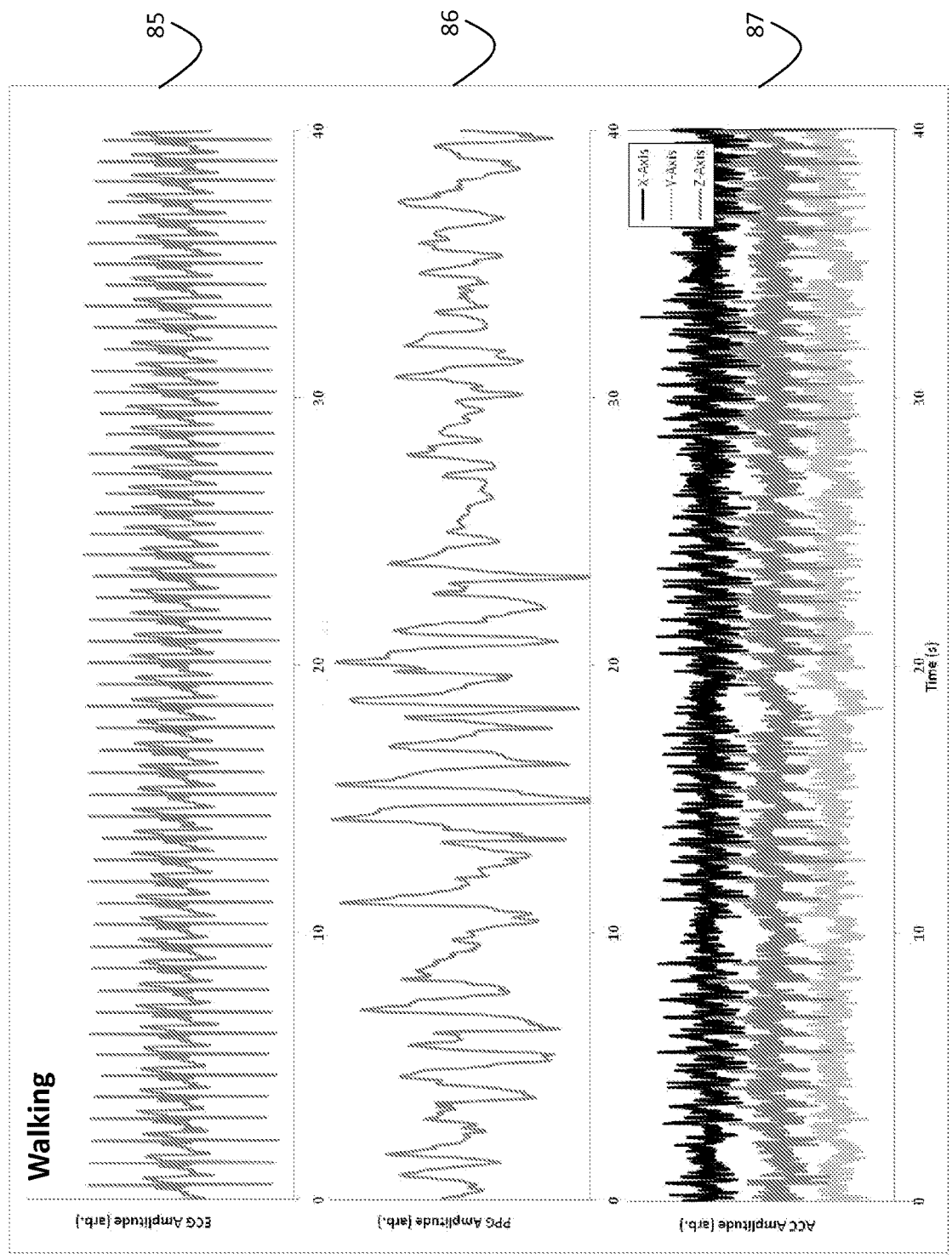
FIG. 15 shows a graph of time-dependent waveforms (ECG, PPG, and ACC) generated from a walking patient by, respectively, the ECG system, the optical system, and the accelerometer system of FIG. 1.

FIG. 15 shows ECG 85, PPG 86, and ACC 87 waveforms measured from a walking patient wearing the body-worn monitor. In this case, the ACC waveform 87 clearly indicates a quasi-periodic modulation, with each 'bump' in the modulation corresponding to a particular step. The 'gaps' in the modulation, shown near 10, 19, 27, and 35 seconds, correspond to periods when the patient stops walking and changes direction. Each bump in the ACC waveform includes relatively high-frequency features (other than those associated with electrical noise, described above) that correspond to walking-related movements of the patient's wrist.

The ECG waveform 85 measured from the walking patient is relatively unaffected by motion, other than indicating an increase in heart rate (i.e., a shorter time separation between neighboring QRS complexes) and respiratory rate (i.e. a higher frequency modulation of the waveform's envelope) caused by the patient's exertion. The PPG waveform 86, in contrast, is strongly affected by this motion, and pulses within it become basically immeasurable. Its distortion is likely due in part to a quasi-periodic change in light levels, caused by the patient's swinging arm, and detected by the photodetector within the thumb-worn sensor. Movement of the patient's arm additionally affects blood flow in the thumb and can cause the optical sensor to move relative to the patient's skin. The photodetector measures all of these artifacts, along with a conventional PPG signal (like the one shown in FIG. 14) caused by volumetric expansion in the underlying arteries and capillaries within the patient's thumb. The artifacts produce radiation-induced photocurrent that is difficult to distinguish from normal PPG signals used to calculate SpO2 and cNIBP. These vital signs are thus difficult or impossible to accurately measure when the patient is walking.

The body-worn monitor deploys multiple strategies to avoid generating false alarms/alerts during a walking activity state. As described in detail below, the monitor can detect this state by processing the ACC waveforms shown in FIG. 15 along with similar waveforms measured from the patient's bicep and chest. Walking typically elevates heart rate, respiratory rate, and blood pressure, and thus alarm thresholds for these parameters, as indicated by Table 2, are systematically and temporarily increased when this state is detected. Values above the modified thresholds are considered abnormal, and trigger an alarm. SpO2, unlike heart rate, respiratory rate and blood pressure, does not typically increase with exertion. Thus the alarm thresholds for this parameter, as shown in Table 2, do not change when the patient is walking. Body temperature measured with the body-worn monitor typically increases between 1-5%, depending on the physical condition of the patient and the speed at which they are walking.

TABLE 2 motion-dependent alarm/alert thresholds and heuristic rules for a walking patient

| Vital Sign | Motion State | Modified Threshold for Alarms/Alerts | Heuristic Rules for Alarms/Alerts |
| --- | --- | --- | --- |
| Blood Pressure (SYS, DIA) | Walking | Increase (+10-30%) | Ignore Threshold; Do Not Alarm/Alert |
| Heart Rate | Walking | Increase (+10-300%) | Use Modified Threshold; Alarm/Alert if Value Exceeds Threshold |
| Respiratory Rate | Walking | Increase (+10-300%) | Ignore Threshold; Do Not Alarm/Alert |
| SpO2 | Walking | No Change | Ignore Threshold; Do Not Alarm/Alert |
| Temperature | Walking | Increase (+10-30%) | Use Original Threshold; Alarm/Alert if Value Exceeds Threshold |

To further reduce false alarms/alerts, software associated with the body-worn monitor or remote monitor can deploy a series of 'heuristic rules' determined beforehand using practical, empirical studies. These rules, for example, can indicate that a walking patient is likely healthy, breathing, and characterized by a normal SpO2. Accordingly, the rules dictate that respiratory rate, blood pressure, and SpO2 values measured during a walking state that exceed predetermined alarm/alert thresholds are likely corrupted by artifacts; the system, in turn, does not sound the alarm/alert in this case. Heart rate, as indicated by FIG. 15, and body temperature can typically be accurately measured even when a patient is walking; the heuristic rules therefore dictate the modified thresholds listed in Table 2 be used to generate alarms/alerts for these particular vital signs.

Figure 16:
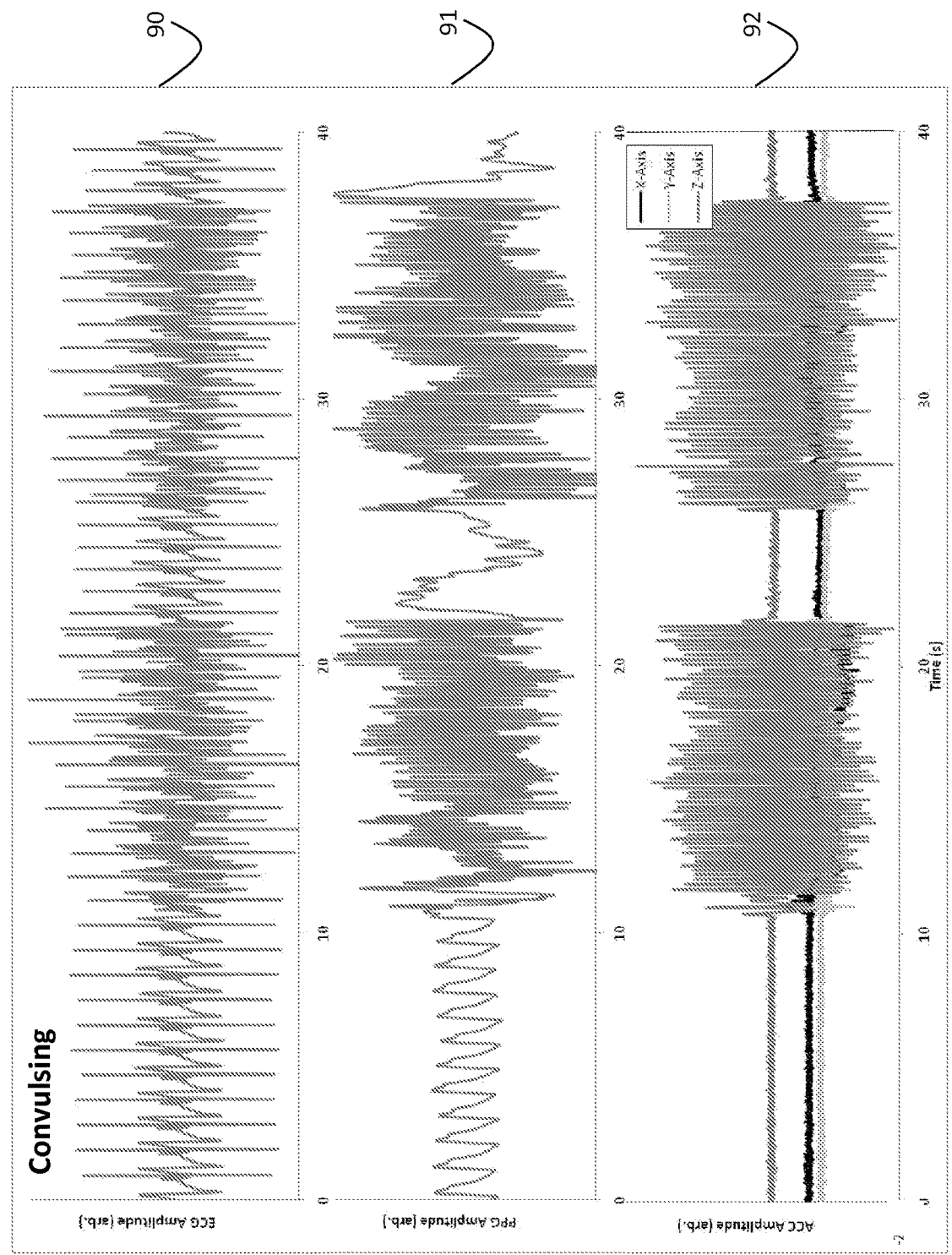
FIG. 16 shows a graph of time-dependent waveforms (ECG, PPG, and ACC) generated from a convulsing patient by, respectively, the ECG system, the optical system, and the accelerometer system of FIG. 1.
Figure 17:
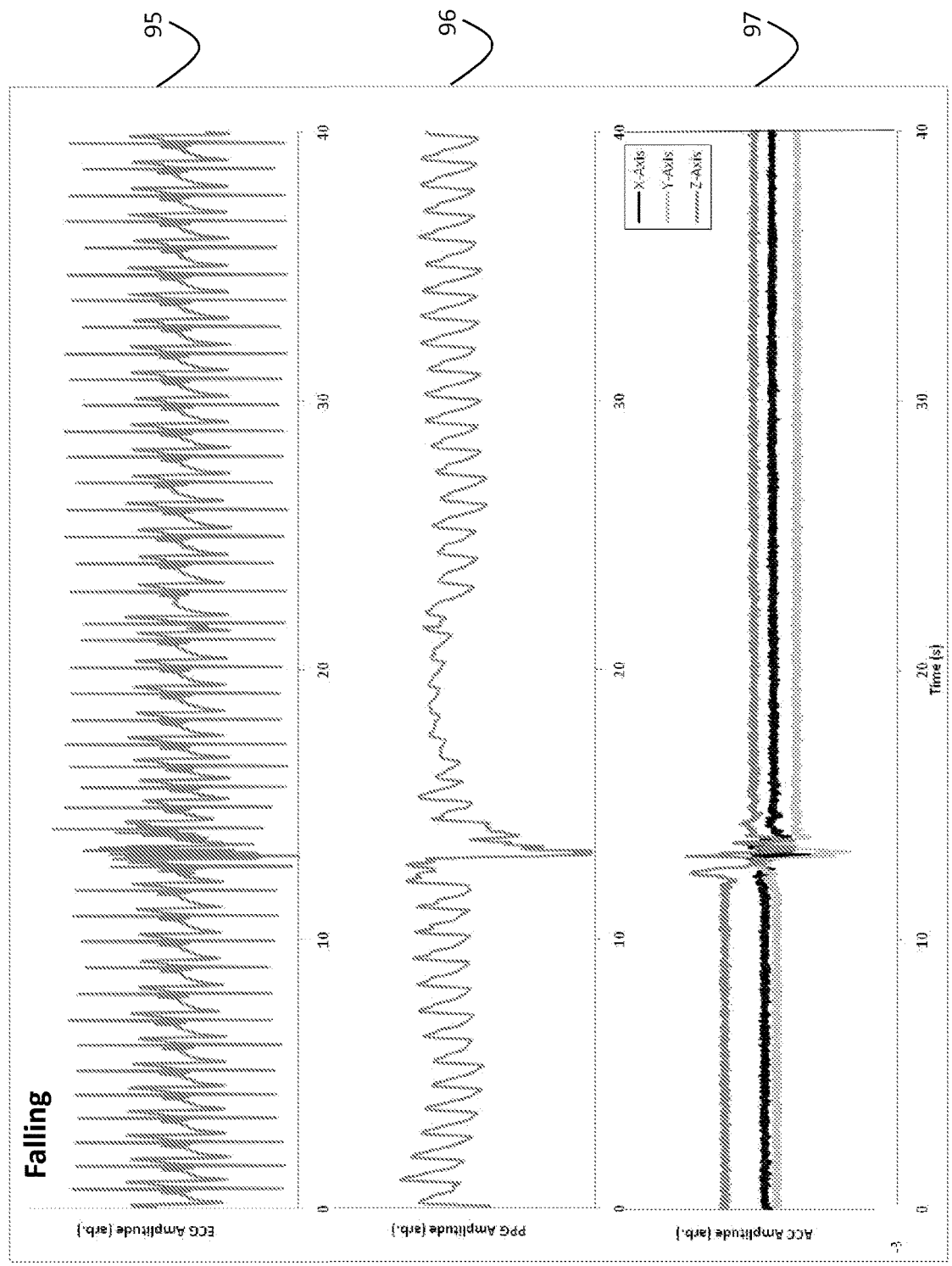
FIG. 17 shows a graph of time-dependent waveforms (ECG, PPG, and ACC) generated from a falling patient by, respectively, the ECG system, the optical system, and the accelerometer system of FIG. 1.

FIG. 16 shows ECG 90, PPG 91, and ACC 92 waveforms measured from a patient that is simulating convulsing by rapidly moving their arm back and forth. A patient undergoing a Gran-mal seizure, for example, would exhibit this type of motion. As is clear from the waveforms, the patient is at rest for the initial 10 seconds shown in the graph, during which the ECG 90 and PPG 91 waveforms are uncorrupted by motion. The patient then begins a period of simulated, rapid convulsing that lasts for about 12 seconds. A brief 5-second period of rest follows, and then convulsing begins for another 12 seconds or so.

Convulsing modulates the ACC waveform 92 due to rapid motion of the patient's arm, as measured by the wrist-worn accelerometer. This modulation is strongly coupled into the PPG waveform 91, likely because of the phenomena described above, i.e.: 1) ambient light coupling into the oximetry probe's photodiode; 2) movement of the photodiode relative to the patient's skin; and 3) disrupted blow flow underneath the probe. Note that from about 23-28 seconds the ACC waveform 92 is not modulated, indicating that the patient's arm is at rest. During this period the ambient light is constant and the optical sensor is stationary relative to the patient's skin. But the PPG waveform 91 is still strongly modulated, albeit at a different frequency than the modulation that occurred when the patient's arm was moving, and the pulses therein are difficult to resolve. This indicates that the disrupted blood flow underneath the optical sensor continues even after the patient's arm stops moving. Using this information, both ECG and PPG waveforms similar to those shown in FIG. 16 can be analyzed in conjunction with ACC waveforms measured from groups of stationary and moving patients. These data can then be analyzed to estimate the effects of specific motions and activities on the ECG and PPG waveforms, and then deconvolute these factors using known mathematical techniques to effectively remove any motion-related artifacts. The deconvoluted ECG and PPG waveforms can then be used to calculate vital signs, as described in detail below.

The ECG waveform 90 is modulated by the patient's arm movement, but to a lesser degree than the PPG waveform 91. In this case, modulation is caused primarily by electrical 'muscle noise' instigated by the convulsion and detected by the ECG electrodes, and well as by convulsion-induced motion in the ECG cables and electrodes relative to the patient's skin. Such motion is expected to have a similar affect on temperature measurements, which are determined by a sensor that also includes a cable.

Table 3, below, shows the modified threshold values and heuristic rules for alarms/alerts generated by a convulsing patient. In general, when a patient experiences convulsions, such as those simulated during the two 12-second periods in FIG. 16, it is virtually impossible to accurately measure any vital signs from the ECG 90 and PPG 91 waveforms. For this reason the threshold values corresponding to each vital sign are not adjusted when convulsions are detected. Heart rate determined from the ECG waveform, for example, is typically erroneously high due to high-frequency convulsions, and respiratory rate is immeasurable from the distorted waveform. Strong distortion of the optical waveform also makes both SpO2 and PPT-based cNIBP difficult or impossible to measure. For this reason, algorithms operating on either the body-worn monitor or a remote monitor will not generate alarms/alerts based on vital signs when a patient is convulsing, as these vital signs will almost certainly be corrupted by motion-related artifacts.

TABLE 3 motion-dependent alarm/alert thresholds and heuristic rules for a convulsing patient

| Vital Sign | Motion State | Modified Threshold for Alarms/Alerts | Heuristic Rules for Alarms/Alerts |
| --- | --- | --- | --- |
| Blood Pressure (SYS, DIA) | Convulsing | No Change | Ignore Threshold; Generate Alarm/Alert Because of Convulsion |
| Heart Rate | Convulsing | No Change | Ignore Threshold; Generate Alarm/Alert Because of Convulsion |
| Respiratory Rate | Convulsing | No Change | Ignore Threshold; Generate Alarm/Alert Because of Convulsion |
| SpO2 | Convulsing | No Change | Ignore Threshold; Generate Alarm/Alert Because of Convulsion |
| Temperature | Convulsing | No Change | Ignore Threshold; Generate Alarm/Alert Because of Convulsion |

Table 3 also shows the heuristic rules for convulsing patients. Here, the overriding rule is that a convulsing patient needs assistance, and thus an alarm/alert for this patient is generated regardless of their vital signs (which, as described above, are likely inaccurate due to motion-related artifacts). The system always generates an alarm/alert for a convulsing patient.

FIG. 17 shows ECG 95, PPG 96, and ACC 97 waveforms measured from a patient that experiences a fall roughly 13 seconds into the measuring period. The ACC waveform 97 clearly indicates the fall with a sharp decrease in its signal, followed by a short-term oscillatory signal, due (literally) to the patient bouncing on the floor. After the fall, ACC waveforms 97 associated with the x, y, and z axes also show a prolonged decrease in value due to the resulting change in the patient's posture. In this case, both the ECG 95 and PPG 96 waveforms are uncorrupted by motion prior to the fall, but basically immeasurable during the fall, which typically takes only 1-2 seconds. Specifically, this activity adds very high frequency noise to the ECG waveform 95, making it impossible to extract heart rate and respiratory rate during this short time period. Falling causes a sharp drop in the PPG waveform 96, presumably for the same reasons as described above (i.e. changes in ambient light, sensor movement, and disruption of blood flow) for walking and convulsing, making it difficult to measure SpO2 and cNIBP.

After a fall, both the ECG 95 and PPG 96 waveforms are free from artifacts, but both indicate an accelerated heart rate and relatively high heart rate variability for roughly 10 seconds. During this period the PPG waveform 96 also shows distortion and a decrease in pulse amplitude. Without being bound to any theory, the increase in heart rate may be due to the patient's baroreflex, which is the body's haemostatic mechanism for regulating and maintaining blood pressure. The baroreflex, for example, is initiated when a patient begins faint. In this case, the patient's fall may cause a rapid drop in blood pressure, thereby depressing the baroreflex. The body responds by accelerating heart rate (indicated by the ECG waveform 95) and increasing blood pressure (indicated by a reduction in PTT, as measured from the ECG 95 and PPG 96 waveforms) in order to deliver more blood to the patient's extremities.

Table 4 shows the heuristic rules and modified alarm thresholds for a falling patient. Falling, similar to convulsing, makes it difficult to measure waveforms and the vital signs calculated from them. Because of this and the short time duration associated with a fall, alarms/alerts based on vital signs thresholds are not generated during an actual falls. However, this activity, optionally coupled with prolonged stationary period or convulsion (both determined from the following ACC waveform), generates an alarm/alert according to the heuristic rules.

TABLE 4 motion-dependent alarm/alert thresholds and heuristic rules for a falling patient

| Vital Sign | Motion State | Modified Threshold for Alarms/Alerts | Heuristic Rules for Alarms/Alerts |
|---|---|---|---|
| Blood Pressure (SYS, DIA) | Falling | No Change | Ignore Threshold; Generate Alarm/Alert Because of Fall |
| Heart Rate | Falling | No Change | Ignore Threshold; Generate Alarm/Alert Because of Fall |
| Respiratory Rate | Falling | No Change | Ignore Threshold; Generate Alarm/Alert Because of Fall |
| SpO2 | Falling | No Change | Ignore Threshold; Generate Alarm/Alert Because of Fall |
| Temperature | Falling | No Change | Ignore Threshold; Generate Alarm/Alert Because of Fall |

Figure 18:
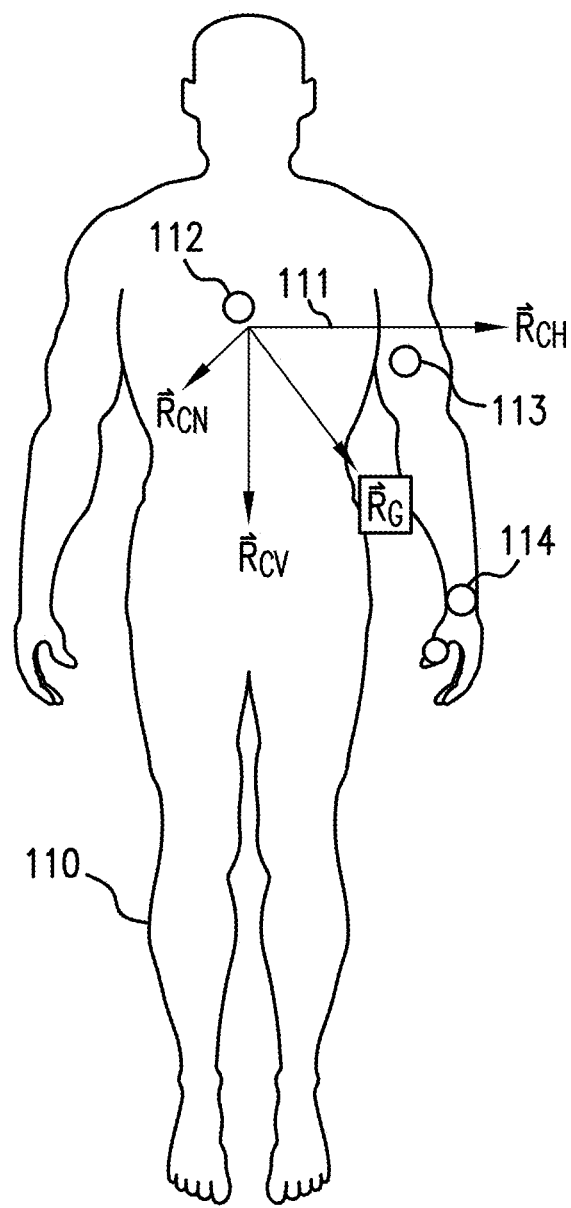
FIG. 18 is a schematic drawing of a coordinate system assigned to a patient wearing three accelerometers and a pulse oximeter probe.

In addition to activity level, as described above and indicated in FIGS. 14-17, a patient's posture can influence how the above-described system generates alarms/alerts from SpO2, cNIBP, and other vital signs. For example, the alarms/alerts related to both SpO2 and cNIBP may vary depending on whether the patient is lying down or standing up. FIG. 18 indicates how the body-worn monitor can determine motion-related parameters (e.g. degree of motion, posture, and activity level) from a patient 110 using time-dependent ACC waveforms continuously generated from the three accelerometers 112, 113, 114 worn, respectively, on the patient's chest, bicep, and wrist. As described above with reference to FIGS. 9A,B-11A,B, motion of the patient's hand is most likely to affect measurement of both RED/IR (PPG) waveforms, and this can best be detected using the accelerometer 114 affixed to the wrist. The height of the patient's arm can affect the cNIBP measurement, as blood pressure can vary significantly due to hydrostatic forces induced by changes in arm height. Moreover, this phenomenon can be detected and exploited to calibrate the cNIBP measurement, as described in detail in the above-referenced patent application, the contents of which have been previously incorporated by reference: BODY-WORN VITAL SIGN MONITOR WITH SYSTEM FOR DETECTING AND ANALYZING MOTION (U.S. Ser. No. 12/469,094; filed May 20, 2009). As described in this document, arm height can be determined using DC signals from the accelerometers 113, 114 disposed, respectively, on the patient's bicep and wrist. Posture, in contrast, can be exclusively determined by the accelerometer 112 worn on the patient's chest. An algorithm operating on the wrist-worn transceiver extracts DC values from waveforms measured from this accelerometer and processes them with an algorithm described below to determine posture.

Specifically, posture is determined for a patient 110 using angles determined between the measured gravitational vector and the axes of a torso coordinate space 111. The axes of this space 111 are defined in a three-dimensional Euclidean space where $\vec{R}_{CV}$ is the vertical axis, $\vec{R}_{CH}$ is the horizontal axis, and $\vec{R}_{CN}$ is the normal axis. These axes must be identified relative to a 'chest accelerometer coordinate space' before the patient's posture can be determined.

The first step in determining a patient's posture is to identify alignment of $\vec{R}_{CV}$ in the chest accelerometer coordinate space. This can be determined in either of two approaches. In the first approach, $\vec{R}_{CV}$ is assumed based on a typical alignment of the body-worn monitor relative to the patient. During a manufacturing process, these parameters are then preprogrammed into firmware operating on the wrist-worn transceiver. In this procedure it is assumed that accelerometers within the body-worn monitor are applied to each patient with essentially the same configuration. In the second approach, $\vec{R}_{CV}$ is identified on a patient-specific basis. Here, an algorithm operating on the wrist-worn transceiver prompts the patient (using, e.g., video instruction operating on the wrist-worn transceiver, or audio instructions transmitted through a speaker) to assume a known position with respect to gravity (e.g., standing up with arms pointed straight down). The algorithm then calculates $\vec{R}_{CV}$ from DC values corresponding to the x, y, and z axes of the chest accelerometer while the patient is in this position. This case, however, still requires knowledge of which arm (left or right) the monitor is worn on, as the chest accelerometer coordinate space can be rotated by 180 degrees depending on this orientation. A medical professional applying the monitor can enter this information using the GUI, described above. This potential for dual-arm attachment requires a set of two pre-determined vertical and normal vectors which are interchangeable depending on the monitor's location. Instead of manually entering this information, the arm on which the monitor is worn can be easily determined following attachment using measured values from the chest accelerometer values, with the assumption that $\vec{R}_{CV}$ is not orthogonal to the gravity vector.

The second step in the procedure is to identify the alignment of $\vec{R}_{CN}$ in the chest accelerometer coordinate space. The monitor can determine this vector, similar to how it determines $\vec{R}_{CV}$, with one of two approaches. In the first approach the monitor assumes a typical alignment of the chest-worn accelerometer on the patient. In the second approach, the alignment is identified by prompting the patient to assume a known position with respect to gravity. The monitor then calculates $\vec{R}_{CN}$ from the DC values of the time-dependent ACC waveform.

The third step in the procedure is to identify the alignment of $\vec{R}_{CH}$ in the chest accelerometer coordinate space. This vector is typically determined from the vector cross product of $\vec{R}_{CV}$ and $\vec{R}_{CN}$, or it can be assumed based on the typical alignment of the accelerometer on the patient, as described above.

A patient's posture is determined using the coordinate system described above and in FIG. 18, along with a gravitational vector $\vec{R}_G$ that extends normal from the patient's chest. The angle between $\vec{R}_{CV}$ and $\vec{R}_G$ is given by equation (14):

$$\theta_{VG}[n] = \arccos\left(\frac{\vec{R}_G[n]\cdot\vec{R}_{CV}}{\|\vec{R}_G[n]\|\|\vec{R}_{CV}\|}\right) \quad (14)$$

where the dot product of the two vectors is defined as:

$$\vec{R}_G[n]\cdot\vec{R}_{CV}=(y_{Cx}[n]\times r_{CVx})+(y_{Cy}[n]\times r_{CVy})+(y_{Cz}[n]\times r_{CVz}) \quad (15)$$

The definition of the norms of $\vec{R}_G$ and $\vec{R}_{CV}$ are given by equations (16) and (17):

$$\|\vec{R}_G[n]\|=\sqrt{(y_{Cx}[n])^2+(y_{Cy}[n])^2+(y_{Cz}[n])^2} \quad (16)$$

$$\|\vec{R}_{CV}\|=\sqrt{(r_{CVx})^2+(r_{CVy})^2+(r_{CVz})^2} \quad (17)$$

As indicated in equation (18), the monitor compares the vertical angle $\theta_{VG}$ to a threshold angle to determine whether the patient is vertical (i.e. standing upright) or lying down:

if $\theta_{VG} \leq 45°$ then Torso State=0, the patient is upright (18)

If the condition in equation (18) is met the patient is assumed to be upright, and their torso state, which is a numerical value equated to the patient's posture, is equal to 0. The patient is assumed to be lying down if the condition in equation (18) is not met, i.e. $\theta_{VG}>45$ degrees. Their lying position is then determined from angles separating the two remaining vectors, as defined below.

The angle $\theta_{NG}$ between $\vec{R}_{CN}$ and $\vec{R}_G$ determines if the patient is lying in the supine position (chest up), prone position (chest down), or on their side. Based on either an assumed orientation or a patient-specific calibration procedure, as described above, the alignment of $\vec{R}_{CN}$ is given by equation (19), where i, j, k represent the unit vectors of the x, y, and z axes of the chest accelerometer coordinate space respectively:

$$\vec{R}_{CN}=r_{CNx}\hat{i}+r_{CNy}\hat{j}+r_{CNz}\hat{k} \quad (19)$$

The angle between $\vec{R}_{CN}$ and $\vec{R}_G$ determined from DC values extracted from the chest accelerometer ACC waveform is given by equation (20):

$$\theta_{NG}[n] = \arccos\left(\frac{\vec{R}_G[n]\cdot\vec{R}_{CN}}{\|\vec{R}_G[n]\|\|\vec{R}_{CN}\|}\right) \quad (20)$$

The body-worn monitor determines the normal angle $\theta_{NG}$ and then compares it to a set of predetermined threshold angles to determine which position the patient is lying in, as shown in equation (21):

if $\theta_{NG} \leq 35°$ then Torso State=1, the patient is supine if $\theta_{NG} \geq 135°$ then Torso State=2, the patient is prone (21)

If the conditions in equation (21) are not met then the patient is assumed to be lying on their side. Whether they are lying on their right or left side is determined from the angle calculated between the horizontal torso vector and measured gravitational vectors, as described above.

The alignment of $\vec{R}_{CH}$ is determined using either an assumed orientation, or from the vector cross-product of $\vec{R}_{CV}$ and $\vec{R}_{CN}$ as given by equation (22), where i, j, k represent the unit vectors of the x, y, and z axes of the accelerometer coordinate space respectively. Note that the orientation of the calculated vector is dependent on the order of the vectors in the operation. The order below defines the horizontal axis as positive towards the right side of the patient's body.

$$\vec{R}_{CH}=r_{CVx}\hat{i}+r_{CVy}\hat{j}+r_{CVz}\hat{k}=\vec{R}_{CV}\times\vec{R}_{CN} \quad (22)$$

The angle $\theta_{HG}$ between $\vec{R}_{CH}$ and $\vec{R}_G$ is determined using equation (23):

$$\theta_{HG}[n] = \arccos\left(\frac{\vec{R}_G[n]\cdot\vec{R}_{CH}}{\|\vec{R}_G[n]\|\|\vec{R}_{CH}\|}\right) \quad (23)$$

The monitor compares this angle to a set of predetermined threshold angles to determine if the patient is lying on their right or left side, as given by equation (24):

if $\theta_{HG} \geq 90°$ then Torso State=3, the patient is on their right side if $\theta_{NG} < 90°$ then Torso State=4, the patient is on their left side (24)

Table 5 describes each of the above-described postures, along with a corresponding numerical torso state used to render, e.g., a particular icon:

TABLE 5 postures and their corresponding torso states

| Posture | Torso State |
|---|---|
| Upright | 0 |
| supine: lying on back | 1 |
| prone: lying on chest | 2 |
| lying on right side | 3 |
| lying on left side | 4 |
| undetermined posture | 5 |

Figure 19A:
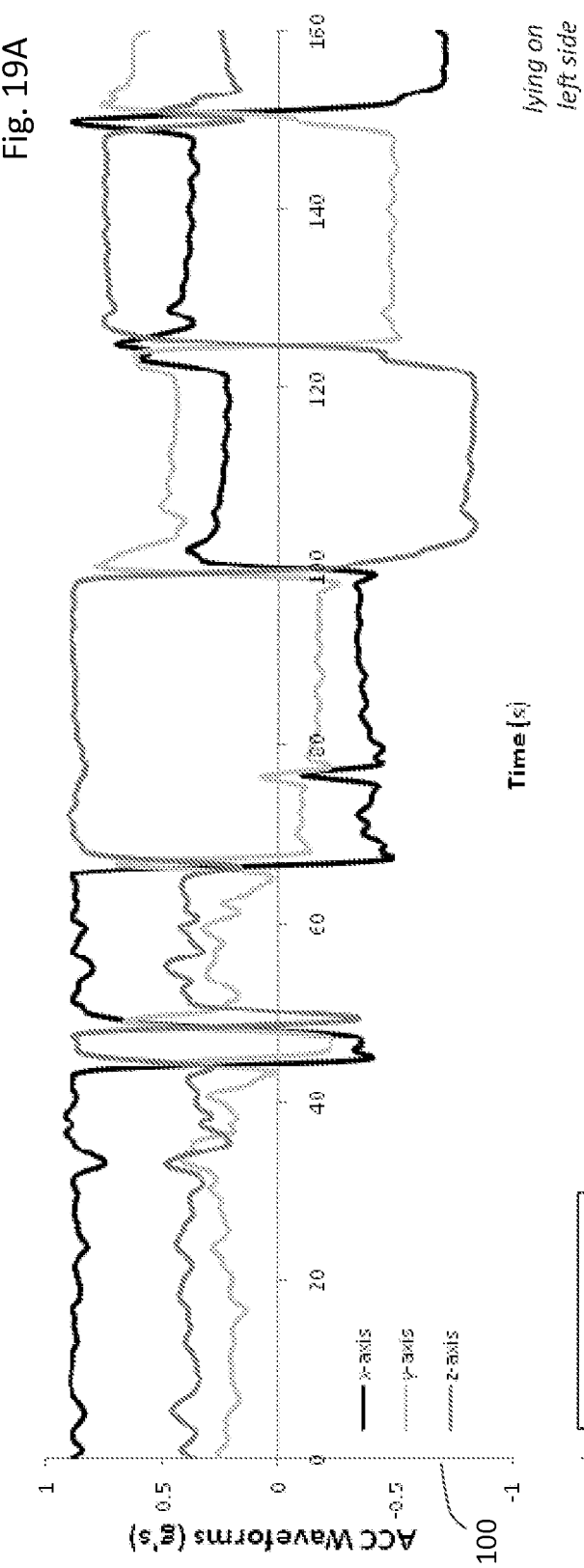
FIG. 19A is a graph showing time-dependent ACC waveforms corresponding to different posture states and measured with an accelerometer positioned on a patient's chest.
Figure 19B:
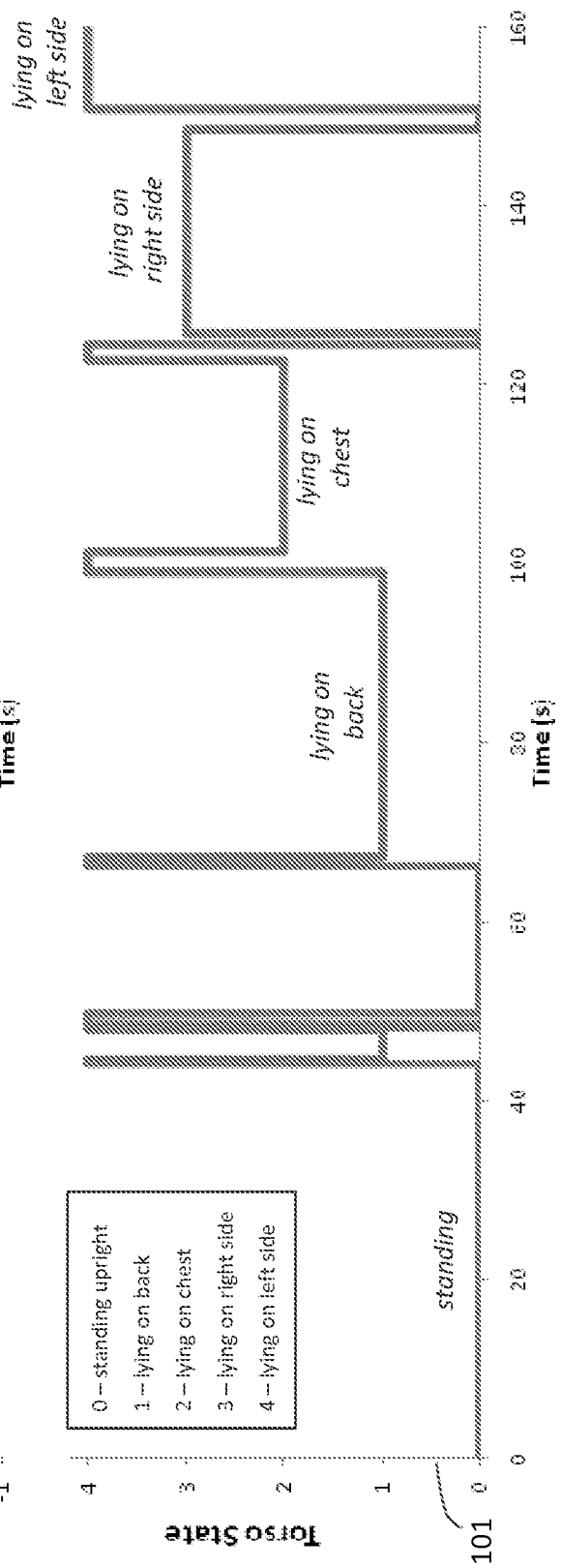
FIG. 19B is a graph showing posture states calculated using the time-dependent ACC waveforms of FIG. 19A and a mathematical model for determining a patient's posture.

FIGS. 19A and 19B show, respectively, graphs of time-dependent ACC waveforms 100 measured along the x, y, and z-axes, and the torso states (i.e. postures) 101 determined from these waveforms for a moving patient, as described above. As the patient moves, the DC values of the ACC waveforms measured by the chest accelerometer vary accordingly, as shown by the graph 100 in FIG. 19A. The body-worn monitor processes these values as described above to continually determine $\vec{R}_G$ and the various quantized torso states for the patient, as shown in the graph 101 in FIG. 19B. The torso states yield the patient's posture as defined in Table 5. For this study the patient rapidly alternated between standing, lying on their back, chest, right side, and left side within a time period of about 160 seconds. As described above, different alarm/alert conditions (e.g. threshold values) for vital signs can be assigned to each of these postures, or the specific posture itself may result in an alarm/alert. Additionally, the time-dependent properties of the graph 101 can be analyzed (e.g. changes in the torso states can be counted) to determine, for example, how often the patient moves in their hospital bed. This number can then be equated to various metrics, such as a 'bed sore index' indicating a patient that is so stationary in their bed that lesions may result. Such a state could then be used to trigger an alarm/alert to the supervising medical professional.

FIG. 20 is a schematic drawing showing time-dependent current pulses 120, 121 used to drive the red and infrared LEDs in the pulse oximeter probe. During a measurement of SpO2, both the red and infrared LEDs are alternately driven with separate current pulses 120, 121 having a magnitude ranging between about 10 and 40 mA, which can be controlled dynamically with a closed-loop system to maximize the RED/IR(PPG) signal strength without saturating it, as described in more detail with regard to FIG. 22. To minimize power consumption, current pulses 120, 121 typically drive the LEDs at 500 Hz for a time period of 100 µs, yielding a duty cycle of 5%. The separation between neighboring current pulses for the LEDs is typically maximized according to the drive frequency, and as indicated by the dashed line 122 is 1 ms for a drive frequency of 500 Hz.

Figure 21:
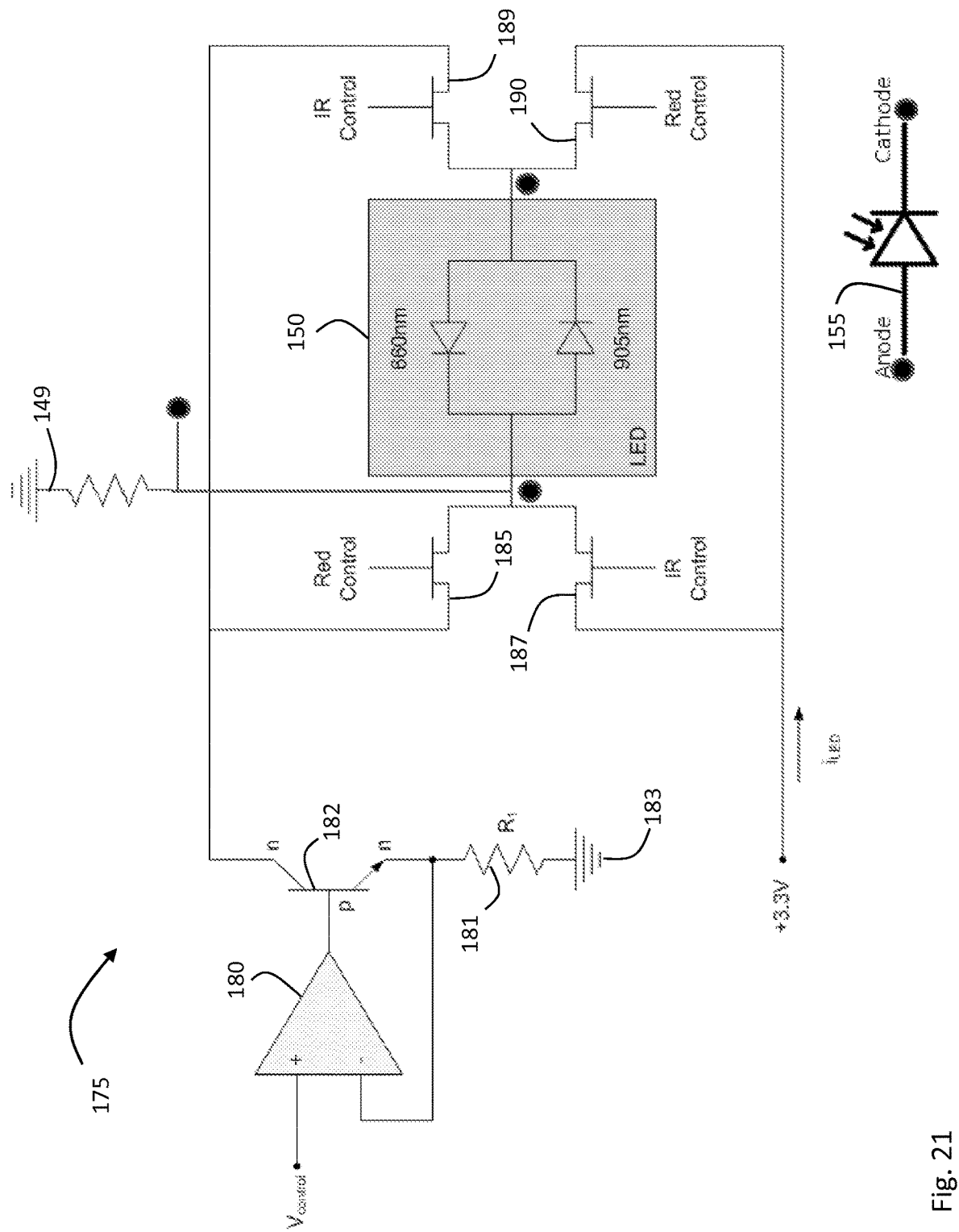
FIG. 21 is an electrical diagram of a circuit used to drive the 660 nm and 905 nm LEDs according to the timing diagram shown in FIG. 20.

FIG. 21 shows a circuit 175 that generates the current pulses 10, 121 described above for powering the LEDs. The circuit 175 features an operational amplifier 180 that receives a control voltage ($V_{control}$) on its gating pin. The amplifier 180 is connected to a transistor 12 and resistor 181 that, along with a supply voltage of 3.3V (typically from a li:ion battery), generate the current pulses 120, 121 used to driva dual red/infrared LED 150 operating at two wavelengths (660/905 nm). The wavelength of the LED depends on the direction that it is biased. To select the biasing direction, the circuit 175 features red control lines 185, 190 and infrared (IR) control lines 187, 189 that connect directly to I/O lines in a microprocessor within the wrist-worn transceiver. During a measurement, the current pulses 120, 121 flow from the 3.3V supply voltage, across one direction of the LED 150, and ultimately through the transistor 182 and resistor 181 to ground 183. The LED 150 is biased in fa forward direction when control lines 185, 190 are toggled closed, thereby supplying a drive current pulse of $i_{LED}=V_{control}/R1$ to LED 150 to generate red radiation. Voltage flowing across the LED 150 is also decreased because it is a diode. In this case, the IR control lines 187, 189 for infrared radiation are left open. As shown in FIG. 20, this configuration persists for 100 µs, after which the red control lines 185, 190 are switched closed, and the infrared (IR) control lines 187, 189 are switched open. This biases the LED 150 in a backwards direction to generate infrared radiation according to the above-directed drive current. The alternating process is repeated at 500 Hz. In both cases, red and infrared radiation that transmits through the patient's thumb is detected by photodetector 155 that features anode and cathode. Each black dot in FIG. 20 (five in total) indicates a separate wire in the cable that connects the oximeter probe to the wrist-worn transceiver. The wire associated with the cathode of the photodiode 155 also functions as a shield for the remaining 4 wires.

As shown in FIGS. 21 and 22, a thumb-worn pulse oximeter probe 294 contains the red/infrared LED 150 along with a gain resistor 149 indicating the specific wavelengths of both the red and infrared radiation. During a measurement, the microprocessor in the wrist-worn transceiver determines the value of the resistor 149 by monitoring a voltage drop across it; this value, in turn, is compared to a value stored in memory to select the appropriate coefficients relating RoR to SpO2. The probe 294 generates alternating red and infrared radiation according to the timing diagram in FIG. 20 that passes through the base of the patient's thumb 151, where it is partially absorbed by underlying vasculature according to the patient's heart rate and SpO2 values. Radiation that transmits through the thumb 151 illuminates a photodiode 155 that, in response, generates a photocurrent varying in magnitude with the degree of optical absorption in the patient's thumb. An amplifier circuit 140 beginning with a transimpedance amplifier 156 receives the photocurrent and converts it to a corresponding voltage which is then amplified and filtered to generate the RED/IR(PPG) waveforms used to determine SpO2 and cNIBP.

The amplifier circuit 140 features separate channels for amplifying and filtering signals corresponding to red radiation, infrared radiation, and ambient light detected by the photodiode 155 when the LED is not biased to generate radiation. This occurs, for example, during the time periods shown in FIG. 20 when neither the red or infrared LED is driven. Once detected, the degree of ambient light can be subtracted from both the red and infrared signals to improve their resultant signal-to-noise ratio. The amplifier channel corresponding to red radiation is activated by a sample-and-hold integrated circuit 157 that is controlled by the same control lines 185, 190 that drive the red LED, as shown in FIG. 20. When the red LED is driven, the sample-and-hold circuit 157 is switched on, while similar components 164, 172 corresponding to the infrared signals and ambient light are switched off. The sample-and-hold circuit 157 samples and maintains an analog voltage from the transimpedance amplifier 156, which then passes through a low-pass filter 158 characterized by a 20 Hz cutoff. This filter removes any high-frequency noise (e.g. 60 Hz electrical noise) that is not related to the RED(PPG), and yields a preliminary waveform that is digitized with an analog-to-digital converter 176, and processed as described above to generate a RED (DC) value. The preliminary waveform then passes through a high-pass filter 160 with a cutoff of 0.1 Hz to remove the DC portion and leave only the AC portion, which typically represents about 0.5-1% of the total signal magnitude. The AC portion is further amplified with a standard instrumentation amplifier 162 featuring a programmable gain that is controlled with a 1.65 reference voltage and a digital potentiometer (not shown in the figure; this component may be included directly in the instrumentation amplifier) featuring a variable resistance controlled by the microprocessor. The microprocessor selects the resistance (according to a predetermined binary command) and corresponding gain to maximize the dynamic range of the analog-to-digital converter 176. This process results in an amplified version of the RED(AC) signal, which is then digitized with the analog-to-digital converter 176 and then processed as described above.

The above-described filtering and amplification processes are repeated when the infrared LED and a sample-and-hold integrated circuit 164 corresponding to the infrared channel are activated with infrared I/O control lines 187, 189. The low-pass 166 and high-pass 168 filters corresponding to this channel are identical to those used for the red channel.

The instrumentation amplifier 170 is also identical, but is controlled by a separate digital potentiometer to have a unique, uncoupled gain. This is because the IR(PPG) typically has a relatively large amplitude, and thus requires less amplification, than the RED(PPG). The channel corresponding to ambient light only requires processing of DC signals, and thus includes a sample-and-hold integrated circuit 172 that passes an analog voltage to a low-pass filter 174 featuring a 20 Hz cutoff. The filtered value corresponding to ambient light is then digitized with the analog-to-digital converter and then processed as described above.

FIGS. 23A and 23B show how the body-worn monitor 298 described above attaches to a patient 270. These figures show two configurations of the system: FIG. 23A shows the system used during the indexing portion of the Composite Technique, and includes a pneumatic, cuff-based system 285, while FIG. 23B shows the system used for subsequent SpO2 and cNIBP measurements. The indexing measurement typically takes about 60 seconds, and is typically performed once every 4-8 hours. Once the indexing measurement is complete the cuff-based system 285 is typically removed from the patient. The remainder of the time system 298 performs the SpO2 and cNIBP measurements.

Figure 24:
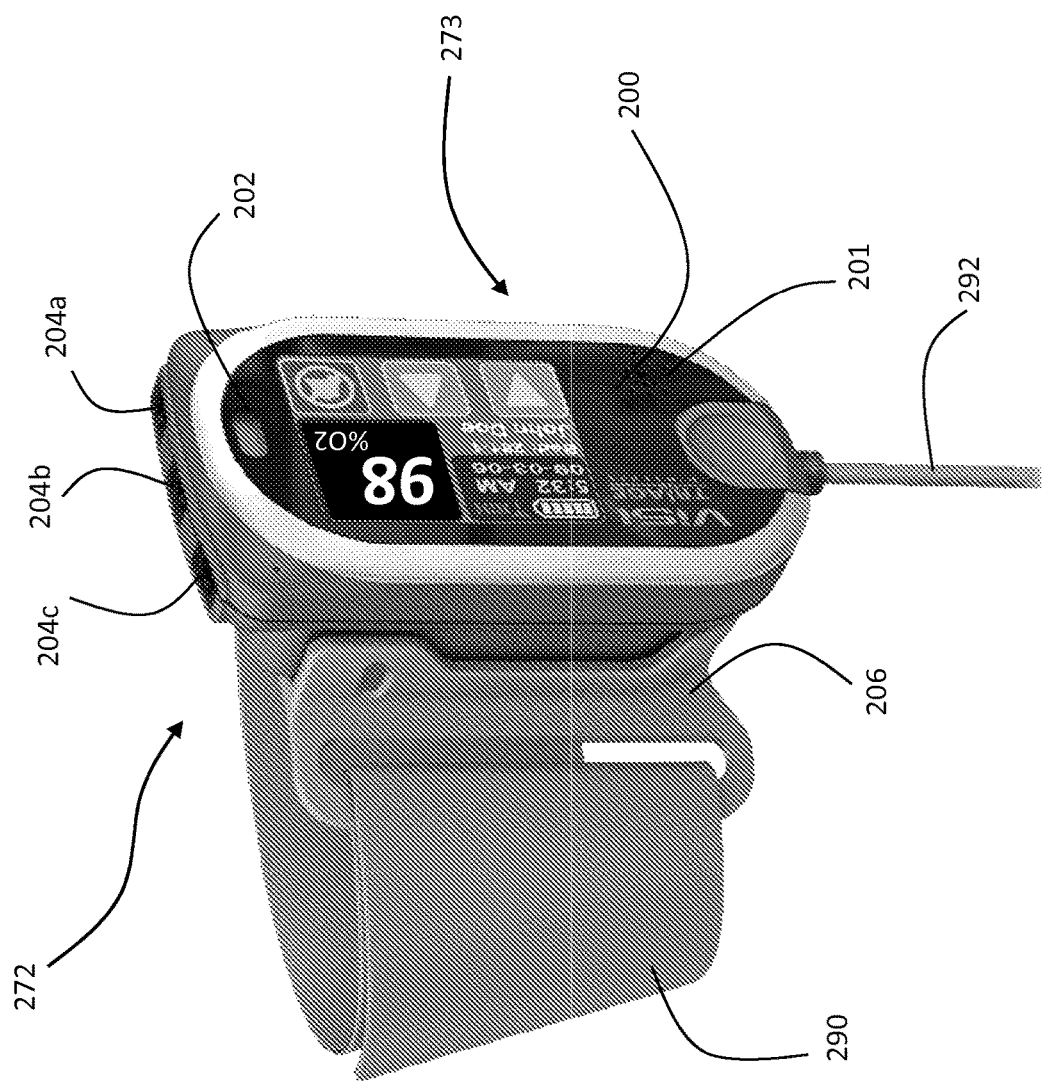
FIG. 24 shows an image of the wrist-worn transceiver featured in the body-worn monitor of FIGS. 23A and 23B.

The body-worn monitor 190 features a wrist-worn transceiver 272, described in more detail in FIG. 24, featuring a touch panel interface 273 that displays SpO2, blood pressure values and other vital signs. A wrist strap 290 affixes the transceiver 272 to the patient's wrist like a conventional wristwatch. A flexible cable 292 connects the transceiver 272 to a pulse oximeter probe 294 that wraps around the base of the patient's thumb. During a measurement, the probe 294 generates a time-dependent PPG waveform which is processed along with an ECG to measure cNIBP and SpO2. This provides an accurate representation of blood pressure in the central regions of the patient's body, as described above.

To determine ACC waveforms the body-worn monitor 190 features three separate accelerometers located at different portions on the patient's arm and chest. The first accelerometer is surface-mounted on a circuit board in the wrist-worn transceiver 272 and measures signals associated with movement of the patient's wrist. As described above, this motion can also be indicative of that originating from the patient's fingers, which will affect the SpO2 measurement. The second accelerometer is included in a small bulkhead portion 296 included along the span of the cable 282. During a measurement, a small piece of disposable tape, similar in size to a conventional bandaid, affixes the bulkhead portion 296 to the patient's arm. In this way the bulkhead portion 296 serves two purposes: 1) it measures a time-dependent ACC waveform from the mid-portion of the patient's arm, thereby allowing their posture and arm height to be determined as described in detail above; and 2) it secures the cable 286 to the patient's arm to increase comfort and performance of the body-worn monitor 190, particularly when the patient is ambulatory.

The cuff-based module 285 features a pneumatic system 276 that includes a pump, valve, pressure fittings, pressure sensor, analog-to-digital converter, microcontroller, and rechargeable Li:ion battery. During an indexing measurement, the pneumatic system 276 inflates a disposable cuff 284 and performs two measurements according to the Composite Technique: 1) it performs an inflation-based measurement of oscillometry to determine values for SYS, DIA, and MAP; and 2) it determines a patient-specific relationship between PTT and MAP. These measurements are described in detail in the above-referenced patent application entitled: 'VITAL SIGN MONITOR FOR MEASURING BLOOD PRESSURE USING OPTICAL, ELECTRICAL, AND PRESSURE WAVEFORMS' (U.S. Ser. No. 12/138,194; filed Jun. 12, 2008), the contents of which have been previously incorporated herein by reference.

The cuff 284 within the cuff-based pneumatic system 285 is typically disposable and features an internal, airtight bladder that wraps around the patient's bicep to deliver a uniform pressure field. During the indexing measurement, pressure values are digitized by the internal analog-to-digital converter, and sent through a cable 286 according to a CAN protocol, along with SYS, DIA, and MAP blood pressures, to the wrist-worn transceiver 272 for processing as described above. Once the cuff-based measurement is complete, the cuff-based module 285 is removed from the patient's arm and the cable 282 is disconnected from the wrist-worn transceiver 272. cNIBP is then determined using PTT, as described in detail above.

To determine an ECG, the body-worn monitor 190 features a small-scale, three-lead ECG circuit integrated directly into a bulkhead 274 that terminates an ECG cable 282. The ECG circuit features an integrated circuit that collects electrical signals from three chest-worn ECG electrodes 278a-c connected through cables 280a-c. The ECG electrodes 278a-c are typically disposed in a conventional 'Einthoven's Triangle' configuration which is a triangle-like orientation of the electrodes 278a-c on the patient's chest that features three unique ECG vectors. From these electrical signals the ECG circuit determines up to three ECG waveforms, which are digitized using an analog-to-digital converter mounted proximal to the ECG circuit, and sent through a cable 282 to the wrist-worn transceiver 272 according to the CAN protocol. There, the ECG and PPG waveforms are processed to determine the patient's blood pressure. Heart rate and respiratory rate are determined directly from the ECG waveform using known algorithms, such as those described above. The cable bulkhead 274 also includes an accelerometer that measures motion associated with the patient's chest as described above.

There are several advantages of digitizing ECG and ACC waveforms prior to transmitting them through the cable 282. First, a single transmission line in the cable 282 can transmit multiple digital waveforms, each generated by different sensors. This includes multiple ECG waveforms (corresponding, e.g., to vectors associated with three, five, and twelve-lead ECG systems) from the ECG circuit mounted in the bulkhead 274, along with waveforms associated with the x, y, and z axes of accelerometers mounted in the bulkheads 274, 296. Limiting the transmission line to a single cable reduces the number of wires attached to the patient, thereby decreasing the weight and cable-related clutter of the body-worn monitor. Second, cable motion induced by an ambulatory patient can change the electrical properties (e.g. electrical impendence) of its internal wires. This, in turn, can add noise to an analog signal and ultimately the vital sign calculated from it. A digital signal, in contrast, is relatively immune to such motion-induced artifacts.

More sophisticated ECG circuits can plug into the wrist-worn transceiver to replace the three-lead system shown in FIGS. 23A and 23B. These ECG circuits can include, e.g., five and twelve leads.

FIG. 24 shows a close-up view of the wrist-worn transceiver 272. As described above, it attaches to the patient's wrist using a flexible strap 290 which threads through two D-ring openings in a plastic housing 206. The transceiver 272 houses portions of the circuits 175, 140 described in FIGS. 20 and 21, and additionally features a touchpanel display 200 that renders a GUI 273 which is altered depending on the viewer (typically the patient or a medical professional). Specifically, the transceiver 272 includes a small-scale infrared barcode scanner 202 that, during use, can scan a barcode worn on a badge of a medical professional. The barcode indicates to the transceiver's software that, for example, a nurse or doctor is viewing the user interface. In response, the GUI 273 displays vital sign data and other medical diagnostic information appropriate for medical professionals. Using this GUI 273, the nurse or doctor, for example, can view the vital sign information, set alarm parameters, and enter information about the patient (e.g. their demographic information, medication, or medical condition). The nurse can press a button on the GUI 273 indicating that these operations are complete. At this point, the display 200 renders an interface that is more appropriate to the patient, such as time of day and battery power.

As described above, the transceiver 272 features three CAN connectors 204a-c on the side of its upper portion, each which supports the CAN protocol and wiring schematics, and relays digitized data to the internal CPU. Digital signals that pass through the CAN connectors include a header that indicates the specific signal (e.g. ECG, ACC, or pressure waveform from the cuff-based module) and the sensor from which the signal originated. This allows the CPU to easily interpret signals that arrive through the CAN connectors 204a-c, and means that these connectors are not associated with a specific cable. Any cable connecting to the transceiver can be plugged into any connector 204a-c. As shown in FIG. 23A, the first connector 204a receives the cable 282 that transports a digitized ECG waveform determined from the ECG circuit and electrodes, and digitized ACC waveforms measured by accelerometers in the cable bulkhead 274 and the bulkhead portion 296 associated with the ECG cable 282.

The second CAN connector 204b shown in FIG. 22 receives the cable 286 that connects to the pneumatic cuff-based system 285 used for the pressure-dependent indexing measurement (shown in FIG. 23A). This connector 204b receives a time-dependent pressure waveform delivered by the pneumatic system 285 to the patient's arm, along with values for SYS, DIA, and MAP values determined during the indexing measurement. The cable 286 unplugs from the connector 204b once the indexing measurement is complete, and is plugged back in after approximately four hours for another indexing measurement.

The final CAN connector 204c can be used for an ancillary device, e.g. a glucometer, infusion pump, body-worn insulin pump, ventilator, or end-tidal $CO_2$ delivery system. As described above, digital information generated by these systems will include a header that indicates their origin so that the CPU can process them accordingly.

The transceiver 272 includes a speaker 201 that allows a medical professional to communicate with the patient using a voice over Internet protocol (VOIP). For example, using the speaker 201 the medical professional could query the patient from a central nursing station or mobile phone connected to a wireless, Internet-based network within the hospital. Or the medical professional could wear a separate transceiver similar to the shown in FIG. 24, and use this as a communication device. In this application, the transceiver 272 worn by the patient functions much like a conventional cellular telephone or 'walkie talkie': it can be used for voice communications with the medical professional and can additionally relay information describing the patient's vital signs and motion. The speaker can also enunciate pre-programmed messages to the patient, such as those used to calibrate the chest-worn accelerometers for a posture calculation, as described above.

In addition to those methods described above, the body-worn monitor can use a number of additional methods to calculate blood pressure and other properties from the optical and electrical waveforms. These are described in the following co-pending patent applications, the contents of which are incorporated herein by reference: 1) CUFFLESS BLOOD-PRESSURE MONITOR AND ACCOMPANYING WIRELESS, INTERNET-BASED SYSTEM (U.S. Ser. No. 10/709,015; filed Apr. 7, 2004); 2) CUFFLESS SYSTEM FOR MEASURING BLOOD PRESSURE (U.S. Ser. No. 10/709,014; filed Apr. 7, 2004); 3) CUFFLESS BLOOD PRESSURE MONITOR AND ACCOMPANYING WEB SERVICES INTERFACE (U.S. Ser. No. 10/810,237; filed Mar. 26, 2004); 4) CUFFLESS BLOOD PRESSURE MONITOR AND ACCOMPANYING WIRELESS MOBILE DEVICE (U.S. Ser. No. 10/967,511; filed Oct. 18, 2004); 5) BLOOD PRESSURE MONITORING DEVICE FEATURING A CALIBRATION-BASED ANALYSIS (U.S. Ser. No. 10/967,610; filed Oct. 18, 2004); 6) PERSONAL COMPUTER-BASED VITAL SIGN MONITOR (U.S. Ser. No. 10/906,342; filed Feb. 15, 2005); 7) PATCH SENSOR FOR MEASURING BLOOD PRESSURE WITHOUT A CUFF (U.S. Ser. No. 10/906,315; filed Feb. 14, 2005); 8) PATCH SENSOR FOR MEASURING VITAL SIGNS (U.S. Ser. No. 11/160,957; filed Jul. 18, 2005); 9) WIRELESS, INTERNET-BASED SYSTEM FOR MEASURING VITAL SIGNS FROM A PLURALITY OF PATIENTS IN A HOSPITAL OR MEDICAL CLINIC (U.S. Ser. No. 11/162,719; filed Sep. 9, 2005); 10) HAND-HELD MONITOR FOR MEASURING VITAL SIGNS (U.S. Ser. No. 11/162,742; filed Sep. 21, 2005); 11) CHEST STRAP FOR MEASURING VITAL SIGNS (U.S. Ser. No. 11/306,243; filed Dec. 20, 2005); 12) SYSTEM FOR MEASURING VITAL SIGNS USING AN OPTICAL MODULE FEATURING A GREEN LIGHT SOURCE (U.S. Ser. No. 11/307,375; filed Feb. 3, 2006); 13) BILATERAL DEVICE, SYSTEM AND METHOD FOR MONITORING VITAL SIGNS (U.S. Ser. No. 11/420,281; filed May 25, 2006); 14) SYSTEM FOR MEASURING VITAL SIGNS USING BILATERAL PULSE TRANSIT TIME (U.S. Ser. No. 11/420,652; filed May 26, 2006); 15) BLOOD PRESSURE MONITOR (U.S. Ser. No. 11/530,076; filed Sep. 8, 2006); 16) TWO-PART PATCH SENSOR FOR MONITORING VITAL SIGNS (U.S. Ser. No. 11/558,538; filed Nov. 10, 2006); and, 17) MONITOR FOR MEASURING VITAL SIGNS AND RENDERING VIDEO IMAGES (U.S. Ser. No. 11/682,177; filed Mar. 5, 2007).

Other embodiments are also within the scope of the invention. For example, other measurement techniques, such as conventional oscillometry measured during deflation, can be used to determine SYS for the above-described algorithms. Additionally, processing units and probes for measuring pulse oximetry similar to those described above can be modified and worn on other portions of the patient's body. For example, pulse oximetry probes with finger-ring configurations can be worn on fingers other than the thumb. Or they can be modified to attach to other conventional sites for measuring SpO2, such as the ear, forehead, and bridge of the nose. In these embodiments the processing unit can be worn in places other than the wrist, such as around the neck (and supported, e.g., by a lanyard) or on the patient's waist (supported, e.g., by a clip that attaches to the patient's belt). In still other embodiments the probe and processing unit are integrated into a single unit.

In other embodiments, a set of body-worn monitors can continuously monitor a group of patients, wherein each patient in the group wears a body-worn monitor similar to those described herein. Additionally, each body-worn monitor can be augmented with a location sensor. The location sensor includes a wireless component and a location-processing component that receives a signal from the wireless component and processes it to determine a physical location of the patient. A processing component (similar to that described above) determines from the time-dependent waveforms at least one vital sign, one motion parameter, and an alarm parameter calculated from the combination of this information. A wireless transceiver transmits the vital sign, motion parameter, location of the patient, and alarm parameter through a wireless system. A remote computer system featuring a display and an interface to the wireless system receives the information and displays it on a user interface for each patient in the group.

In embodiments, the interface rendered on the display at the central nursing station features a field that displays a map corresponding to an area with multiple sections. Each section corresponds to the location of the patient and includes, e.g., the patient's vital signs, motion parameter, and alarm parameter. For example, the field can display a map corresponding to an area of a hospital (e.g. a hospital bay or emergency room), with each section corresponding to a specific bed, chair, or general location in the area. Typically the display renders graphical icons corresponding to the motion and alarm parameters for each patient in the group. In other embodiments, the body-worn monitor includes a graphical display that renders these parameters directly on the patient.

Typically the location sensor and the wireless transceiver operate on a common wireless system, e.g. a wireless system based on 802.11, 802.15.4, or cellular protocols. In this case a location is determined by processing the wireless signal with one or more algorithms known in the art. These include, for example, triangulating signals received from at least three different base stations, or simply estimating a location based on signal strength and proximity to a particular base station. In still other embodiments the location sensor includes a conventional global positioning system (GPS).

The body-worn monitor can include a first voice interface, and the remote computer can include a second voice interface that integrates with the first voice interface. The location sensor, wireless transceiver, and first and second voice interfaces can all operate on a common wireless system, such as one of the above-described systems based on 802.11 or cellular protocols. The remote computer, for example, can be a monitor that is essentially identical to the monitor worn by the patient, and can be carried or worn by a medical professional. In this case the monitor associated with the medical professional features a GUI wherein the user can select to display information (e.g. vital signs, location, and alarms) corresponding to a particular patient. This monitor can also include a voice interface so the medical professional can communicate directly with the patient.

Still other embodiments are within the scope of the following claims.

What is claimed is:

1. An optical sensor configured to be worn on a patient's finger and determine an optical signal indicative of a photoplethysmograph waveform, the sensor comprising:
    a flexible housing configured to wrap around a portion of the base of the patient's thumb and position over the interior base of the thumb proximate to the princeps pollicis artery, the flexible housing comprising (i) a first light source that emits optical radiation, wherein the first light source comprises a first substantially planar surface, (ii) a photodetector configured to detect the optical radiation and to generate the optical signal, wherein the photodetector is positioned on a substrate comprising a second substantially planar surface, and (iii) a plurality of living hinges, the first and second substantially planar surfaces are supported by the flexible housing such that the first substantially planar surface is separated from the second substantially planar surface by an included angle between 35-55 degrees, wherein the included angle is an angle formed between a first line drawn parallel to the first substantially planar surface and a second line drawn parallel to the second substantially planar surface, wherein the flexible housing is an approximately semicircular housing with the plurality of living hinges radially spaced apart from each other along a circumference of the approximately semicircular housing.

2. The optical sensor according to claim 1, further comprising circuitry configured to receive the optical signal and covert the optical signal into a photoplethysmograph waveform.

3. An optical sensor according to claim 2, wherein the photoplethysmograph waveform is an analog waveform.

4. An optical sensor according to claim 1, comprising a second light source proximate to the first light source.

5. An optical sensor according to claim 4, wherein the first light source operates in the 400-700 nm range, and the second light source operates in the 700-1000 nm range.

6. A method of obtaining an optical signal indicative of a photoplethysmograph waveform, comprising:
    positioning a flexible housing around the base of a patient's thumb, wherein the housing comprises (i) a first light source that emits optical radiation, wherein the first light source comprises a first substantially planar surface, (ii) a photodetector configured to detect the optical radiation and to generate the optical signal, wherein the photodetector is positioned on a substrate comprising a second substantially planar surface, and (iii) a plurality of living hinges, the first and second substantially planar surfaces are supported by the flexible housing such that the first substantially planar surface is separated from the second substantially planar surface by an included angle between 35-55 degrees, wherein the included angle is an angle formed between a first line drawn parallel to the first substantially planar surface and a second line drawn parallel to the second substantially planar surface, wherein the first light source and photodetector are each positioned over the interior base of the thumb proximate to the princeps pollicis artery, wherein the flexible housing is an approximately semicircular housing with the plurality of living hinges radially spaced apart from each other along a circumference of the approximately semicircular housing;
    energizing the light source to illuminate the thumb with optical radiation; and
    detecting optical radiation after reflection by the princeps pollicis artery with the photodetector and generating an optical signal therewith.

7. A method according to claim 6, further comprising converting the optical signal into a photoplethysmograph waveform.

8. A method according to claim 7, further comprising determining one or more of a blood oxygen saturation level, a pulse rate, pulse transit time, and blood pressure for the patient using the photoplethysmograph waveform.

9. A method according to claim 6, wherein the housing comprises a second light source proximate to the first light source.

* * * * *